US010732175B2

(12) United States Patent
Wang et al.

(10) Patent No.: US 10,732,175 B2
(45) Date of Patent: Aug. 4, 2020

(54) POLYMER BASED SIGNAL AMPLIFICATION FOR PROTEIN AND CELL DETECTION

(71) Applicant: The Penn State Research Foundation, University Park, PA (US)

(72) Inventors: Yong Wang, State College, PA (US); Erin Gaddes, Bellefonte, PA (US); Jinping Lai, State College, PA (US); Niancao Chen, Boston, MA (US)

(73) Assignee: The Penn State Research Foundation, University Park, PA (US)

( * ) Notice: Subject to any disclaimer, the term of this patent is extended or adjusted under 35 U.S.C. 154(b) by 453 days.

(21) Appl. No.: 15/378,923

(22) Filed: Dec. 14, 2016

(65) Prior Publication Data

US 2017/0166952 A1 Jun. 15, 2017

Related U.S. Application Data

(60) Provisional application No. 62/266,980, filed on Dec. 14, 2015, provisional application No. 62/346,782, filed on Jun. 7, 2016.

(51) Int. Cl.
| | |
|---|---|
| *C12Q 1/68* | (2018.01) |
| *G01N 33/53* | (2006.01) |
| *G01N 33/68* | (2006.01) |
| *C12Q 1/6816* | (2018.01) |
| *C12Q 1/6804* | (2018.01) |
| *C12Q 1/682* | (2018.01) |

(52) U.S. Cl.
CPC ......... *G01N 33/5308* (2013.01); *C12Q 1/682* (2013.01); *C12Q 1/6804* (2013.01); *C12Q 1/6816* (2013.01); *G01N 33/68* (2013.01); *G01N 2458/10* (2013.01)

(58) Field of Classification Search
None
See application file for complete search history.

(56) References Cited

U.S. PATENT DOCUMENTS

| | | | |
|---|---|---|---|
| 5,273,882 | A | 12/1993 | Snitman et al. |
| 6,110,687 | A | 8/2000 | Nilsen |
| 7,727,721 | B2 | 6/2010 | Pierce et al. |
| 8,143,004 | B2 | 3/2012 | Ikebukuro et al. |
| 8,630,809 | B2 | 1/2014 | Kleinbaum |
| 2002/0172950 | A1 | 11/2002 | Kenny et al. |
| 2005/0260635 | A1 | 11/2005 | Dirks et al. |

FOREIGN PATENT DOCUMENTS

WO 2012004790 1/2012

OTHER PUBLICATIONS

Gunderson et al, Genome Res. 14: 870 (2004).*
Wang et al ,Biosensors and Bioelectronics 63: 153 (published online Jul. 18, 2014 and in journal form Jan. 15, 2015.*
Agasti et al., 2012 "Photocleavable DNA barcode-antibody conjugates allow sensitive and multiplexed protein analysis in single cell", Journal of American Chem Soc., vol. 134(45): pp. 18499-18502 (1-10).
Anderson et al., 2013, "PCR-less DNAco-polymerization detection of Shiga like toxin1(stx1) in *Escherichia coli* O157:H7", Biosensors and Bioelectronics, vol. 42: pp. 581-585.
Anne et al., 2007, "Enzymatic Redox 3¢-End-Labeling of DNA Oligonucleotide Monolayers on Gold Surfaces Using Terminal Deoxynucleotidyl Transferase (TdT)-Mediated Single Base Extension", J. Am. Chem. Soc., vol. 129: pp. 2734-2735.
Bath et al., 2007, "DNA Nanomachines", University of Oxford, Department of Physics, Clarendon Laboratory, Parks Road, Oxford OX1 3PU, United Kingdom, pp. 1-31.
Bi et al., 2015 "Hyperbranched Hybridization Chain Reaction for Triggered Signal Amplification and Concatenated Logic Circuits", Angew. Chem. Int. Ed., vol. 54, pp. 8144-8148.
Brunsveld et al., 2001 "Supramolecular Polymers", Chem. Rev., vol. 101, pp. 4071-4097.
Chen, 2015 "Programmable Nanomaterials for Deoxification", A Dissertation in Biomedical Engineering, The Pennsylvania State University, pp. 1-124.
Chow et al., 2007 "Surface-Initiated Enzymatic Polymerization of DNA", Langmuir, vol. 23, pp. 11712-11717.
DePedro et al., 2004 "Restricted Mobility of Cell Surface Proteins in the Polar Regions of *Escherichia coli*", Journal of Bacteriology, vol. 186, No. 9: pp. 2594-2602.
Dirks et al., 2004 "Triggered amplification by hybridization chain reaction", PNAS, vol. 101(43): pp. 15275-15278.
Gao et al., 2005 "In vivo molecular and cellular imaging with quantum dots", Current Opinion in Biotechnology, vol. 16: pp. 63-72.
Idili et al., 2015 "Controlling Hybridization Chain Reactions with pH", Nano Letters, vol. 15: pp. 5539-5544.
Jungmann et al., 2014, "Multiplexed 3D Cellular Super-Resolution Imaging with DNA-PAINT and Exchange-PAINT", Nat Methods, vol. 11(3):pp. 313-318.
Lee et al., 1970 "A Physical Study by Electron Microscopy of the Terminally Repetitious, Circularly Permuted DNA from the Coliphage Particles of *Escherichia coli* 15", J. MoZ. Biol., vol. 48, I-22.
Lehn 1985 "Supramolecular Chemistry: Receptors, Catalysts, and Carriers", Science, vol. 227, No. 4689: pp. 849-856.
Lehn 2005 "Dynamers: dynamic molecular and supramolecular polymers", Prog. Polym. Sci., vol. 30:pp. 814-831.

(Continued)

*Primary Examiner* — James Martinell
(74) *Attorney, Agent, or Firm* — Meunier Carlin & Curfman LLC

(57) ABSTRACT

The present invention relates generally to compositions, methods and kits for detection of a molecule of interest. The present invention is based, at least in part, on the design of nucleic acid oligonucleotides such that they can be used as molecular building blocks which can be assembled (polymerized) to form a dsDNA polymerization product which can be detected and further, can be disassembled (depolymerized) such that the polymerization product is no longer detectable. The invention can be performed multiple times on the same cell population, and is therefore useful for highly sensitive in situ detection of multiple biomarkers.

37 Claims, 35 Drawing Sheets

Specification includes a Sequence Listing.

(56) References Cited

OTHER PUBLICATIONS

Gaddes et al., 2015 "Aptamer-Based Polyvalent Ligands for Regulated Cell Attachment on the Hydrogel Surface", Biomacromolecules, Article, pp. A-H.
Oshovsky et al., 2007 "Supramolecular Chemistry in Water", Angew. Chem. Int. Ed., vol. 46, pp. 2366-2393.
Pappas et al., 2007 "Cellular separations: A review of new challenges in analytical chemistry", Analytica Chimica Acta, vol. 601: pp. 26-35.
Pirici et al., 2009 "Antibody Elution Method for Multiple Immunohistochemistry on Primary Antibodies Raised in the Same Species and of the Same Subtype", Journal of Histochemistry & Cytochemistry, vol. 57(6): pp. 567-575.
Resch-Genger et al., 2008 "Quantum dots versus organic dyes as fluorescent labels", Nature Methods, vol. 5(9): pp. 763-775.
Richards et al., 2014 "Polymerization of Affinity Ligands on a Surface for Enhanced Ligand Display and Cell Binding", Biomacromolecules, vol. 15: pp. 4561-4569.
Rothemund, 2016 "Folding DNA to create nanoscale shapes and patterns", Nature, vol. 440: pp. 297-302.
Rowan et al., 2002 "Dynamic Covalent Chemistry", Angew. Chem. Int. Ed., vol. 41: pp. 898-952.
Schweller, 2012 "Multiplexed in situ Immunofluorescence via Dynamic DNA Complexes", Angew Chem Int Ed Engl., vol. 51(37): 9292-9296.
Seeman, 2003, "DNA in a material world", Nature, vol. 421: pp. 427-431.
Sijbesma et al., 1997, "Reversible Polymers Formed from Self-Complementary Monomers Using Quadruple Hydrogen Bonding", Science, vol. 278: pp. 1601-1604.
Song et al., 2012 "Hybridization chain reaction-based aptameric system for the highly selective and sensitive detection of protein", Analyst, vol. 137: pp. 1396-1401.
Stubbs et al., 2000, "Subcellular Localization, Mobility, and Kinetic Activity of Glucokinase in Glucose-Responsive Insulin-Secreting Cells", Diabetes, vol. 49: pp. 2048-2055.
Wahlby et al., 2002, "Sequential Immunofluorescence Staining and Image Analysis for Detection of Large Numbers of Antigens in Individual Cell Nuclei", Cytometry, vol. 47:pp. 32-41.
Weiner et al., 2010, "Antibodies and cancer therapy: versatile platforms for cancer immunotherapy", Nat Rev Immunol., vol. 10(5): pp. 317-327.
Wetmur et al., 1968, "Kinetics of Renaturation of DNA", J. Mol. Biol., vol. 31: pp. 349-370.
Yurke et al., 2000, "A DNA-fuelled molecular machine made of DNA", Nature, vol. 406: pp. 605-608.
Zhang et al., 2011, "Dynamic Dna nanotechnology using strand-displacement reactions", Nature Chemistry, vol. 3: pp. 103-113.
Zhang et al. 2012, "Highly Sensitive Detection of Protein with Aptamer-Based Target-Triggering Two-Stage Amplification", Anal. Chem., vol. 84: pp. 1623-1629.
Zrazhevskiy et al., 2013, "Quantum dot imaging platform for single-cell molecular profiling", Nature Communications, vol. 4:1619: pp. 1-12.
Chen et al., Molecularly Regulated Reversible DNA Polymerization, Angew Chem Int Ed Engl. 2016;55(23):6657-6661.
Garcia-Fernandez et al., Dual Photosensitive Polymers with Wavelength-Selective Photoresponse, Adv Mater, 2014, 26:5012-5017.
Liu et al., Hyperbranched Sefl-Immolative Polymers (hSIPs) fo Programed Payload Delivery and Ultrasensitive Detection, J Am Chem Soc, 2015, 137:11645-11655.
Mastronardi et al., Smanr Materials Based on DNA Aptamers: Taking Aptasensing to the Next Level, Sensors, 2014, 14:3156-3171.
Shah et al., Single-molecule RNA detection at depth by hybridization chain reaction and tissue hydrogel embedding and clearing, Development. Aug. 1, 2016; 143(15): 2862-2867.

\* cited by examiner

POLYMER BASED SIGNAL AMPLIFICATION FOR PROTEIN AND CELL DETECTION

CROSS-REFERENCE TO RELATED APPLICATIONS

This application claims priority to U.S. Provisional Application No. 62/266,980, filed Dec. 14, 2015, and U.S. Provisional Application No. 62/346,782, filed Jun. 7, 2016, which are hereby incorporated by reference herein in their entirety.

STATEMENT REGARDING FEDERALLY SPONSORED RESEARCH OR DEVELOPMENT

This invention was made with government support under Grant No. DMR1322332, awarded by The National Science Foundation. The Government has certain rights in the invention.

BACKGROUND OF THE INVENTION

Detection of cellular proteins is needed for both basic life sciences research and clinical applications since proteins play essential roles in virtually each step of cellular metabolism (Wu and Singh, Curr Opin Biotechnol. 2012, 23:83-8.; Collins et al., Nature. 2003, 422:835-47; Schubert, Adv Biochem Eng Biotechnol. 2003, 83:189-209; Paez et al., Science. 2004, 304:1497-500; Soda et al., Nature. 2007; 448:561-U563; Bendall et al., Science. 2011; 332:687-696). However, proteins to be examined often have very low levels (Boschetti and Righetti, Low-Abundance Proteome Discovery: State of the Art and Protocols. 2013:1-11; Baracat-Pereira et al., Genet Mol Biol. 2012, 35:283-91; Wasinger et al., Methods Mol Biol. 2008, 424:257-75; Ackermann and Berna, Expert Rev Proteomics. 2007, 4:175-86; Ahmed and Rice, J Chromatogr B Analyt Technol Biomed Life Sci. 2005, 815:39-50). This problem may result from a small size of samples in the scenarios such as the analysis of rare circulating tumor cells, forensic specimens, and prenatal testing samples (Wang et al., Nano Today, 2013, 8:347-387; Deng et al., Sci Rep. 2014 Dec. 16; 4:7499; Zhang et al., Anal Chem. 2015, 87:9761-8; Danova et al., Expert Rev Mol Diagn. 2011, 11:473-85; Nagrath et al., Nature. 2007, 450:1235-9; Hanson and Ballantyne, Anal Biochem. 2005, 346:246-257; Denecke et al., Pediatr Res. 2005, 58:248-253; Yamamoto et al., Diagn Mol Pathol. 2004, 13:167-71). It may also result from the fact that certain proteins have a low abundance (e.g., cell membrane receptors and transcription factors) (Brewis and Brennan, Adv Protein Chem Str. 2010, 80:1-44). Their expression can be over ten orders of magnitudes lower than those highly expressed proteins (e.g., albumin in serum) (Brewis and Brennan, Adv Protein Chem Str. 2010, 80:1-44). Nevertheless their biological functions are not marginal; on the contrary, most of them make huge physiological impacts on cells at an extremely low concentration (Spitz and Furlong, Nat Rev Genet. 2012, 13:613-626). Therefore, it is important to develop highly sensitive methods for detection of proteins, particularly low-abundance proteins or those in a small sample (Wang et al., Nano letters. 2011, 11:498-504; Wang et al., ACS nano. 2011, 5:6619-6628; Crow et al., Am J Roentgenol. 2009, 192:1021-1028, Aaron et al., Nano letters. 2009, 9:3612-3618; Austin et al., J Am Chem Soc. 2011, 133(44): 17594-17597, Qian et al., J Biomed Opt. 2010, 15:046025; Seekell et al., J Biomed Opt. 2011, 16; Crow et al., ACS nano. 2011, 5:8532-8540; Kennedy et al., ACS nano. 2009, 3:2329-2339; Wang et al., Nano letters. 2012, 12:3231-3237; Fraire et al., ACS nano. 2014, 8:8942-8958).

To detect proteins, cells are often lysed to release proteins in a soluble form. Hundreds of soluble proteins can be examined quickly and precisely using mass spectrometry (MS), which has advantages such as no need to pre-label target proteins and femtomolar sensitivity in the analysis of pure proteins (Passarelli and Ewing, Curr Opin Chem Biol. 2013, 17:854-9; Jarecki et al., ACS Chem Neurosci. 2013, 4:418-34; Boggio et al., Expert Rev Proteomics. 2011, 8:591-604; Bandura et al., Anal Chem. 2009, 81:6813-22). Soluble proteins are also routinely measured with signal amplification using the enzyme-linked immunosorbent assay (ELISA) with the limit of detection at the level of pg/mL (Zhang et al., J Immunol Methods. 2011, 368:1-23; Ponde, Eur J Clin Microbiol Infect Dis. 2013, 32:985-988; Tijssen and Adam, Curr Opin Immunol. 1991, 3:233-7; Nilsson, Curr Opin Immunol. 1989, 2:898-904). ELISA can be further tuned and integrated with polymerase chain reaction (PCR) to develop immuno-PCR or nanotechnologies to develop plasmonic ELISA for ultrasensitive detection of proteins (Niemeyer et al., Nat Protoc. 2007, 2:1918-30; Sano et al., Science. 1992, 258:120-122; Burbulis et al., Nat Methods. 2005, 2:31-37; de la Rica and Stevens, Nat Nanotechnol. 2012, 7:821-824; Nam et al., Science. 2003, 301: 1884-1886). Many other methods such as immunoblot analysis can also be used for detection of soluble or solubilized proteins (Hughes et al., Nat Methods. 2014, 11:749-U794; Pumford et al., Toxicol Appl Pharmacol. 1990, 104: 521-32; von Wulffen et al., J Clin Pathol. 1988, 41:653-659). These highly sensitive methods require cell lysis and/or protein separation, which are not suitable for situations where whole cells are still needed during and after examination. For instance, the ability to maintain cell integrity is a prerequisite for examining location and distribution of proteins in a cell. Thus, whole-cell in situ protein analysis methods have also been rigorously studied as an alternative solution to those problems.

Immunostaining is a commonly used method for whole-cell analysis (Zola, Current protocols in cytometry/editorial board, J. Paul Robinson, 2004, Chapter 6:Unit 6 3; Turac et al., PloS one. 2013, 8; D'Hautcourt, Current protocols in cytometry/editorial board, J. Paul Robinson, 2002, Chapter 6:Unit 6 12; Fung et al., Nat Protoc. 2010, 5:357-370; Glynn and McAllister, Nat Protoc, 2006, 1:1287-1296; Perez et al., Current protocols in cytometry/editorial board, J. Paul Robinson. 2005, Chapter 6:Unit 6 20; Almeida and Bueno, Current protocols in cytometry/editorial board, J. Paul Robinson. 2001; Chapter 6:Unit 6 6). Cells are labeled with antibodies bearing fluorophores for microscopic examination or flow cytometry (Fung et al., Nat Protoc. 2010, 5:357-370; Glynn and McAllister, Nat Protoc, 2006, 1:1287-1296; Perfetto et al., Nat Rev Immunol. 2004, 4:648-55; Ullal et al., Sci Transl Med. 2014; 6; Zrazhevskiy and Gao, Nat Commun. 2013; 4:1619; Pirici et al., J Histochem Cytochem. 2009, 57: 567-575; Schweller et al., Angew Chem Int Ed Engl. 2012, 51:9292-9296). Since cell immunostaining does not need cell lysis or protein separation, sample pretreatment is relatively simple and has no problem of protein dilution. Proteins are also confined in their original locations (Huh et al., Nature. 2003, 425:686-691). If cell receptors are target proteins for examination, living cells can be directly analyzed and further used for other purposes (e.g., cell culture) afterwards. While immunostaining has been widely used for successful protein examination, spectral overlap of fluorophores is a challenging issue that often limits the measurement to a few proteins. Importantly, most of conventional methods lack the function of signal amplification.

Therefore, there is a need in the art to develop new methods that in principle have no limit of analyzing a multitude of proteins with high sensitivity. Further, there is a need for such methods to pair with protein detection methods (e.g. immunofluorescence assays) such that proteins can be detected while in their original cellular location. Such methods are particularly needed for many contemporary life science studies and clinical applications that often require comprehensive, spatially delineated analyses of complex protein pathways and molecular networks (Collins et al., Nature. 2003, 422:835-47; Zrazhevskiy and Gao, Nat Commun. 2013; 4:1619; Jaiswal et al., Nat Methods. 2004, 1:73-78; Wei et al., Angew Chem Int Ed Engl. 2014, 53:5573-5577; Howarth et al, Nat Methods. 2008, 5:397-399; Jaiswal et al, Nat Biotechnol. 2003, 21:47-51; Han et al., Nature. 2004, 430:88-93; Chen and Murphy, J Biomed Biotechnol. 2005, 2005:87-95; Taban et al., J Am Soc Mass Spectrom. 2007, 18:145-51; Altelaar et al., Nat Protoc. 2007, 2:1185-1196; McDonnell and Heeren, Mass Spectrom Rev. 2007, 26:606-43; Schubert et al., Nat Biotechnol. 2006, 24:1270-8).

SUMMARY OF THE INVENTION

The invention relates to a method for detection of one or more molecule of interest, the method comprising: (a) a polymerization step (b) a detection step and (c) a depolymerization step.

In one embodiment, the polymerization step comprises hybridizing an initiator ssDNA oligonucleotide with one or more hairpin DNA oligonucleotides to form a double-stranded DNA (dsDNA) polymerization product.

In one embodiment, the initiator ssDNA oligonucleotide is selected from the group consisting of SEQ ID NO: 1, SEQ ID NO: 12 and SEQ ID NO: 13. In one embodiment, the initiator ssDNA oligonucleotide is SEQ ID NO: 1 and the one or more hairpin DNA oligonucleotides comprise one or more sequences selected from the group consisting of SEQ ID NO: 2, SEQ ID NO: 3, SEQ ID NO:4 and SEQ ID NO:5. In one embodiment, the initiator ssDNA oligonucleotide is SEQ ID NO: 12 and the one or more hairpin DNA oligonucleotide comprise one or more sequences selected from the group consisting of SEQ ID NO: 14, SEQ ID NO: 15 and SEQ ID NO: 16. In one embodiment, the initiator ssDNA oligonucleotide is SEQ ID NO: 13 and wherein the one or more hairpin DNA oligonucleotide comprise one or more sequences selected from the group consisting of SEQ ID NO: 17 and SEQ ID NO: 18.

In one embodiment, the dsDNA polymerization product comprises one or more ssDNA side groups. In one embodiment, the dsDNA polymerization product is extended to become a branched product. In one embodiment, the branched product is formed from hybridization of a ssDNA oligonucleotide to a side group of the dsDNA polymerization product. In one embodiment, the ssDNA oligonucleotide is conjugated to a molecule. In one embodiment, the molecule is selected from the group consisting of a quantum dot, a monomeric fluorophore, a polymeric fluorophore and biotin.

In one embodiment, the dsDNA polymerization product results from contacting an initiator ssDNA oligonucleotide having a sequence as set forth in SEQ ID NO: 1 with at least two hairpin DNA oligonucleotide selected from the group consisting of SEQ ID NO: 2, SEQ ID NO: 3, SEQ ID NO:4 and SEQ ID NO:5, and is further extended into a branched product by contacting the dsDNA polymerization product with one or more DNA oligonucleotides selected from the group consisting of SEQ ID NO: 6, SEQ ID NO:7 and SEQ ID NO:8.

In one embodiment, the invention relates to a method for detection of one or more molecule of interest, the method comprising: (a) a polymerization step (b) a detection step and (c) a de-polymerization step and further comprising (d) a targeting step.

In one embodiment, the targeting step comprises contacting a molecule to be detected with a targeting complex. In one embodiment, the targeting complex includes a ssDNA oligonucleotide component, and a linker molecule. In one embodiment, the ssDNA oligonucleotide component comprises a sequence selected from the group consisting of SEQ ID NO: 1, SEQ ID NO: 12 and SEQ ID NO: 13. In one embodiment, the linker molecules is selected from the group consisting of a peptide, a protein, an immunogenic particle, an antibody, an oligonucleotide, and a microparticle.

In one embodiment, the molecule to be detected is a biological molecule. In one embodiment, polymerization is initiated at the site of a biological molecule through the linkage of the initiator ssDNA oligonucleotide to the biological molecule through the association of the targeting complex. In one embodiment, the biological molecule is selected from the group consisting of a peptide, a protein, and a nucleic acid.

In one embodiment, the detection step comprises detection of a dsDNA polymerization product. In one embodiment, detection comprises detection of a DNA-conjugated molecule. In one embodiment, the DNA-conjugated molecule is conjugated to a DNA oligonulceotide selected from the group consisting of a ssDNA oligonucleotide and a hairpin DNA oligonucleotide. In one embodiment, at least a portion of the DNA oligonucleotide is complementary to a side group of a dsDNA polymerization product.

In one embodiment, the DNA-conjugated molecule is conjugated to a ssDNA oligonucleotide having a sequence as set forth in SEQ ID NO: 21, having a region complementary to a side group of a dsDNA polymerization product formed from hybridization of SEQ ID NO: 14 with SEQ ID NO: 15.

In one embodiment, the DNA-conjugated molecule is conjugated to a ssDNA oligonucleotide having a sequence as set forth in SEQ ID NO: 22, having a region complementary to a side group of a dsDNA polymerization product formed from hybridization of SEQ ID NO: 17 with SEQ ID NO: 18.

In one embodiment, the detectable molecule is a quantum dot, a DNA-conjugated monomeric fluorophore or a DNA-conjugated polymeric fluorophore.

In one embodiment, a DNA-conjugated fluorophore is a polymerization of one of a succinimidyl ester activated fluorophore, Coumarin, FITC or TRITC.

In one embodiment, the detection step comprises detection of multiple dsDNA polymerization products in a single sample. In one embodiment, multiple dsDNA polymerization products, are formed concurrently in a single sample.

In one embodiment, one dsDNA polymerization product has an initiator ssDNA oligonucleotide as set forth in SEQ ID NO: 12 and wherein the hairpin DNA oligonucleotides are selected from the group consisting of SEQ ID NO: 14, SEQ ID NO: 15 and SEQ ID NO: 16, and another dsDNA polymerization product has an initiator ssDNA oligonucleotide as set forth in SEQ ID NO: 13 and wherein the hairpin DNA oligonucleotides are selected from the group consisting of SEQ ID NO: 17 and SEQ ID NO: 18.

In one embodiment, the depolymerization step comprises depolymerization of a linear dsDNA or branched product. In one embodiment, a DNA oligonucleotide hybridizes competitively with a DNA hairpin oligonucleotide to disengage it from the linear dsDNA or branched product. In one embodiment, the competitive hybridization is initiated through hybridization to a side group of the linear dsDNA product, and extends through a region of complementary sequence to the hairpin DNA oligonucleotide. In one embodiment, the hairpin DNA oligonucleotides that hybridized to form a linear dsDNA product are inactivated for further polymerization.

In one embodiment, the depolymerization DNA oligonucleotide comprises a sequence of SEQ ID NO: 10 or SEQ ID NO:11.

In one embodiment, parts (a), (b) and (c) are performed sequentially in a manner as to generate a detectable dsDNA polymer at the site of a biological molecule and subsequently detect and then remove the detectable dsDNA polymer.

In one embodiment, parts (a), (b) and (c) are performed sequentially in a manner as to generate multiple detectable dsDNA polymers at the site of multiple biological molecules and subsequently detect and then remove the detectable dsDNA polymers.

In one embodiment, parts (a), (b), (c) are performed sequentially, multiple times within the same sample serving as a method for detection of multiple biological molecules.

In various embodiments, parts (a), (b) and (c) can be performed in vivo, in vitro or in situ.

In one embodiment, parts (a), (b), (c) and (d) are performed on a biological sample.

The invention also relates to a kit comprising an initiator ssDNA oligonucleotide, a hairpin DNA oligonucleotide, and a depolymerization ssDNA oligonucleotide. In one embodiment, a hairpin DNA oligonucleotide is conjugated to a detectable molecule. In one embodiment, the initiator ssDNA oligonucleotide is linked to a molecule as a targeting complex.

In one embodiment, a kit of the invention comprises a ssDNA oligonucleotide conjugated to a molecule. In one embodiment, the molecule is a DNA-conjugated monomeric or polymeric fluorophore. In one embodiment, a DNA-conjugated polymeric fluorophore is a polymerization of one of Coumarin, FITC or TRITC. In one embodiment, the molecule is biotin and the kit further includes a streptavidin conjugated detectable molecule. In one embodiment, the streptavidin conjugated detectable molecule is a quantum dot.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts a schematic representation of the reversible polymerization of LP (upper panel) and BP via ATRP fluorescent polymer formation and hybridization with LP branch points (lower panel). The brown dots indicate the depolymerization-triggering molecules. FIG. 1B depicts a detailed schematic representation of reversible polymerization of LP with one side group, including illustrated DNA secondary structure changes.

FIG. 2, comprising FIG. 2B depicts a schematic diagram of the secondary structures of different LPs.

FIG. 3, comprising FIG. 3A depicts LP polymerization. FIG. 3B depicts LP depolymerization.

FIG. 5, comprising FIG. 5A depicts the results from gel electrophoresis of the LP polymerization. FIG. 5B depicts the results from atomic force microscopy (AFM) of the LP polymerization. FIG. 5C depicts the results from gel electrophoresis of the reversal of LP polymerization. FIG. 5D depicts the results from AFM of the reversal of LP polymerization. Lane 1 of FIG. 5C: DM1s1, DM2 and T1 were mixed and annealed to form the LP. The white boxes indicate the bands of LP (lane 1) and reversed LP (lane 6) had the same position, suggesting that they had the same structure.

FIG. 7, comprising FIG. 7A depicts a schematic diagram of LP reversing. FIG. 7B depicts the results of gel electrophoresis of LP reversing with different reversing time. FIG. 7C depicts the quantification of the time effect on LP reversing from FIG. 7B (n=2).

FIG. 8, comprising FIG. 8A depicts a schematic diagram of LP reversing. FIG. 8B depicts the results of gel electrophoresis of LP reversing with different T1 and DM1s1 ratios. FIG. 8C depicts the quantification of the effect of T1 and DM1s1 ratio on LP reversing from 8B (n=3).

FIG. 10, comprising FIG. 10A depicts a schematic illustration of microparticles with one fluorescent hybridized unit and a fluorescent LP. FIG. 10B depicts the flow cytometry histograms and fluorescence intensity quantification of microparticles (n=3) with a single fluorescent hybridized unit and a fluorescent LP. The insert is fluorescence images of microparticle suspensions.

FIG. 11, comprising FIG. 11A depicts a schematic illustration of LP reversing on microparticle surface. FIG. 11B depicts fluorescence intensity quantification of microparticles with fluorescent LP after different treatments (n=3). The insert is fluorescence images of microparticle suspensions. DM2 was labeled with fluorophore at the 3' end.

FIG. 12, comprising FIG. 12A depicts confocal microscopy images of fibroblast targeted with antibody-DI conjugate to which one fluorescent unit has hybridized or a fluorescent LP has formed. FIG. 12B depicts the fluorescence intensity quantification of confocal images (n=3). Scale bar 50 µm applies to all confocal images.

FIG. 13, comprising FIG. 13A depicts confocal microscopy images of fibroblast with a fluorescence LP before and after treatment with T1. FIG. 13B depicts the fluorescence profiles across the region indicated by a red line in FIG. 13A. FIG. 13C depicts the quantification of the average fluorescence intensity of confocal images (n=3). Scale bar 50 µm applies to all confocal images.

FIG. 20, comprising FIG. 20A depicts a DNA-conjugated polymeric fluorophore attached to an oligonucleotide complementary to the k side group. FIG. 20B depicts a DNA-conjugated fluorophore attached to DM1 s1 side group.

FIG. 22, comprising FIG. 22A depicts a schematic diagram of DI-4FB linking reaction. FIG. 22B depicts results of a fluorescamine assay showing reduction of fluorescence intensity as amine groups are linked with S-4FB, blocking the conjugation with fluoresamine groups. FIG. 22C depicts the results of an agarose gel electrophoresis experiment showing polymerization before (lane 2) and after (lane 3) DI modification. Error bars represent standard deviation (n=3).

FIG. 23, comprising FIG. 23A depicts a schematic diagram of antibody-HyNic linking reaction. FIG. 23B depicts the results of a fluorescamine assay showing reduction of fluorescence intensity as amine groups are linked with S-HyNic, blocking the conjugation with fluoresamine groups. Error bars represent standard deviation (n=3).

FIG. 24, comprising FIG. 24A depicts a diagram of the chemical reaction which occurs when 4FB-modified DI and HyNic-modified antibody react to form a linked DI-antibody conjugate. FIG. 24B depicts an SDS PAGE (non-reducing) image showing antibody and DI-antibody conjugates with lane descriptions provided in a table to the right.

FIG. 25, comprising FIG. 25A depicts a diagram showing that each set of polymers consists of one initiator, DI, and two hairpin monomers (DM1 and DM2) that sequentially hybridize to form a linear DNA polymer. One monomer in each set contains a toehold for the specific hybridization of a fluorophore. FIG. 25B depicts gel electrophoresis images for each set of DNA polymers. Set 1 monomers are denoted DM1_1 and DM2_1, while Set 2 monomers are called DM1_2 and DM2_2. Fluorescence intensity from SYBR Safe staining of double-stranded DNA is pseudo-colored green (Set 1) or red (Set 2). FIG. 25C depicts flow cytometry analysis of DNA polymerization. Microparticles are conjugated with either DI (green label), one monomer unit (orange label), multiple monomer units (red label), or left bare and incubated with monomers (purple label).

FIG. 26, comprising FIG. 26A depicts gel electrophoresis analysis of the formation of polymers with either Set 1 monomers (FAM, green) or Set 2 monomers (Cy5, red). Gel image is a merge of green and red channels, where yellow indicates fluorescence overlap. FIG. 26B depicts flow cytometric analysis of polymerization specificity. Top panel compares bare particles (green), DI1+DI2 functionalized particles (purple) and bare particles incubated with fluorescent monomers (yellow). Center panel compares DI1-particles with all monomers, but only Set 1 fluorescently labeled (green), DI1-particles with all monomers, but only Set 2 fluorescently labeled (purple), and DI1+DI2 particles with Set 1 monomers labeled (yellow). Lower panel compares DI2-particles with all monomers, but only Set 1 fluorescently labeled (green), DI2-particles with all monomers, but only Set 2 fluorescently labeled (purple), and DI1+DI2 particles with Set 2 monomers labeled (yellow).

FIG. 27, comprising FIG. 27A depicts a schematic illustration of amine groups on DI conjugated to linking molecule, S-4FB to form 4FB-modified DI. FIG. 27B depicts the average percent of amine groups modified for DI1 and DI2 based on fluorescamine assay. FIG. 27C depicts fluorescamine analysis of modified amine groups on DI1 and DI2. Fluorescence intensity increases as fluorescamine binds free amine groups, indicating the degree of modification by S-4FB. FIG. 27D depicts gel electrophoresis images comparing polymerization with unmodified and modified DI for each set. Equal amounts of modified and unmodified DI were used, as well as equal amounts of monomers. Signal from SYBR Safe stain indicates double-stranded DNA, pseudocolored green for Set 1 and red for Set 2. All error bars represent standard deviation (n=3); *P≤0.05.

FIG. 28, comprising FIG. 28A depicts an illustration of 4FB-DI and HyNic-Antibody reacting to form covalently bonded conjugates. FIG. 28B depicts gel electrophoresis for examination of conjugate purity. DI and Antibody-DI conjugate solutions were incubated with a linear sequence complementary to DI for visualization of secondary DNA structure with SYBR Safe staining. FIG. 28C depicts reducing SDS PAGE analysis of the upward shift in molecular weight of antibodies following conjugation with DI.

FIG. 29, comprising FIG. 29A, first column, depicts schematics and images of cells labeled with either unconjugated DI1 (row 1), unconjugated β tubulin antibody (row 2), or DI1-anti β tubulin conjugates (row 3). Cells are then incubated with monomer solution (second column) and fluorophore solution (third column). FIG. 29B depicts fluorescence intensity analysis of cells labeled in (A). Error bars represent standard deviation (n=3); *P≤0.05; N. S. marks no significant difference.

FIG. 30, comprising FIG. 30A, first column, displays fluorescence images of cells labeled with either unconjugated DI2 (row 1), unconjugated COX4 antibody (row 2), or DI2-anti COX4 conjugates (row 3). Cells are then incubated with monomer solution (second column) and fluorophore solution (third column). FIG. 30B depicts fluorescence intensity analysis of cells labeled in FIG. 30A. Error bars represent standard deviation (n=3); *P≤0.05; N. S. marks no significant difference.

FIG. 31, comprising FIG. 31A depicts control solutions compared to conjugate, monomer, and fluorophore labeling for Set 1 conjugates. FIG. 31B depicts control solutions compared to conjugate, monomer, and fluorophore labeling for Set 2 conjugates. For each set, samples were incubated with solutions of monomers, fluorophores, monomers and then fluorophores, or conjugates and then fluorophores. These controls were then compared to samples incubated with conjugates, monomers, and then fluorophores. The average fluorescence intensity of cells was quantified, with error bars representing standard deviation (n=3); *P≤0.05 compared to all other samples; N. S. marks no significant difference compared to all other samples.

FIG. 33, comprising FIG. 33A depicts fixed cells were labeled with equal amounts of either FITC-β tubulin primary antibody (direct antibody fluorophore label), unlabeled β tubulin primary antibody+AlexaFluor 488 secondary antibody (indirect antibody fluorophore label), or β tubulin antibody-DT1 conjugates (for both monomer label and polymer label samples). One monomer was incubated with monomer labeled conjugates, while a solution of both monomers were incubated with polymer labeled conjugates. All conjugate samples were hybridized with Qdot 525. Confocal images were taken under identical conditions for the β tubulin label. Nuclei are labeled with DAPI in all images. FIG. 33B depicts the quantitative analysis of fluorescence intensities from samples in FIG. 33A. Error bars represent standard deviation (n=3); *P≤0.05; All other sample comparisons exhibited no significant differences.

FIG. 35, comprising FIG. 35A depicts a diagram showing that the DNA polymers contain hybridization regions for a reversing sequence (RS) to bind and competitively displace the monomers, resulting in depolymerization. FIG. 35B depicts a gel electrophoresis image of DNA polymers before (lane 1) and after the addition of RS (lane 2). FIG. 35C depicts flow cytometric analysis of RS-triggered depolymerization of quantum dot-labeled DNA polymers.

DETAILED DESCRIPTION

Figures 1A, 1B:
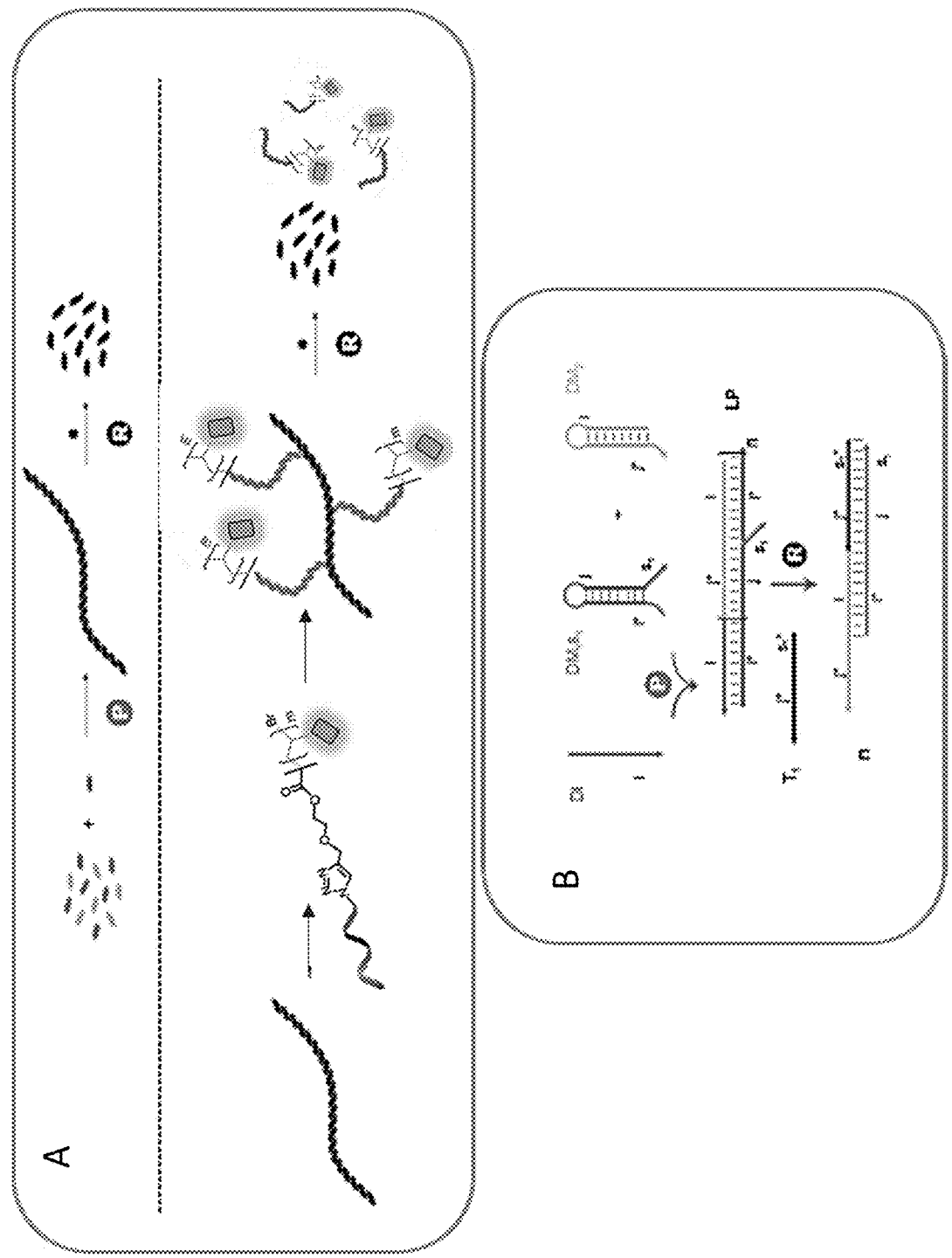
FIG. 1A through FIG. 1B, is a series of images depicting the process of molecular regulated reversible DNA polymerization of the dsDNA product in the form of a linear polymer (LP) or branched polymer (BP). Circles of green "P" and red "R" indicate polymerization and depolymerization reactions.

The present invention relates generally to compositions, methods and kits for detection of a molecule of interest. The present invention is based, at least in part, on the design of nucleic acid oligonucleotides such that they can be used as molecular building blocks which can be assembled (polymerized) to form a dsDNA polymerization product which can be detected and disassembled (depolymerized) such that the polymerization product is no longer detectable. This invention is useful, for example, as a method for amplification of a detectable label, such as a fluorescent signal, to detectable levels.

In one embodiment, the invention allows detection of a molecule of interest through association of a polymerization-triggering ssDNA oligonucleotide to a biological molecule, or molecule of interest, through a targeting complex. In one embodiment, a targeting complex includes linkage of a polymerization-triggering ssDNA oligonucleotide to an antibody for detecting a protein. In one embodiment, a targeting complex includes linkage of a polymerization-triggering ssDNA oligonucleotide to a nucleic acid sequence for detecting a complementary nucleic acid.

In one embodiment, the invention eliminates one of the difficulties inherent in immuno-fluorescent assays such as low fluorescent signal from a single fluorophore detecting a single protein. In one embodiment, this occurs through hybridization of multiple fluorescently labeled DNA molecules to form a fluorescently labeled polymerization product conjugated to a molecule of interest through a targeting complex. In an alternative embodiment, this is achieved through hybridization of a polymeric fluorescent molecule to a linear dsDNA molecule that is the product of a polymerization reaction and is conjugated to a molecule of interest through a targeting complex.

In one embodiment, the polymeric fluorescent molecule is a molecule in which more than one, as represented by M, fluorophores have polymerized, this molecule hybridizes to more than one, as represented by N, ssDNA oligonucleotide side groups extending from a linear dsDNA molecule that is the product of a polymerization. In this embodiment, M*N fluorescent molecules are used to detect a single protein.

In one embodiment, the invention utilizes the natural ability of DNA oligonucleotides to hybridize with complementary partners in a reaction that does not require the addition of enzymes or harsh hybridization conditions. This aspect of the invention provides an advantage of allowing the invention to be utilized in such a manner that the physiological conditions of the sample can be maintained.

In one aspect, the invention includes depolymerization of an existing dsDNA polymerization product through the addition of a competitive ssDNA oligonucleotide. In one embodiment, the invention includes depolymerization of a fluorescent dsDNA polymerization product through competitive hybridization reactions. In one embodiment, an amplified fluorescent signal for detection of a single protein is reversed.

Further, in one embodiment, an additional fluorescent dsDNA polymerization product can be assembled and subsequently disassembled at a different location in the same sample as the initial dsDNA polymerization product. In this aspect, the invention includes a method for detection of multiple proteins in a single sample through repeated assembly, detection, and disassembly of a dsDNA polymerization product.

In yet another aspect, the present invention pertains to a kit for detecting the presence of a target molecule in a test sample. The kit contains (1) a nucleic acid component conjugated to a molecule that enables protein recognition, and (2) a hybridization monomer which forms a linear dsDNA polymerization product upon interaction with the initiation component. In one embodiment, the kit additionally contains multiple sets of hybridization monomers which form a multi-branched polymerization product from the linear dsDNA polymerization product. In one embodiment, one of the nucleic acid sequences contains a detectable label. In a particular embodiment, the kit additionally contains a detectable label conjugated to a monomeric component of a polymer that hybridizes to the linear dsDNA polymerization product, forming a branched fluorescent polymer.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

It is also to be understood that the terminology used herein is for the purpose of describing particular embodiments only, and is not intended to be limiting.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, or ±10%, or ±5%, or ±1%, or ±0.1% from the specified value, as such variations are appropriate to perform the disclosed methods.

The terms "biomarker" and "marker" are used herein interchangeably. They refer to a substance that is a distinctive indicator of a biological process, biological event and/or pathologic condition.

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, "conjugated" refers to covalent attachment of one molecule to a second molecule.

"Contacting" refers to a process in which two or more molecules or two or more components of the same molecule or different molecules are brought into physical proximity such that they are able undergo an interaction. Molecules or components thereof may be contacted by combining two or more different components containing molecules, for example by mixing two or more solution components, preparing a solution comprising two or more molecules such as target, candidate or competitive binding reference molecules, and/or combining two or more flowing components. Alternatively, molecules or components thereof may be contacted combining a fluid component with molecules immobilized on or in a substrate, such as a polymer bead, a membrane, a polymeric glass substrate or substrate surface derivatized to provide immobilization of target molecules, candidate molecules, competitive binding reference molecules or any combination of these. Molecules or components thereof may be contacted by selectively adjusting solution conditions such as, the composition of the solution, ion strength, pH or temperature. Molecules or components thereof may be contacted in a static vessel, such as a microwell of a microarray system, or a flow-through system, such as a microfluidic or nanofluidic system. Molecules or components thereof may be contacted in or on a variety of media, including liquids, solutions, colloids, suspensions, emulsions, gels, solids, membrane surfaces, glass surfaces, polymer surfaces, vesicle samples, bilayer samples, micelle samples and other types of cellular models or any combination of these.

The term "depolymerization" as used herein includes the process of two DNA sequences attaching together through hybridization such that one of the DNA sequences which was previously hybridized in a polymerization of DNA oligonucleotides is now hybridized to a single oligonucleotide and no longer is a participant in the dsDNA polymerization product.

The term "DNA" as used herein is defined as deoxyribonucleic acid.

The term "ssDNA" includes a single free strand of polymerized deoxyribonucleic acids consisting of repeated polymer bases of adenine (A), cytosine (C), guanine (G), and/or thymine (T), where each strand has directionality and runs from five prime (5') to three prime (3').

The term "dsDNA" includes a complex of two ssDNA strands that are hybridized to each other in a complimentary fashion (adenine:thymine and cytosine:guanine), the two strands run anti-parallel to each other and form a helical structure, such that at any given end a 5'-end from one strand and a 3'-end from another strand are present. As used herein, the term "dsDNA" includes pseudo-dsDNA molecules.

The term "fluorophore" includes a molecule that absorbs a photon of a wavelength and emits a photon of another wavelength. The term "fluorophore" includes DNA-conjugated monomeric and polymeric formulations of fluorescent molecules. As used herein, "fluorophore" includes but is not limited to fluorescein, coumarin, fluorescein isothiocyanate (FITC), or tetramethylrhodamine (TRITC), semiconductor quantum dots (QDs), upconversion phosphors (UCNPs). The term "fluorophore" also refers to a moiety that is inherently fluorescent or demonstrates a change in fluorescence upon binding to a biological compound or metal ion, or metabolism by an enzyme, i.e., fluorogenic. Fluorophores may be substituted to alter the solubility, spectral properties or physical properties of the fluorophore. Numerous fluorophores are known to those skilled in the art and include, but are not limited to coumarins, acridines, furans, dansyls, cyanines, pyrenes, naphthalenes, benzofurans, quinolines, quinazolinones, indoles, benzazoles, borapolyazaindacene, oxazines and xanthenes, with the latter including fluoresceins, rhodamines, rosamines and rhodols.

The term "fluorescent polymer" refers to polymers with multiple fluorophore. The fluorescent polymer can be synthesized via various polymerization reaction using fluorophore as monomer, includes atom transfer radical polymerization (ATRP), ring-opening metathesis polymerization (ROMP), reversible addition-fragmentation chain transfer polymerization (RAFT), nitroxide-mediated polymerization (NMP) or free radical polymerization. The fluorescent polymer can also be prepared via the post functionalization of various polymers with fluorophores. The polymers refer to various linear polymers, star polymers, or block polymers, and the backbone of the polymers include, but are not limited to poly(ethylene glycol) (PEG), poly (ethylene oxide) (PEO), poly (D, L-lactic-co-glycolic acid) (PLGA), polyacrylamide, poly (N-isopropylacrylamide) (PNIPAM), poly[tri(ethylene glycol)ethyl ether methacrylate] (pTriEGMA), poly(propylene oxide) (PPO), poly(ethyleneimine) (PEI), poly(L-lysine) and poly(pyrrole). The post functionalization can be achieved via various chemical or physical crosslinking such as Cu-catalyzed azide/alkyne cycloaddition (CuAAC reaction), thiol-ene/yne click reaction, oxime condensation, Diels-Alder cycloaddition, Michael addition, activated ester coupling, pryidyl disulfide reaction, to name a few.

In addition to the polymers carrying fluorophores, DNA-functionalized chelating polymers can be similarly designed. The chelating polymer consists of a polymer backbone and a grafted chelating group. The chelating group can be used to bind metal ions for protein and cell imaging.

"Homologous, homology" or "identical, identity" as used herein, refer to comparisons among amino acid and nucleic acid sequences. When referring to nucleic acid molecules, "homology," "identity," or "percent identical" refers to the percent of the nucleotides of the subject nucleic acid sequence that have been matched to identical nucleotides by a sequence analysis program. Homology can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the ExPaSy is used to align sequence fragments of genomic DNA sequences. However, equivalent alignment assessments can be obtained through the use of any standard alignment software.

The term "hybridization" refers to the process in which two single-stranded nucleic acids bind non-covalently to form a double-stranded nucleic acid; triple-stranded hybridization is also theoretically possible. Complementary sequences in the nucleic acids pair with each other to form a double helix. The resulting double-stranded nucleic acid is a "hybrid." Hybridization may be between, for example, two complementary or partially complementary sequences. The hybrid may have double-stranded regions and single stranded regions. The hybrid may be, for example, DNA: DNA, RNA:DNA or DNA:RNA. Hybrids may also be formed between modified nucleic acids. One or both of the nucleic acids may be immobilized on a solid support. Hybridization techniques may be used to detect and isolate specific sequences, measure homology, or define other characteristics of one or both strands.

The stability of a hybrid depends on a variety of factors including the length of complementarity, the presence of mismatches within the complementary region, the temperature and the concentration of salt in the reaction.

A first oligonucleotide anneals with a second oligonucleotide with "high stringency" if the two oligonucleotides anneal under conditions whereby only oligonucleotides which are at least about 75%, and preferably at least about 90% or at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known.

As used herein, an "immunoassay" refers to any binding assay that uses an antibody capable of binding specifically to a target molecule to detect and quantify the target molecule.

The term "interact" or "interaction" refers to a measurable chemical or physical interaction between a target molecule and a candidate molecule that is capable of affecting the structure and/or composition of a target molecule, a candidate molecule or both such that the biological activity of the target molecule, the candidate molecule or both is affected. Interactions capable of affecting the structure and/or composition of a molecule include, but are not limited to, reactions resulting in the formation of one or more covalent bonds, resulting in the breaking of one or more covalent bonds, electrostatic associations and repulsions, formation and/or disruption of hydrogen bonds, formation and/or disruption of electrostatic forces such as dipole-dipole interactions, formation and/or disruption of van der Waals interactions or processes comprising combinations of these.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

The term "nucleotide base," as used herein, refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases adenine, guanine, cytosine, 6 methyl-cytosine, uracil, thymine, and analogs of the naturally occurring nucleotide bases, e.g., 7-deazaadenine, 7-deazaguanine, 7-deaza-8-azaguanine, 7-deaza-8-azaadenine, N6 delta 2-isopentenyladenine (6iA), N6-delta 2-isopentenyl-2-methylthioadenine (2 ms6iA), N2-dimethylguanine (dmG), 7methylguanine (7mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, 06-methylguanine, N6-methyladenine, 04-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385-394, CRC Press, Boca Raton, Fla., and the references cited therein.

The term "nucleotide," as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR2 or halogen groups, where each R is independently H, C1-C6 alkyl or C5-C14 aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-anomeric nucleotides, 1'-anomeric nucleotides, 2'-4'- and 3'-4'-linked and other "locked" or "LNA", bicyclic sugar modifications (see, e.g., PCT published application nos. WO 98/22489, WO 98/39352; and WO 99/14226). The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T." The term "oligonucleotide" includes a DNA molecule having from 8 bases to 1000 bases in length and being single stranded.

The term "overhang," as used herein, refers to terminal non-base pairing nucleotide(s) resulting from one strand or region extending beyond the terminus of the complementary strand to which the first strand or region forms a duplex. One or more polynucleotides that are capable of forming a duplex through hydrogen bonding can have overhangs. The single-stranded region extending beyond the 3' end of the duplex is referred to as an overhang.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polymerization hybridization" includes the process of two DNA sequences attaching together through hybridization in a repeating fashion to create a double stranded DNA strand longer than either of the individual sequences.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning and amplification technology, and the like, and by synthetic means. An "oligonucleotide" as used herein refers to a short polynucleotide, typically less than 100 bases in length.

Conventional notation is used herein to describe polynucleotide sequences: the left-hand end of a single-stranded polynucleotide sequence is the 5'-end. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences." In the sequences described herein:

A=adenine,

G=guanine,

T=thymine,

C=cytosine,

The skilled artisan will understand that all nucleic acid sequences set forth herein throughout in their forward orientation, are also useful in the compositions and methods of the invention in their reverse orientation, as well as in their forward and reverse complementary orientation, and are described herein as well as if they were explicitly set forth herein.

The term "probe" as used herein refers to nucleic acid oligomers prepared using a solid support or amidite of the invention. In various embodiments, the probes produce a detectable response upon interaction with a binding partner. The probes include at least one detectable moiety, or a pair of moieties that form an energy transfer pair detectable upon some change of state of the probe in response to its interaction with a binding partner.

The term "pseudo-dsDNA" as used herein includes any base-paired DNA molecule that is not fully paired. It will be understood that pseudo-dsDNA molecules may contain nicks, gaps (regions of ssDNA) or un-hybridized ssDNA side groups interspersed among dsDNA regions.

The term "sequence" includes the specific nucleotide base configuration in a linear 5-prime to 3-prime order.

The term "side group" as used herein, refers to unhybridized ssDNA regions that extend from a pseudo-dsDNA polymerization product. The term "side group" includes ssDNA regions having between 1 and 40 nucleotides.

In some instances, the terms "specific binding" or "specifically binding", can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "strand" includes oligonucleotide.

The term "structure" as used herein refers any formation of polymerized oligonucleotides or pseudo-dsDNA molecule that is formed from a polymerization hybridization reaction.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

In one embodiment, the invention is a method for in situ detection of a molecule of interest involving polymerization, detection, and depolymerization of a dsDNA polymerization product.

In one embodiment, the molecule for detection is a biological molecule. In one embodiment, the biological molecule for detection is a nucleic acid molecule. In one embodiment, the nucleic acid molecule is one of DNA or RNA. In one embodiment, the molecule of interests is a polypeptide molecule. In one embodiment, the polypeptide molecule is a protein.

In one embodiment, detection involves the interaction of a biological molecule or molecule of interest with a targeting complex. In one embodiment, the targeting complex is formed from the linkage of a ssDNA oligonucleotide to a targeting molecule.

In one embodiment, a targeting molecule has specific binding to a polypeptide. In one embodiment, a targeting molecule is an antibody. In one embodiment, the antibody is a monoclonal antibody. In one embodiment, the antibody is a polyclonal or chimeric antibody.

In one embodiment a targeting molecule has specificity for a nucleic acid sequence. In one embodiment, the targeting molecule is a nucleic acid sequence.

In one embodiment, the targeting complex involves a ssDNA oligonucleotide complexed to an antibody. In one embodiment, the oligonucleotide is complexed to an antibody through a biotin/streptavidin interaction. In one embodiment, the oligonucleotide is complexed to an antibody through amide coupling. In one embodiment, the oligonucleotide is complexed to an antibody through a covalent linkage. In one embodiment, the oligonucleotide is complexed to an antibody through a chemical reaction. In one preferred embodiment, the linkage of a ssDNA to a targeting molecule in the targeting complex occurs through an antibody conjugated to S-HyNic interacting with an initiating ssDNA oligonucleotide conjugated to S-4FB.

In one aspect, the invention comprises a multi-step method for polymerization, detection and depolymerization of a dsDNA molecule.

Polymerization

One aspect of the invention is polymerization of a dsDNA product. In one embodiment, polymerization is initiated by the ssDNA oligonucleotide component of the targeting complex. In one embodiment, the targeting complex serves to localize a polymerization reaction to a molecule of interest. In one embodiment, the polymerization reaction results in a dsDNA product complexed to a molecule of interest.

In one embodiment, a dsDNA product polymerizes through repeated hybridization of DNA monomers to an initiating ssDNA oligonucleotide. In one embodiment, an initiating ssDNA oligonucleotide is part of a targeting complex. In one embodiment, the hybridization DNA monomers are hairpin-forming DNA molecules. In one embodiment, polymerization requires interaction of one or more hybridization monomers with the initiating ssDNA oligonucleotide. In one embodiment, a mixture of DNA monomers is required for a polymerization reaction.

In one embodiment, hybridization monomers include regions that do not participate in the polymerization reaction. In this embodiment, the regions form unhybridized side groups extending from a dsDNA polymerization product. In one embodiment, a dsDNA polymerization product may have 0, 1, or more than 1 side group. In one embodiment, polymerization can continue exponentially through interaction of additional hybridization monomers with a dsDNA polymerization product having 1 or more than one side group.

In one embodiment, the invention is the ordered addition of DNA hairpin monomers to an initiating DNA molecule or existing DNA polymerization product with one hairpin of the mixture being introduced having a region of specificity to a side group extending from the existing DNA polymerization product. In this aspect, the invention is not limited with respect to the number of hairpin DNA molecules that combine to create a dsDNA polymerization product.

In one embodiment, a polymerization product is formed by contacting an initiating oligonucleotide comprising a sequence as set forth in SEQ ID NO: 1 with a mixture of DNA hairpin monomers in which one DNA hairpin monomer comprises a sequence selected from the group consisting of SEQ ID NO: 2 and SEQ ID NO: 3 and a second DNA hairpin monomer comprises a sequence selected from the group consisting of SEQ ID NO: 4 and SEQ ID NO: 5. In another embodiment, a polymerization product is formed by contacting an initiating oligonucleotide comprising a sequence as set forth in SEQ ID NO: 12 with a mixture of DNA hairpin monomers in which one DNA hairpin monomer comprises a sequence as set forth in SEQ ID NO: 14 and a second DNA hairpin monomer comprises a sequence selected from the group consisting of SEQ ID NO: 15 and SEQ ID NO: 16. In yet another embodiment, a polymerization product is formed by contacting an initiating oligonucleotide comprising a sequence as set forth in SEQ ID NO: 13 with a mixture of DNA hairpin monomers in which one DNA hairpin monomer comprises a sequence as set forth in SEQ ID NO: 17 and a second DNA hairpin monomer comprises a sequence as set forth in SEQ ID NO: 18.

Detection

One aspect of the invention is detection of a polymerization product that forms at the site of a molecule of interest. In one embodiment, detection involves direct detection of the polymerization reaction. In one embodiment, detection involves detection of an existing dsDNA polymerization product.

In one embodiment, a detectable label is conjugated to a DNA hybridization monomer that forms the dsDNA polymerization product. In this embodiment the detectable label is incorporated into the dsDNA polymerization product. In one embodiment, the number of detectable molecules incorporated into the dsDNA polymerization product is one. In one embodiment, the number of detectable molecules incorporated into the dsDNA polymerization product is more than one.

In one embodiment, a detectable molecule that is conjugated to one of the DNA molecules that forms the dsDNA polymerization product is one of an inorganic particle, a nanoparticle, a quantum dot (QD), a quantum dot molecule (QDM), an organic molecule, a polymer, a DNA-conjugated polymer, and a fluorescent molecule. Suitable fluorophores for the invention include, but are not limited to, fluorescein, FAM (6-fluorescein amidite), sulforhodamine 101, pyrenebutanoate, acridine, ethenoadenosine, eosin, rhodamine, 5-(2'-aminoethyl)aminonaphthalene (EDANS), fluorescein isothiocyanate (FITC), N-hydroxysuccinimidyl-1-pyrenesulfonate (PYS), tetramethylrhodamine (TAMRA), Rhodamine X, Cy5 and erythrosine. In one embodiment, the detectable molecule is a polymeric fluorescent molecule. In one embodiment, the polymeric fluorescent molecule is a polymerization of one of FITC, TRITC, or coumarin. In one embodiment, the polymeric fluorescent molecule is a polymerization of any fluorescent molecule.

In one embodiment, detection involves hybridization of a detection complex to a formed dsDNA polymerization product. In one embodiment, a detection complex is a ssDNA oligonucleotide complexed to a detectable molecule. In one embodiment, hybridization of a detection complex to a formed dsDNA polymerization product occurs through hybridization of the ssDNA oligonucleotide component of the detection complex to a side group extending from the formed dsDNA polymerization product.

In one embodiment, the detectable molecule of the detection complex is one of an inorganic particle, a nanoparticle, a QD, a QDM, an organic molecule, a polymer, a DNA-conjugated polymer, a fluorescent molecule. In one embodiment, a fluorescent molecule of the detection complex is fluorescein. Suitable fluorophores for the invention include, but are not limited to, fluorescein, FAM (6-fluorescein amidite), sulforhodamine 101, pyrenebutanoate, acridine, ethenoadenosine, eosin, rhodamine, 5-(2'-aminoethyl)aminonaphthalene (EDANS), fluorescein isothiocyanate (FITC), N-hydroxysuccinimidyl-1-pyrenesulfonate (PYS), tetramethylrhodamine (TAMRA), Rhodamine X, Cy5 and erythrosine. In one embodiment, the detectable molecule is a polymeric fluorescent molecule. In one embodiment, the polymeric fluorescent molecule is a polymerization of one of FITC, TRITC, or coumarin. In one embodiment, the polymeric fluorescent molecule is a polymerization of any fluorescent molecule.

In one embodiment, a detection complex is a ssDNA oligonucleotide complexed to a molecule which interacts with a detectable molecule or otherwise produces a detectable signal. In various embodiments, a ssDNA oligonucleotide may be complexed to an antigen, an antibody, biotin, or an enzyme. In one embodiment, a detection complex comprises a ssDNA oligonucleotide conjugated to biotin whereby the detection complex can further be contacted by a detectable molecule conjugated to streptavidin and the signal can be detected. The detection complex thus serves to link a detectable molecule coated with streptavidin to the dsDNA polymerization product. In one embodiment, the detectable molecule is a QD coated with streptavidin.

In one embodiment, the detection complex comprises a ssDNA oligonucleotide having the sequence as set forth in SEQ ID NO: 9 is conjugated to biotin, and has a region complementary to and capable of hybridizing to a region of a dsDNA polymerization product resulting from the polymerization of monomers with sequences as set forth in SEQ ID NO: 3 and SEQ ID NO: 5. In one embodiment, the detection complex comprises a ssDNA oligonucleotide having the sequence as set forth in SEQ ID NO: 21 is conjugated to biotin on the 3'end, and has a region complementary to and capable of hybridizing to a region of a dsDNA polymerization product resulting from the polymerization of monomers with sequences as set forth in SEQ ID NO: 14 and SEQ ID NO: 15. In one embodiment, the detection complex comprises a ssDNA oligonucleotide having the sequence as set forth in SEQ ID NO: 22 is conjugated to biotin on the 5' end, and has a region complementary to and capable of hybridizing to a region of a dsDNA polymerization product resulting from the polymerization of monomers with sequences as set forth in SEQ ID NO: 17 and SEQ ID NO: 18.

Depolymerization

Another aspect of the invention is depolymerization of an existing dsDNA polymerization product. In one embodiment, depolymerization of a formed dsDNA polymerization product with 1 or more unhybridized ssDNA side groups involves introduction of a ssDNA oligonucleotide with specificity to the side group. In one embodiment, depolymerization occurs through competitive hybridization of the ssDNA oligonucleotides to the DNA polymerization monomers. In one embodiment, following depolymerization the polymerization monomers are inactivated for further participation in polymerization reactions. In one embodiment, hybridization of the depolymerization ssDNA oligonucleotide with the targeting complex deactivates the targeting complex from initiating the formation of further dsDNA polymerization products at the molecule of interest.

In one embodiment, addition of a ssDNA oligonucleotide (e.g. comprising a sequence as set forth in SEQ ID NO: 11) to a dsDNA polymerization product formed from the polymerization of monomers (e.g. the product formed from hybridization of SEQ ID NO: 3 and SEQ ID NO: 5) results in depolymerization of the dsDNA polymerization product. In one embodiment, addition of multiple ssDNA oligonucleotides (e.g. comprising a sequence as set forth in SEQ ID NO: 10 and a sequence as set forth in SEQ ID NO: 11) to a dsDNA polymerization product formed from the polymerization of monomers (e.g. a branched product formed from polymerization of SEQ ID NO: 3, SEQ ID NO: 5 and subsequently SEQ ID NO: 7 and SEQ ID NO: 8), results in the depolymerization of the dsDNA polymerization product.

Multi-Analyte Detection

The invention provides methods for multi-analyte detection in a single sample. In various embodiments, the multiple analytes are one of or a combination of nucleic acid molecules and/or proteins.

In one embodiment, multi-analyte detection is performed sequentially. In this embodiment, targeting of a molecule of interest, polymerization of a dsDNA product, detection of the formed product, and depolymerization are performed sequentially multiple times within the same sample.

In one embodiment, distinct initiating sequences and DNA hairpin molecules that do not cross-react with each other can be utilized in a single sample at a single time point. In this embodiment, distinct dsDNA polymerization products are initiated and form at the respective targeting complexes. Further, in this embodiment, detectable molecules that differ in their detection (e.g. fluorescent molecules with different emission wavelengths) are utilized to distinguish the dsDNA polymerization products.

In one embodiment, two "Sets" of initiating sequences, and DNA hairpin molecules that do not cross-react with each other are utilized in a single sample at a single time point. In one embodiment, three, four, five, six, seven, eight, nine, ten, or more than ten sets of initiating sequences, and DNA hairpin molecules that do not cross-react with each other are utilized in a single sample at a single time point.

One exemplary "Set" of initiating sequences, and DNA hairpin molecules is set forth in the group consisting of SEQ ID NO:12, SEQ ID NO:14, and SEQ ID NO:15, wherein SEQ ID NO:12 serves as the initiating sequence and SEQ ID NO:14 and SEQ ID NO:15 are the hybridization monomers which polymerize to form a dsDNA product. A second exemplary Set of initiating sequences, and DNA hairpin molecules is set forth in the group consisting of SEQ ID NO:13, SEQ ID NO:17, and SEQ ID NO:18, wherein SEQ ID NO:13 serves as the initiating sequence and SEQ ID NO:17 and SEQ ID NO:18 are the hybridization monomers which polymerize to form a dsDNA product. In one embodiment, two initiating sequences, (e.g. SEQ ID NO:12 and SEQ ID NO:13), and four hybridization monomers (e.g. SEQ ID NO:14, SEQ ID NO:15, SEQ ID NO:17, and SEQ ID NO:18) are provided concurrently to a sample, whereby two distinct dsDNA polymerization products are formed. In one embodiment, three initiating sequences and six hybridization monomers are provided concurrently to a sample, whereby three distinct dsDNA polymerization products are formed. In one embodiment, four or more initiating sequences and eight or more hybridization monomers are provided concurrently to a sample, whereby four or more distinct dsDNA polymerization products are formed. In one embodiment, five or more initiating sequences and ten or more hybridization monomers are provided concurrently to a sample, whereby five or more distinct dsDNA polymerization products are formed. In one embodiment, ten or more initiating sequences and twenty or more hybridization monomers are provided concurrently to a sample, whereby ten or more distinct dsDNA polymerization products are formed.

One or more ssDNA oligonucleotides, each specific for depolymerization of a single DNA polymerization product, can be added to depolymerize one or more dsDNA polymerization product formed for multiple analyte detection. In various embodiments, one, two, three, four, five, ten or more ssDNA oligonucleotides are added to a sample, whereby one, two, three, four, five, ten or more dsDNA polymerization products. In one embodiment, one, two, three, four, five, ten or more ssDNA depolymerization oligonucleotides are added concurrently to a sample. In one embodiment, one, two, three, four, five, ten or more ssDNA depolymerization oligonucleotides are added sequentially to a sample.

Compositions

The invention relates to single-stranded and hairpin DNA oligonucleotides for use in generating a polymerized DNA scaffold. Conditions for preparation of the ssDNA oligonucleotides and DNA hairpins is not particularly limited and are generally known to one skilled in the art.

The invention includes an initiating ssDNA oligonucleotide. At least a portion of the initiating ssDNA is complementary to a portion of a second oligonucleotide sequence (a hybridization monomer), and serves as an initiator for DNA polymerization. In one embodiment, the initiating ssDNA may be linked to a substrate. In one embodiment, a substrate may be a particle, a bead, a surface, a protein, a nucleic acid molecule, or a compound. In one embodiment, the initiating ssDNA is conjugated to a hydrogel. In various embodiments, the initiating ssDNA is modified at one or more of the 5' end and the 3'end. Such a modification may be allow direct or indirect linkage of the initiating ssDNA oligonucleotide to a substrate. In one embodiment, the ssDNA is conjugated to biotin at the 3' end. In one embodiment, the ssDNA is conjugated to an amine at the 3' end. In one embodiment, the ssDNA is conjugated to Acrydite at the 5' end. In one embodiment, the ssDNA is conjugated to an amino linker C12 at the 5' end. In one embodiment, the ssDNA is conjugated to biotin at the 5' end. In one embodiment, the ssDNA is conjugated to biotin at the 5' end. In various embodiments, an initiating ssDNA has a sequence selected from the group consisting of SEQ ID NO:1, SEQ ID NO:12, and SEQ ID NO:13.

In one embodiment, the method of the invention includes providing a mixture of two or more DNA hairpin molecules which hybridize with the initiating ssDNA oligonucleotide to form a dsDNA polymer product. Therefore, the invention relates to mixtures of hairpin forming oligonucleotides wherein one of the hairpin DNA molecules comprises a region complementary to and capable of hybridization to at least a portion of the initiating ssDNA molecule and further comprises a region complementary to and capable of hybridization to at least a portion of a second hairpin forming oligonucleotide in physiological conditions, and the second hairpin comprises a region on the 5' end complementary to and capable of hybridization to at least a portion of the first hairpin, wherein the portion of the first hairpin is not the 3' end of the first hairpin, and the second hairpin further comprises a region, that is not the 5' end of the second hairpin, complementary to and capable of hybridization to the 3' end of the first hairpin. In one embodiment, one or both hairpin DNA molecules have an additional region, or side group, that does not have a complementary region on either the paired hairpin molecule or the initiating DNA molecule. In one embodiment, a mixture of hairpin forming oligonucleotides comprises SEQ ID NO: 2 and SEQ ID NO: 4. In one embodiment, a mixture of hairpin forming oligonucleotides comprises SEQ ID NO: 2 and SEQ ID NO: 5. In one embodiment, a mixture of hairpin forming oligonucleotides comprises SEQ ID NO: 3 and SEQ ID NO: 4. In one embodiment, a mixture of hairpin forming oligonucleotides comprises SEQ ID NO: 3 and SEQ ID NO: 5. In one embodiment, a mixture of hairpin forming oligonucleotides comprises SEQ ID NO: 14 and SEQ ID NO: 15. In one embodiment, a mixture of hairpin forming oligonucleotides comprises SEQ ID NO: 14 and SEQ ID NO: 16. In one embodiment, a mixture of hairpin forming oligonucleotides comprises SEQ ID NO: 17 and SEQ ID NO: 18.

In one embodiment, the method of the invention includes providing an additional ssDNA or hairpin forming oligonulceotide. In one embodiment, an additional hairpin forming oligonucleotide is a branching oligonucleotide and initiates and extends polymerization from one or more side groups of a dsDNA polymerization product. In one embodiment, a mixture of hairpin DNA oligonucleotides having sequences as set forth in SEQ ID NO: 6 and SEQ ID NO: 8 is provided and extends polymerization from one or more side groups from the dsDNA polymerization product formed from the mixture of SEQ ID NO: 3 and SEQ ID NO: 5, initiated at SEQ ID NO: 1. In one embodiment, a mixture of hairpin DNA oligonucleotides having sequences as set forth in SEQ ID NO: 7 and SEQ ID NO: 8 is provided and extends polymerization from one or more side groups from the dsDNA polymerization product formed from the mixture of SEQ ID NO: 3 and SEQ ID NO: 5, initiated at SEQ ID NO: 1.

In one embodiment, an additional ssDNA or hairpin forming oligonulceotide is conjugated to a detectable molecule, a fluorophore, a protein, a compound or a label. In one embodiment, an additional ssDNA comprises a fluorophore conjugated to a ssDNA oligonucleotide, wherein the ssDNA oligonucleotide has at least a region complementary to a side group of the dsDNA polymerization product formed from polymerization of the hairpin mixture. In one embodiment, an additional ssDNA comprises biotin conjugated to a ssDNA oligonucleotide, wherein the ssDNA oligonucleotide has at least a region complementary to a side group of the dsDNA polymerization product formed from polymerization of the hairpin mixture. In one embodiment, an additional ssDNA comprises an antibody conjugated to a ssDNA oligonucleotide, wherein the ssDNA oligonucleotide has at least a region complementary to a side group of the dsDNA polymerization product formed from polymerization of the hairpin mixture.

In one embodiment the initiating sequence is SEQ ID NO:1 and the hairpin mixture includes one hairpin molecule with a sequence according to either SEQ ID NO: 2 or SEQ ID NO: 3 and one hairpin DNA molecule with a sequence according to SEQ ID NO: 4 or SEQ ID NO: 5. In one embodiment, the hairpin mixture includes SEQ ID NO: 2 and SEQ ID NO: 4. In one embodiment, the hairpin mixture includes SEQ ID NO: 2 and SEQ ID NO: 5. In one embodiment, the hairpin mixture includes SEQ ID NO: 3 and SEQ ID NO: 4. In one embodiment, the hairpin mixture includes SEQ ID NO: 3 and SEQ ID NO: 5. In one embodiment, the hairpin mixture further includes a ssDNA oligonucleotide having a region complementary to and capable of hybridizing to a side group of the dsDNA polymerization product formed from polymerization of the hairpin mixture comprising SEQ ID NO: 2 and SEQ ID NO: 5. In one embodiment, the hairpin mixture further includes a ssDNA oligonucleotide having a region complementary to and capable of hybridizing to a side group of the dsDNA polymerization product formed from polymerization of the hairpin mixture comprising SEQ ID NO: 3 and SEQ ID NO: 4. In one embodiment, the hairpin mixture further includes a ssDNA oligonucleotide having a region complementary to and capable of hybridizing to a side group of the dsDNA polymerization product formed from polymerization of the hairpin mixture comprising SEQ ID NO: 3 and SEQ ID NO: 5. In one embodiment, the hairpin mixture also includes one or more hairpin DNA molecules from the group of SEQ ID NO: 6, SEQ ID NO:7 and SEQ ID NO: 8. In one embodiment, the hairpin mixture includes SEQ ID NO: 3, SEQ ID NO: 5, SEQ ID NO: 7 and SEQ ID NO: 8.

In one embodiment, the initiating sequence is SEQ ID NO: 12 and the hairpin mixture includes one hairpin molecule with a sequence according to SEQ ID NO: 14 and one hairpin DNA molecule with a sequence selected from the group consisting of SEQ ID NO: 15 and SEQ ID NO: 16. In one embodiment, the hairpin mixture further includes a ssDNA oligonucleotide, complementary to and capable of hybridizing to a side group of the dsDNA polymerization product formed from polymerization of the hairpin mixture comprising SEQ ID NO: 14 and SEQ ID NO: 15. In one embodiment, the hairpin mixture further includes a ssDNA oligonucleotide complementary to and capable of hybridizing to a side group of the dsDNA polymerization product formed from polymerization of the hairpin mixture comprising SEQ ID NO: 14 and SEQ ID NO: 16. In one embodiment, the hairpin mixture further includes ssDNA oligonucleotide having the sequence as set forth in SEQ ID NO: 21. In one embodiment, the initiating sequence is SEQ ID NO: 13 and the hairpin mixture includes one hairpin molecule with a sequence as set forth in SEQ ID NO: 17 and one hairpin DNA molecule with a sequence as set forth in SEQ ID NO: 18. In one embodiment, the hairpin mixture further includes a ssDNA oligonucleotide complementary to and capable of hybridizing to a side group of the dsDNA polymerization product formed from polymerization of the hairpin mixture comprising SEQ ID NO: 17 and SEQ ID NO: 18. In one embodiment, the hairpin mixture further includes ssDNA oligonucleotide having the sequence as set forth in SEQ ID NO: 22.

In a general method for forming the dsDNA molecule, the initiation or trigger ssDNA oligonucleotide and the combined DNA hairpin molecules are combined/mixed in physiological conditions which is sufficient to hybridize the oligonucleotides. The resulting DNA molecule can be a linear dsDNA polymeric molecule with 0, 1, or 2 periodic side groups consisting of the unhybridized ssDNA tails from the DNA hairpin molecules. Further, a branched polymeric molecule can be formed when a ssDNA-polymer conjugate is added to the existing linear dsDNA polymerization product. The physiological hybridization conditions for forming the dsDNA polymerization products are not particularly limited and are generally known to one skilled in the art.

In one embodiment, the dsDNA polymerization product is made up of hybridized monomers conjugated to a fluorescent molecule. In this embodiment, the dsDNA polymerization product can be directly detected using a method for detecting fluorescence. The method of detection is not particularly limited and these methods are generally known to one skilled in the art.

In one embodiment, one or more of the ssDNA oligonucleotides or hairpin DNA molecules is conjugated to a molecule. In one embodiment, a molecule is a detectable molecule. In one embodiment, a molecule is capable of forming a complex with a detectable molecule. In one embodiment, a molecule is a fluorescent molecule. In one embodiment, a molecule is a quantum dot. In one embodiment, a molecule is an antibody. In one embodiment, a molecule is biotin. In one embodiment, the fluorescent molecule is fluorescein. In one embodiment, a molecule is FAM (6-fluorescein amidite).

In one embodiment, one or more of the ssDNA oligonucleotides is conjugated to a molecule on the 5' end. In one embodiment, one or more of the ssDNA oligonucleotides is conjugated to a molecule on the 3' end. In one embodiment, SEQ ID NO: 16 is conjugated on the 3' end to FAM. In one embodiment, SEQ ID NO: 18 is conjugated on the 5' end to FAM. In various embodiments, one or more of SEQ ID NO:1, SEQ ID NO: 12 and SEQ ID NO: 13 are conjugated on the 5' end to Biotin.

In one embodiment, the polymerized dsDNA polymerization product is made up of hybridized monomers wherein one of the monomers comprises a direct linkage to a detectable molecule. In one embodiment, the polymerized dsDNA polymerization product is made up of hybridized monomers lacking a direct linkage to a detectable molecule. In one embodiment, an additional ssDNA oligonucleotide, having a region complementary to and capable of hybridization to a dsDNA polymerization product is provided, wherein the additional ssDNA oligonucleotide is directly linked to a detectable molecule. In one embodiment, the additional ssDNA oligonucleotide is linked to a molecule that can be used for detecting the dsDNA polymer. In one embodiment, the additional ssDNA oligonucleotide has a sequence selected from the group consisting of SEQ ID NO: 21 and SEQ ID NO: 22. In one embodiment, the additional ssDNA oligonucleotide is conjugated to biotin.

In one embodiment, an additional polymer consisting of a mixture of fluorescent and non-fluorescent monomers can be added to the system to facilitate detection of the dsDNA polymerization product. In one embodiment, the fluorescent polymer is capable of hybridization to one of the periodic ssDNA side groups extending from a dsDNA polymerization product. In one embodiment, an additional ssDNA oligonucleotide, having a region complementary to and capable of hybridization to a dsDNA polymerization product is conjugated to a polymeric fluorophore.

The invention includes one or more terminating ssDNA oligonucleotides. In one embodiment, the terminating ssDNA oligonucleotide is SEQ ID NO: 10. In one embodiment, the terminating ssDNA oligonucleotide is SEQ ID NO: 11. In one embodiment, the terminating ssDNA oligonucleotide has an additional region capable of hybridization to an extended side group of the dsDNA polymerization product which allows the terminating ssDNA to competitively depolymerize the polymerization product.

Detecting a Biomarker

Methods for detecting a desired biomarker comprise any method that determines the quantity or the presence of the biomarker either at the nucleic acid or protein level. Such methods are well known in the art and include but are not limited to western blots, northern blots, southern blots, ELISA, immunoprecipitation, immunofluorescence, flow cytometry, immunocytochemistry, nucleic acid hybridization techniques, nucleic acid reverse transcription methods, and nucleic acid amplification methods. In particular embodiments, dysregulation of a biomarker is detected on a protein level using, for example, antibodies that are directed against specific biomarker proteins. These antibodies can be used in various methods such as Western blot, ELISA, immunoprecipitation, or immunocytochemistry techniques.

The invention should not be limited to any one method of protein or nucleic acid detection method recited herein, but rather should encompass all known or heretofore unknown methods of detection as are, or become, known in the art.

In one embodiment, the invention includes detecting a marker in a cell preparation, wherein the cell preparation is a tissue sample from a patient and the biomarker is the presence of a protein. Detecting informative biomarkers is in particular performed on a cell preparation from a patient wherein presence of a biomarker is rare and the signal would require exponential amplification for detection.

In one embodiment, detecting a protein herein also informative biomarker, is performed such that the demands of an inexpensive and repeatable method for detection of multiple biomarkers in the same sample are met.

In one embodiment, detection of an informative biomarker is performed in a manner that minimally affects the state of the cell preparation, or patient sample.

Different types of biomarkers and their measurements can be combined in the compositions and methods of the present invention. In various embodiments, the protein form of the biomarkers is measured. In various embodiments, the nucleic acid form of the biomarkers is measured. In exemplary embodiments, the protein form is detected using an antibody.

When the antibody used in the methods of the invention is a polyclonal antibody (IgG), the antibody is generated by inoculating a suitable animal with a biomarker protein, peptide or a fragment thereof. Antibodies produced in the inoculated animal which specifically bind the biomarker protein are then isolated from fluid obtained from the animal. Biomarker antibodies may be generated in this manner in several non-human mammals such as, but not limited to goat, sheep, horse, rabbit, and donkey. Methods for generating polyclonal antibodies are well known in the art and are described, for example in Harlow, et al. (1998, In: Antibodies, A Laboratory Manual, Cold Spring Harbor, N.Y.).

When the antibody used in the methods of the invention is a monoclonal antibody, the antibody is generated using any well known monoclonal antibody preparation procedures such as those described, for example, in Harlow et al. (supra). Given that these methods are well known in the art, they are not replicated herein. Generally, monoclonal antibodies directed against a desired antigen are generated from mice immunized with the antigen using standard procedures as referenced herein. Monoclonal antibodies directed against full length or peptide fragments of biomarker may be prepared using the techniques described in Harlow, et al. (1998, In: Antibodies, A Laboratory Manual, Cold Spring Harbor, N.Y.).

Samples may need to be modified in order to render the biomarker antigens accessible to antibody binding. In a particular aspect of the immunocytochemistry methods, slides are transferred to a pretreatment buffer, for example phosphate buffered saline containing Triton-X. Incubating the sample in the pretreatment buffer rapidly disrupts the lipid bilayer of the cells and renders the antigens (i.e., biomarker proteins) more accessible for antibody binding. The pretreatment buffer may comprise a polymer, a detergent, or a nonionic or anionic surfactant such as, for example, an ethyloxylated anionic or nonionic surfactant, an alkanoate or an alkoxylate or even blends of these surfactants or even the use of a bile salt. The pretreatment buffers of the invention are used in methods for making antigens more accessible for antibody binding in an immunoassay, such as, for example, an immunocytochemistry method or an immunohistochemistry method.

Methods for detecting fluorescent molecules in a cell preparation are well known in the art. Such methods include but are not limited to detection using flow cytometry with or without flow associated cell sorting (FACS) and analysis, or fluorescent microscopy imaging.

Molecules of the present invention can be used for detection of nucleic acids. Such detection methods include: providing a sample, contacting at least one oligonucleotide of the present invention with the sample under conditions that allow hybridization of oligomer to nucleic acid molecules, and detecting one or more nucleic acid molecules of the sample that have hybridized to one or more oligomer of the present invention.

A sample can be from any source, and can be a biological sample, such as a sample from an organism or a group of organisms from the same or different species. A biological sample can be a sample of bodily fluid, for example, a blood sample, serum sample, lymph sample, a bone marrow sample, ascites fluid, pleural fluid, pelvic wash fluid, ocular fluid, urine, semen, sputum, or saliva. A biological sample can also be an extract from cutaneous, nasal, throat, or genital swabs, or extracts of fecal material. Biological samples can also be samples of organs or tissues, including tumors. Biological samples can also be samples of cell cultures, including both cell lines and primary cultures of both prokaryotic and eukaryotic cells.

A sample can be from the environment, such as from a body of water or from the soil, or from a food, beverage, or water source, an industrial source, workplace area, public area, or living area. A sample can be an extract, for example a liquid extract of a soil or food sample. A sample can be a solution made from washing or soaking, or suspending a swab from, articles such as tools, articles of clothing, artifacts, or other materials.

A sample can be an unprocessed or a processed sample; processing can involve steps that increase the purity, concentration, or accessibility of components of the sample to facilitate the analysis of the sample. As nonlimiting examples, processing can include steps that reduce the volume of a sample, remove or separate components of a sample, solubilize a sample or one or more sample components, or disrupt, modify, expose, release, or isolate components of a sample. Nonlimiting examples of such procedures are centrifugation, precipitation, filtration, homogenization, cell lysis, binding of antibodies, cell separation, etc. For example, in some embodiments of the present invention, the sample is a blood sample that is at least partially processed, for example, by the removal of red blood cells, by concentration, by selection of one or more cell or virus types (for example, white blood cells or pathogenic cells), or by lysis of cells, etc. In one embodiment, the method is useful for detecting biomolecules in cells that are immobilized on a hydrogel.

Exemplary samples include a solution of at least partially purified nucleic acid molecules. The nucleic acid molecules can be from a single source or multiple sources, and can comprise DNA, RNA, or both. For example, a solution of nucleic acid molecules can be a sample that was subjected to any of the steps of cell lysis, concentration, extraction, precipitation, nucleic acid selection (such as, for example, poly A RNA selection or selection of DNA sequences comprising Alu elements), or treatment with one or more enzymes. The sample can also be a solution that comprises synthetic nucleic acid molecules.

An oligomer or solid support of the present invention can be any oligomer format disclosed herein, or any oligomer comprising a monomer, dimer or non nucleic acid component (e.g., linker, fluorophore, quencher, stabilizing moiety) disclosed herein. An oligonucleotide analogue used in the methods of the present invention can be of any length and of any base composition, and can comprise one or more nucleic acid moieties, peptides, proteins lipids, carbohydrates, steroids, and other biochemical and chemical moieties. An oligonucleotide analogue of the present invention can be provided in solution or bound to a solid support.

Detection methods for bound nucleic acids are well known in the art, and can include the use of a detectable label that is attached to or incorporated into nucleic acid molecules of the survey population or that becomes bound to or incorporated into a hybridized target nucleic acid molecule or hybridized target nucleic acid molecule complex. Detectable labels for nucleic acid molecules are well-known in the art, and comprise fluorescent molecules such as fluorophores (including those set forth herein), radioisotopes, mass-altered chemical groups, specific binding members such as biotin that can be detected by signal-generating molecules, and the like. Detectable labels can also be incorporated into or attached to oligomer of the present invention, for example, in cases where sandwich hybridization using a signal oligomer is used for detection, or detection is performed using a specific binding member such as an antibody that recognizes oligomer/target nucleic acid molecule complexes. Solid supports can be scanned, exposed to film, visually inspected, etc. to determine the presence of a detectable label and thereby determine the binding of a target nucleic acid molecule to an oligomer immobilized on a solid support such as those of the invention.

In various embodiments of the methods of the invention, methods of measuring levels of one or more proteins of interest in a biological sample include, but are not limited to, an immuneochromatography assay, an immunodot assay, a Luminex assay, an ELISA assay, an ELISPOT assay, a protein microarray assay, a Western blot assay, a mass spectrophotometry assay, a radioimmunoassay (RIA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Molecularly Regulated Reversible DNA Polymerization

Synthetic polymers are broadly used in various applications such as medicine, cloth, devices, and tools. However, their synthesis and decomposition usually require harsh conditions (e.g., high temperature or organic solvent). In contrast, natural polymers only need mild physiological conditions for synthesis and decomposition. A typical example is protein synthesis and hydrolysis in a living cell. Great efforts have therefore been made to emulate nature in synthesizing dynamic polymers with reversibility (Lehn, Science. 1985, 227:849-856; Rowan et al., Angew Chem Int Ed Engl. 2002, 41:898-952; Brunsveld et al, Chem Rev. 2001, 101:4071-4079). Dynamic polymers can be synthesized with covalent bonds and non-covalent interactions that can be reversed via diverse mechanisms (Lehn, Prog. Polym. Sci. 2005, 30:814-831). For instance, units of 2-ureido-4-pyrimidone can form a self-complementary array of four hydrogen bonds for synthesis of unidirectional reversible polymers (Sijbesma et al., Science. 1997, 278:1601-1604). While great progress has been made in developing these elegant polymers for various potential applications, it remains challenging to develop biocompatible polymers whose synthesis and reversibility are strictly realized in physiological conditions and are well controlled at the biomolecular level (Oshovsky et al., Angew Chem Int Ed Engl. 2007, 46:2366-2393).

Nucleic acids have been recently used as biocompatible macromonomers to synthesize supramolecular polymers (Seeman, Nature. 2003, 421:427-431). Precise hybridization of nucleic acids can enable the organization and conversion of nucleic acid macromonomers into delicate two-dimensional and three-dimensional supramolecular architectures for promising biological and biomedical applications (Rothemund, Nature. 2006, 440:297-302). For instance, the Pierce group has created a hybridization chain reaction method to synthesize DNA polymers for molecular sensing (Dirks and Pierce, Proc Natl Acad Sci USA. 2004, 101: 15275-15278). However, little attention has been paid to apply DNA macromonomers for the synthesis of polymers whose reversibility can be molecularly regulated in physiological conditions. Nucleic acid hybridization can be precisely controlled through strand displacement interactions (Lee et al., J Mol Biol. 1970, 48:1-22; Wetmur and Davidson, J Mol Biol. 1968, 31:349-370; Yurke et al., Nature. 2000, 406:605-608; Bath and Turberfield, Nat Nanotechnol. 2007, 2:275-284). The findings disclosed herein demonstrate dynamic linear and branched DNA polymers with molecularly regulated reversibility that can be regulated in physiological conditions at the biomolecular level.

Principle of Reversibility

Figures 2A, 2B:
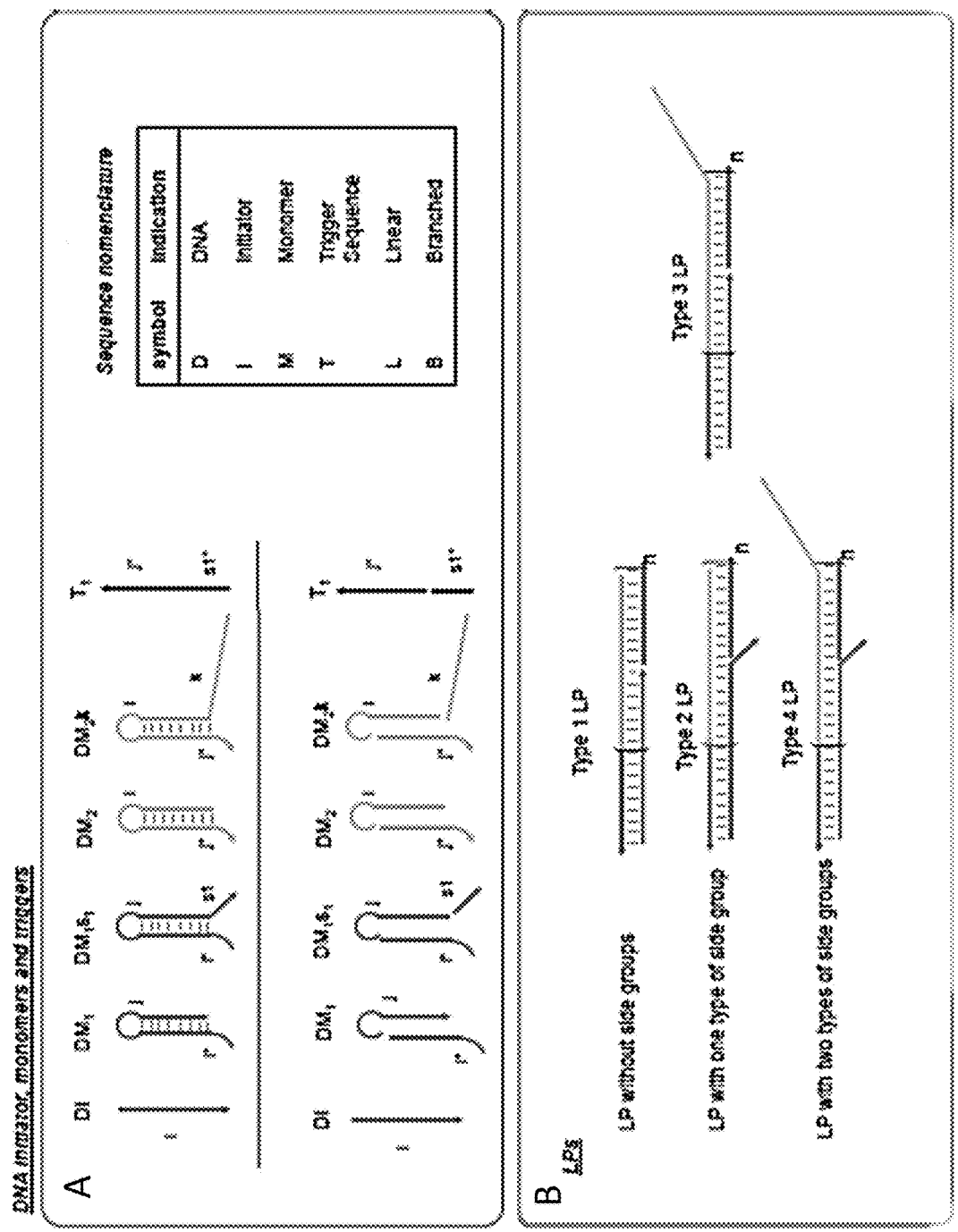
FIG. 2A and FIG. 2B, depicts the nomenclatures and secondary structures of individual DNA sequences and formed polymers. The upper panel of FIG. 2A depicts a schematic diagram of the secondary structures of DNA initiator, hybridization monomers and triggering sequence. The lower panel of FIG. 2A depicts a schematic diagram of the different sequence domains that make up each DNA molecule.
Figures 3A, 3B:
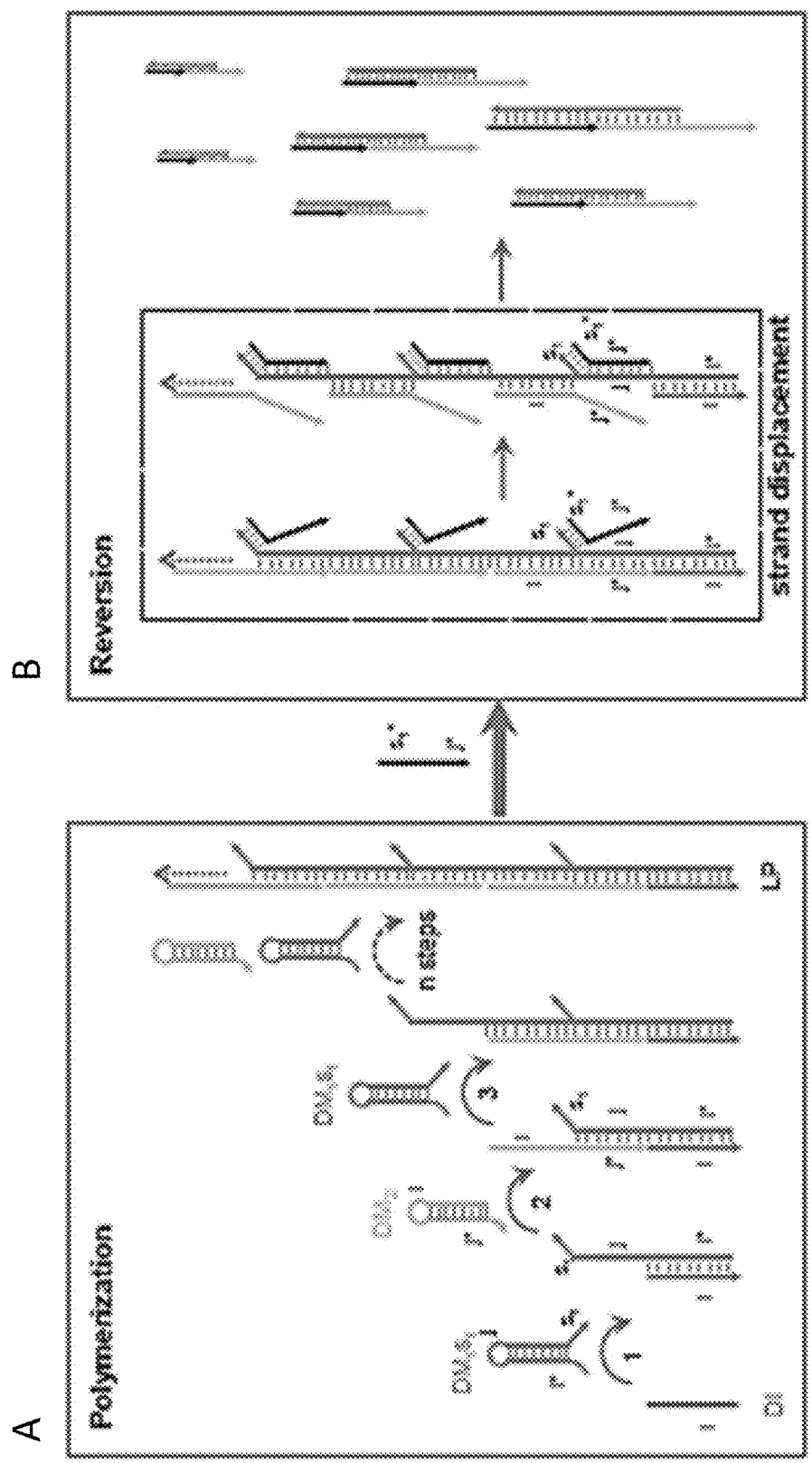
FIG. 3A and FIG. 3B, depicts a step-wise schematic diagram of LP polymerization and depolymerization via the introduction of a triggering sequence (as shown between panels).

The synthesis of a linear polymer (LP, FIG. 1A, upper panel) involves three molecules including a DNA initiator (DI) and two DNA monomers (DMs). DI is a linear structure with one functional domain, as labeled with i (FIG. 1B and FIG. 2A). The DMs are hairpin-forming oligonucelotides. DM1s1 has three domains including i*, j and s1; and DM2 has two domains including j* and i. During polymerization (FIG. 2A), DI opens the hairpin structure of DM1s1 to form an i-i* double helix with j and s1 left as a linear segment. The linear j domain further reacts with the j* domain of DM2 to form a j-j* double helix and a linear segment i. The linear i segment functions as a new initiator to induce the reactions of DM1s1 and DM2 in new cycles for the synthesis of a LP. Notably, the domain s1 of DM1s1 does not participate in the linear polymerization and is a functional side group of LP. Thus, s1 can hybridize with a molecule carrying a complementary sequence domain s1* (FIG. 1B and FIG. 3B). The molecular trigger T1 has two functional domains including s1* and j*. With the aid of s1-s1* and j-j* hybridization, T1 hybridizes with the DM1s1 unit of LP and displaces DM2 (FIG. 1B and FIG. 3B). Resultantly, LP is reversed without the involvement of any non-physiological factors.

Alternatively, DM2 may contain a functional side group (named as DM2k, FIG. 2A) to bear a total of three domains including j*, i and k. Through polymerization of DM1s1 and DM2k, LP acquires two functional side groups, s1 and k (FIG. 2B).

The side group k functions as a hybridization region for an additional polymer-ssDNA conjugate. Resultantly, a branched polymer (BP) is synthesized with LP and ssDNA-polymer conjugates (FIG. 1A, lower panel). Because DM1s1 has the side groups, i.e., s1, which does not participate in the polymerization, a corresponding molecular trigger T1 is required to induce the reversible polymerization of BP (FIG. 1A-B).

The materials and methods are now described.

Materials and Methods

Materials and Chemicals

Phosphate buffered saline (PBS), Tris-EDTA and agarose were purchased from Fisher Scientific (Suwanee, Ga.). All the oligonucleotides (Table 51) were purified by HPLC or desalting and purchased from Integrated DNA Technologies (Coralville, Iowa). The streptavidin-coated microparticles (average diameter: 5 μm) was obtained from Spherotech (Lake Forest, Ill.). The DNA marker, SYBR-Safe, Cell-Tracker™ Blue CMAC dye, bovine serum albumin (BSA), human dermal fibroblasts, neonatal (HDFns) and cell culture reagents were purchased from Invitrogen (Carlsbad, Calif.). Ultracentrifugal filter (100K cut-off size) and biotinylated anti-collagen IgG and IgG isotype were purchased from Millipore (Billerica, Mass.) and SouthernBiotech (Birmingham, Ala.) respectively. N,N-diisopropylethylamine was obtained from Thermo Fisher Scientific (Waltham, Mass.). All other chemicals, such as (3-aminopropyl) triethoxysilane (APTES) and fluorescamine, were obtained from Sigma-Aldrich (Louis, Mo.). Antibodies were purchased from Santa Cruz Biotechnology, Inc. (Dallas, Tex.). Mica was purchased from Asheville-Schoonmaker Mica Company (Newport News, Va.). Atomic force microscope (AFM) cantilever (SCANASYST-FLUID+) was purchased from Bruker (Camarilla, Calif.).

DNA Hybridization Reactions in Aqueous Solution

DNA sequences were designed using NUPACK server (www.nupack.org). The secondary structures of the DNA sequences were also predicted using NUPACK. Before any DNA hybridization reactions, the oligonucleotides were diluted in PBS to their predetermined concentrations and heated to 95° C. and then cooled to room temperature for 1 h. To synthesize the linear DNA polymers, DI and two DMs were prepared three times higher than their final concentrations and were mixed together after annealing at room temperature overnight. To prepare annealed DNA samples, individual DNA sequences with their concentrations the same as that used in depolymerization were mixed together and heated to 95° C. and then cooled to room temperature gradually for 130 min before use.

Delta G Studies of the DNA Hybridization Reactions

Delta G of two hybridized DNA sequences was calculated using IDT OligoAnalyzer 3.1 (https://www.idtdna.com/calc/analyzer) under the condition of 0.25 μM of DNA and 140 mM Na+.

Gel Electrophoresis

Prepared DNA samples were loaded into the wells of 1% agarose gel or 10% polyacrlyamide gel (Tris-borate-EDTA buffer, 89 mM boric acid, 2 mM EDTA, pH 8.2). The agarose gel was pre-stained with SYBR-Safe (0.1 μL of stock solution per mL of agarose gel) and the polyacrylamide gel was post-stained with SYBR-Safe (5 μL of stock solution in 30 mL TBE buffer). The gel electrophoresis was run at 100 V for 60 min and the gels were imaged using a CRI Maestro EX System (Woburn, Mass.) with a blue exciting light (455 nm). The fluorecence of DNA in gels were recorded with a blue filter (Em>488 nm) and the detailed quantification methods were described in corresponding figure captions.

Kinetics of DNA Polymerization and Depolymerization

The polymerization and depolymerization products were prepared similarly as detailed above. The reactions were processed for different periods of time and immediately loaded with glycerol and subjected to gel electrophoresis. For the kinetics of polymerization profile, the percentage of unreacted DMs was normalized to that of control group without DI by measuring their fluorescence intensities with Maestro software. The conversion of DMs was calculated using this formula: CDM %=100%-FDM %, where the CDM is the converted DMs and FDM is the free DMs remained unreacted. For the kinetics of depolymerization profile, the DNA polymers left were normalized to that of control group (it was treated without the reversing sequence) by measuring their fluorescence intensities with Maestro software.

DNA Hybridization Reactions on Microparticle Surface

Streptavidin-coated microparticles (0.1 mg) were mixed with biotinylated DI (50 nM) in 20 µL of reaction buffer (PBS, 0.1% v/v Tween 20, 0.02% w/v NaN3) at room temperature for 1 h on a rotator. To assemble linear DNA polymers on particles, they were incubated in 20 µL of reaction buffer containing two DMs (0.5 µM) at room temperature overnight on a rotator. To assemble branched DNA polymers on particles, the secondary set of DMs (1 µM) was reacted with particles with linear DNA polymers for another ~12 h. To depolymerize the DNA polymers on the particle surface, reversing sequences were added and the reaction took for 1 h. The particles were washed via centrifugation (10,000×g for 8 min, twice) after each DNA assembly or disassembly step. Particle suspensions were then dropped on a Teflon-coated glass slide and imaged using Maestro system with a blue light (Ex, 455 nm) and a blue filter (Em>488 nm). The droplets were also examined using guava easyCyte™ flow cytometer (Millipore) with a blue light (Ex, 488 nm) and a green filter (Em, 525±30 nm). The results were post analyzed using FlowJo software and the geometric means were used to represent the mean fluorescence intensity.

Atomic Force Microscope (AFM) Imaging

Mica was modified to bear positive charges on its surface before use. Briefly, mica with a dimension of ~1.5 cm in square and was cut into an octagon shape and freshly cleaved using a clean razor blade with a thickness of 0.1 mm. The mica was hung with a metal clip on its edge on a glass rod in a desiccator, which was filled with argon gas. Two eppendorf caps were placed on the bottom of the desiccator to hold 90 µL of APTES and 30 µL of DIPEA. Care was taken to ensure an argon atmosphere in the desiccator. The mica in the desiccator was reacted for 2 h with the evaporated chemicals. Then the desiccator was purged with argon gas for 2 min and the mica was cured in the desiccator for another 1 or 2 days before use.

DNA samples were diluted in TE buffer (20 mM Tris-HCl, 1 mM EDTA and 200 mM NaCl) to a concentration of ~0.3 ng/µL before any AFM studies. 50 µL of diluted DNA samples were deposited on the modified mica for 2 min to allow the DNA to adsorb on the modified mica surface. Additional 40 µL TE buffer was added to fill the gap between the mica and AFM cantilever. Silicon tips, SCANASYST-FLUID+(tip radius: ~2 nm; resonance frequency: ~150 kHz; spring constant: ~0.7 N/m; length: 70 µm; width: 10 µm) were used for all AFM experiments. AFM images were taken using Dimension Icon (Bruker) in Peak Force Tapping mode in fluid. The scan rate was 1 Hz with 512 pixels per line. The scan size was always set to 2 µm first and then 1 µm. The image data were flattened using NanoScope Analysis (1.4 version). To determine the DNA contour length in the AFM images, ImageJ was used and only molecules that were entirely imaged in the scan area were measured and the overlapping molecules were excluded. For each sample, fifty measurements were recorded on the image of which the scan size is 1 µm.

Bidirectional DNA Polymerization on Cells

Collagen type I expressed by HDFns was used as the target for signal amplification tests. HDFns were cultured in medium 106 (M106) fortified with recommended low serum growth supplement, gentamicin (10 µg/mL) and amphotericin B (0.25 µg/mL) at 37° C. with 5% CO2. Cells between passage 2~4 were used in all experiments. Cells were seeded into 8-well chamber slide (ibidi) and used at approximately 80% confluence. Cells were immunostained using standard procedures. Briefly, cells were pre-stained with CMAC dye (5 µM) in PBS for 0.5 h and then incubate in M106 for another 0.5 h at 37° C. After washing, cells were blocked with binding buffer (M106 with 2% w/v BSA) for 0.5 h at 37° C. and stained with biotinylated primary antibody (20 µg/mL in binding buffer) for 1 h at 37° C. After washing with M106, they were then treated with streptavidin (10 µg/mL in binding buffer) for 45 min at 37° C. and then biotinylated DIL (1 µM in M106) for 45 min at 25° C. Finally they were treated with FAM-labeled/unlabeled DMs (1 µM for linear DNA polymerization and 2.5 µM for branched DNA polymerization) and reversing sequences (2 µM of RL with/without 5 µM of RB) for 1 h respectively at 25° C. Cells in the chamber slide were imaged using a laser scanning confocal microscope (Olympus FV1000) equipped with FV10-ASW 3.0 software and 60×(PlanApo) oil objectives. CMAC were excited with violet laser (405 nm) and FAM was excited with Blue Argon (488 nm). Images over z axis were recorded for each sample and the projection image over z axis were presented and analyzed. The green fluorescence intensity of each sample (at least four images) was quantified using ImageJ software.

The results of the experiments are now described.

DNA Polymerization Components

FIG. 2A schematically demonstrates a variety of hairpin (heretofore designated as DM) structures that when combined with an initiating oligonucleotide (heretofore designated as DI) would lead to the formation of different forms of dsDNA polymers (heretofore designated LP for linear dsDNA polymers). FIG. 2A also schematically demonstrates a terminating ssDNA molecule (heretofore designated as T) that when combined with LP reverse the polymerization. Throughout, specific sub-regions of each DNA oligonucleotide are referred to as designated in FIG. 2A.

Polymerization of DNA Macromonomers.

Figure 4:
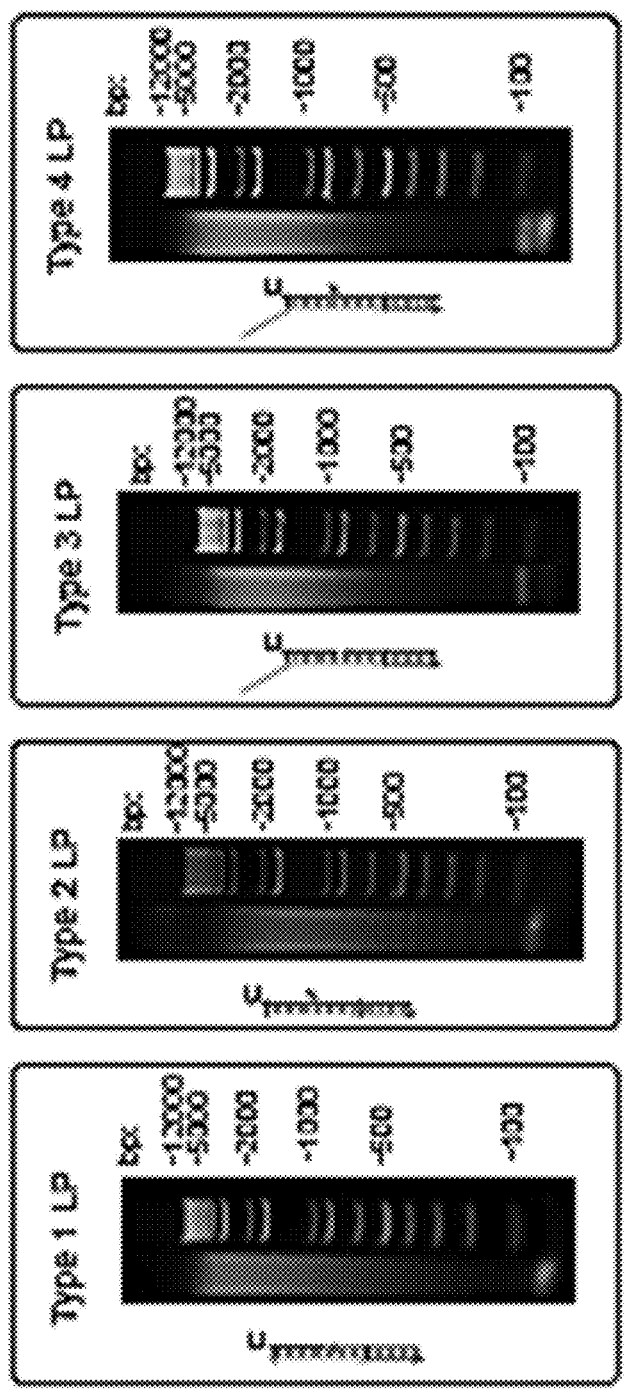
FIG. 4 depicts the results from gel electrophoresis of various LPs as indicated by type (see FIG. 2B) and by schematic diagram.
Figures 5A, 5B, 5C, 5D:
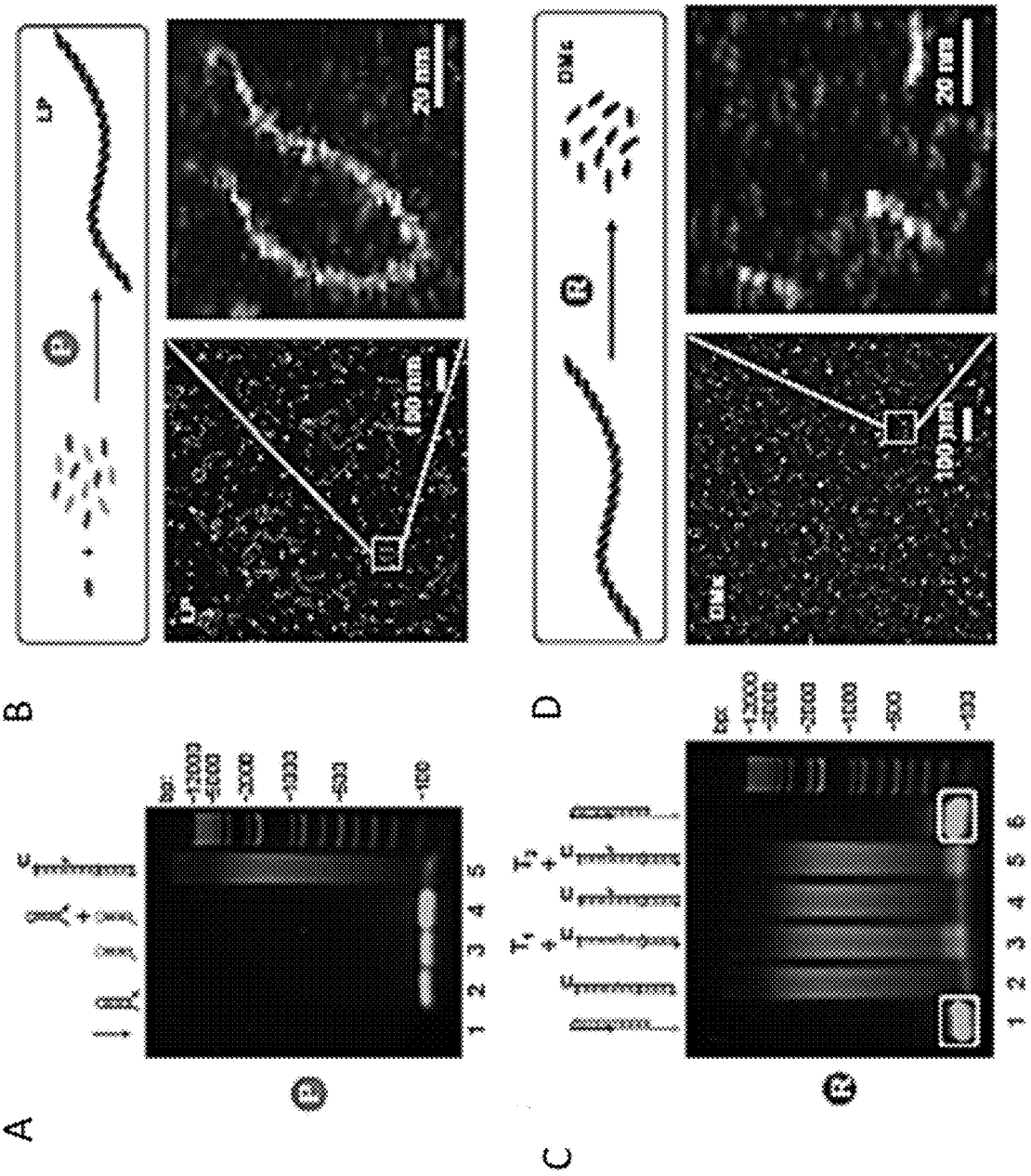
FIG. 5A through FIG. 5D, is a series of images characterizing the reversibility of LP (with s1 side groups).

Four representative LPs were synthesized and characterized using gel electrophoresis (FIG. 4). The results showed that DMs formed LPs in the presence of DI. Side groups did not apparently influence the LP formation. The apparent molecular weights of LPs mostly fell in the range between 500 to 3,000 bp. In contrast, DMs did not form LPs in the absence of DI (FIG. 5A, lane 4). The successful synthesis of LPs was also confirmed using AFM (FIG. 5B).

Examination of LP Reversibility.

Figure 6:
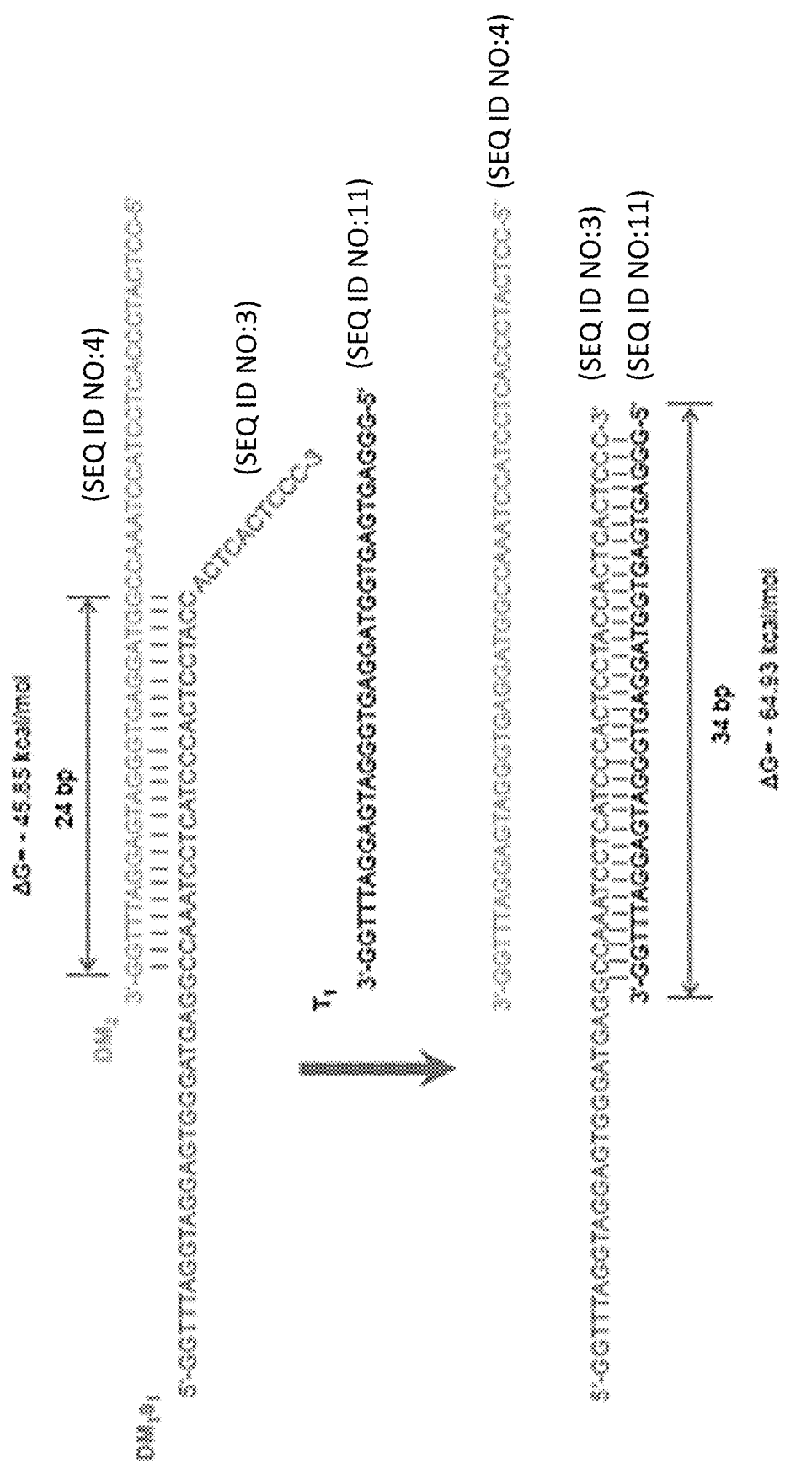
FIG. 6 depicts a linear model of the sequences and secondary structures of DM1s1, DM2, T1 and their hybridized complexes that illustrate the T1-triggered LP reversing.

The side group s1 had 10 nucleotides (nt). When it was incorporated into the 3' end of DM1, the formed LP had periodic side functional groups (FIG. 3A). T1 had 34 nt with 10 nt complementary to s1 and another 24 nt complementary to the j domain of DM1s1. When T1 and DM1s1 hybridize (FIG. 6), the formed double-stranded helix has 34 base pairs (bp). By contrast, DM2 and DM1s1 have a helix of 24 bp. The former is thermodynamically more stable than the latter one. Thus, T1 is more competitive than DM2 in hybridization with DM1s1.

As shown in the gel electrophoresis image (FIG. 5C), the LPs bearing the s1 groups virtually disappeared after reacting with T1 (lane 6). The major reaction products (lane 6) were located in the same position as the hybridization complex of DM1s1, DM2, and T1 (lane 1). By comparison, the LP bands were not affected after mixed with the control triggering sequence T2 (lanes 4 and 5). When LPs bearing no s1 groups were treated with T1, LPs barely changed (lanes 2 and 3). These results clearly demonstrate that T1 effectively triggered LP reverse in a sequence-specific and s1-dependent manner.

The gel electrophoresis results were confirmed by AFM analysis. The morphologies of LPs with s1 side groups after polymerization and reverse were shown in FIG. 5B and FIG. 5D.

Figures 7A, 7B, 7C:
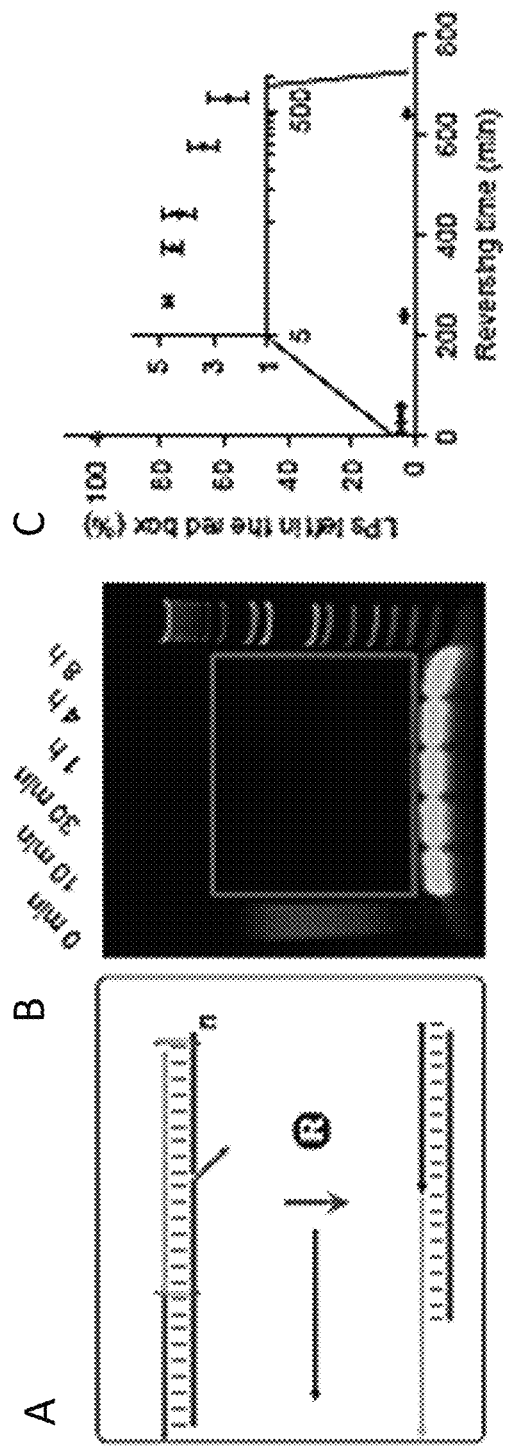
FIG. 7A through FIG. 7C, depicts the effect of reversing time on LP depolymerization.
Figures 8A, 8B, 8C:
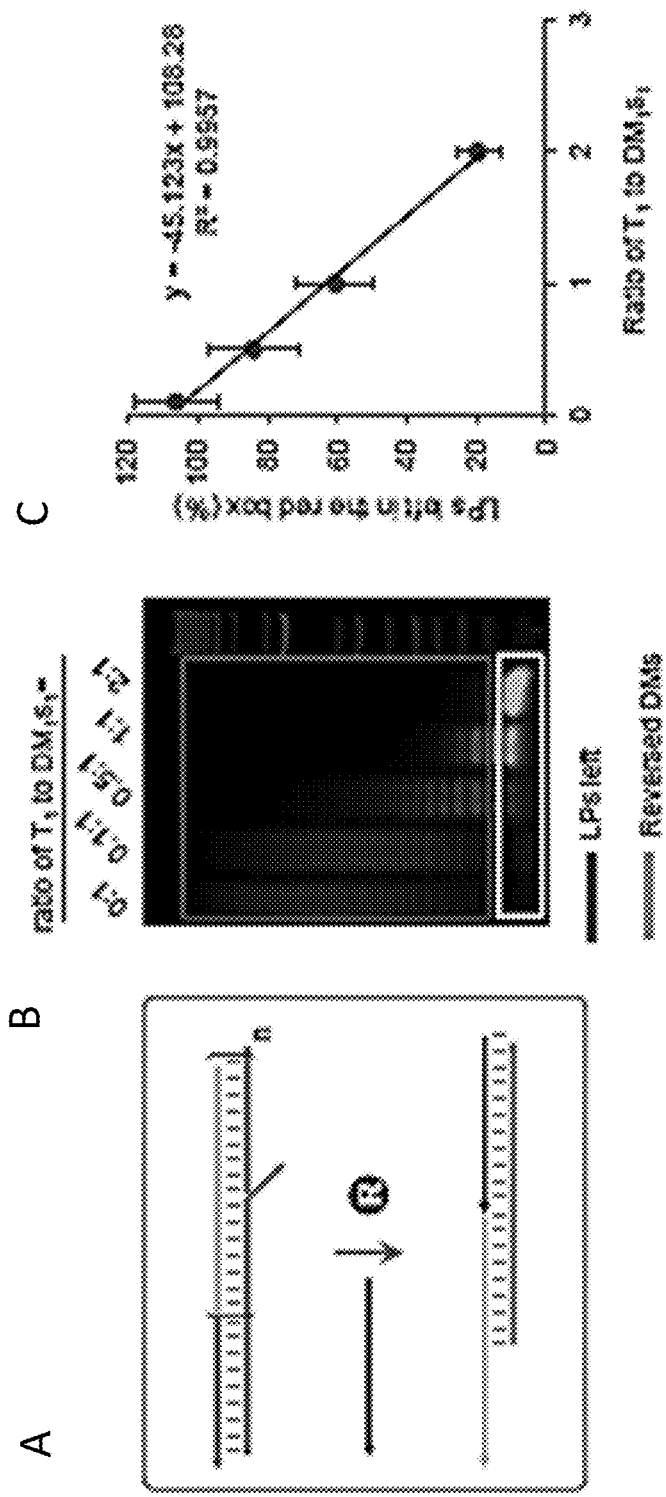
FIG. 8A through FIG. 8C, depicts the effect of T1 and DM1s1 ratio on LP reversing.

The effects of three different hybridization parameters on the reverse reaction were also studied. The reverse time was varied from 10 min to 8 h (FIG. 7). The result showed that 95% LPs disappeared within 10 min, suggesting that reverse reaction was fast. The reverse efficiency increased with the increasing molar ratio of T1 to DM1s1 (FIG. 8). Notably, the reverse efficiency was linearly correlated with the molar ratio. It suggests that reverse reaction can be well controlled using a predetermined amount of T1.

Synthesis of BP Using LP and Two DMs.

Figure 9:
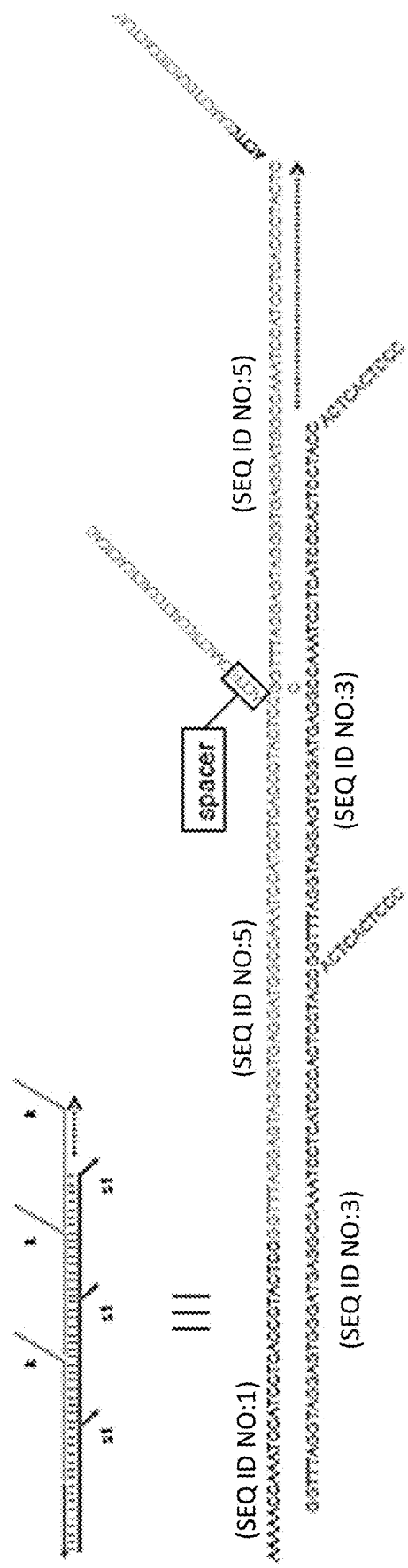
FIG. 9 depicts a schematic diagram and linear model of the secondary structure and sequence of the polymerized LP with s1 and k side groups.

BP was synthesized using purified LP and a ssDNA-polymer conjugate synthesized using ATRP reaction. LP had two side groups, s1 and k (FIG. 9). The side group k had 29 nt. The 5 nt adjacent to the backbone of LP were designed as a spacer to mitigate potential steric hindrance for the formation of side chains. The other 24 nt were used as a hybridization region for the ssDNA attached to the ATRP polymer.

Reversibility of LP and BP on Particle and the Extracellular Matrix

Figures 10A, 10B:
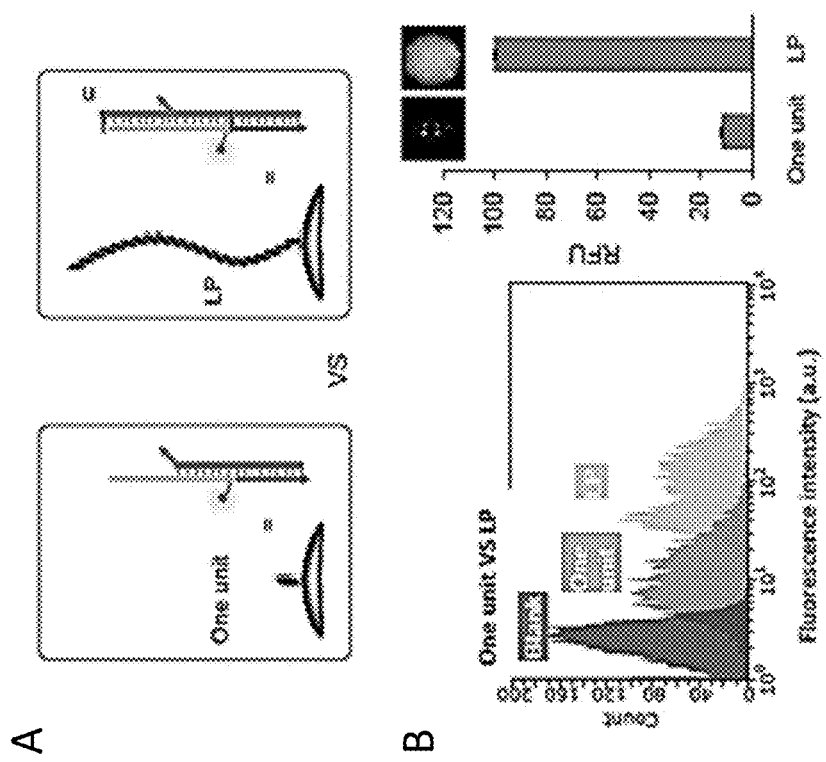
FIG. 10A and FIG. 10B, depicts LP formation on microparticle surface when DM2 was labeled with fluorophore at the 3' end.

Reversible DNA polymerization on a microparticle surface was evaluated using microparticles with an average diameter of 5 μm, functionalized with DI. DM2 was labeled with fluorophore for examination of LP synthesis. The flow cytometry analysis showed that the average fluorescence intensity of microparticles with LP was 8.5 times stronger than that of control particles with DM1 hybridizing with one DM2 (FIG. 10), which was consistent with the fluorescence measurement of the microparticle suspension.

Figures 11A, 11B:
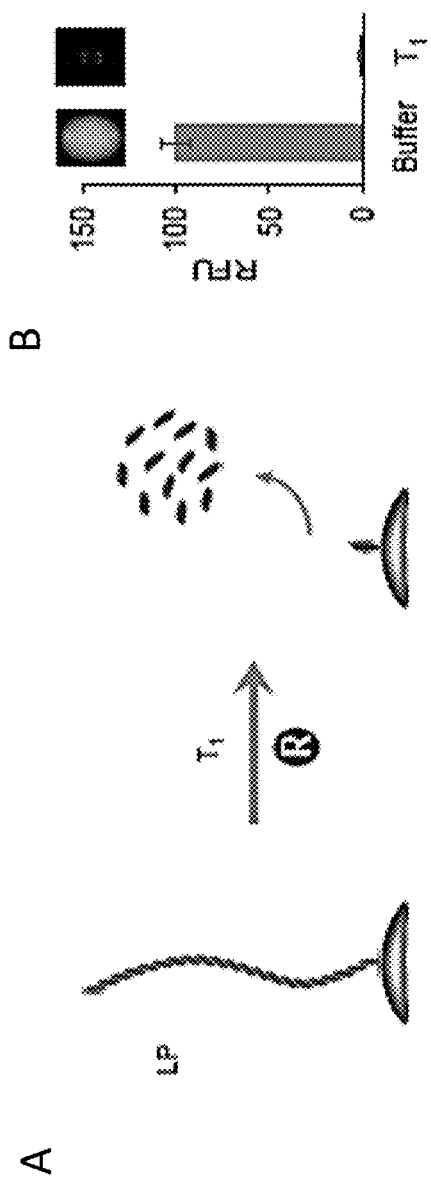
FIG. 11A and FIG. 11B, depicts fluorescent LP reversing on microparticle surface.

Microparticles bearing LP were treated with T1. The fluorescence intensity analysis (FIG. 11B) show that T1 treatment reduced fluorescence intensity compared to buffer-treated microparticles. These data demonstrate that LP was specifically reversed on the microparticle surface.

Figures 12A, 12B:
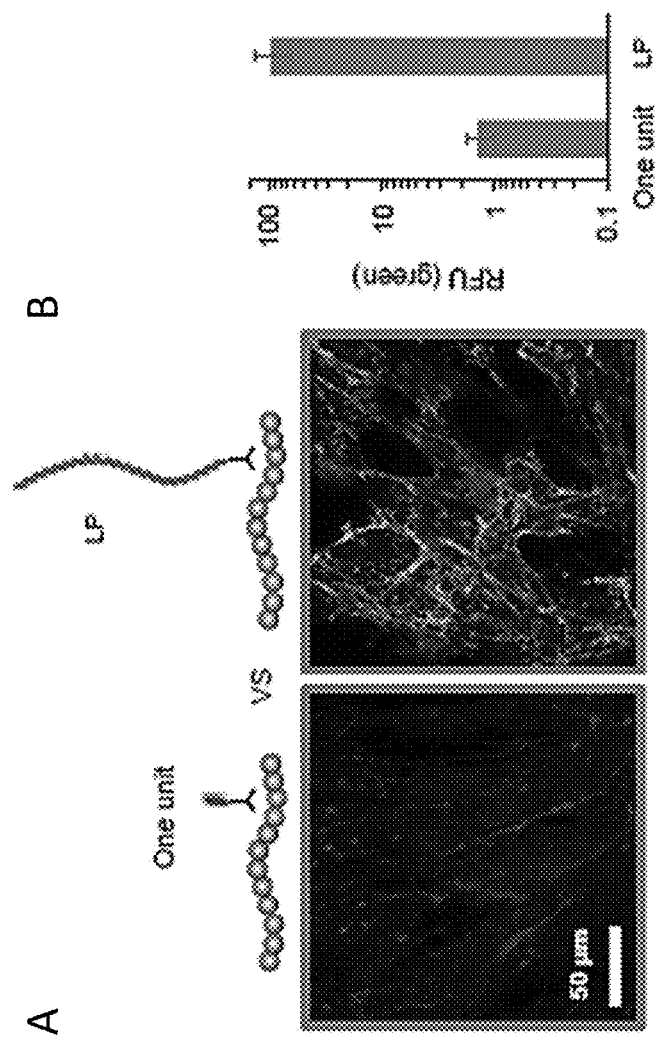
FIG. 12A and FIG. 12B, depicts fluorescent LP formation on a cell surface.

In addition to microparticles, the extracellular matrix (ECM) of living cells was used as a substrate to study LP. Fibroblast and collagen type I were used as a model. DI was conjugated to the anti-collagen antibody via the biotin-streptavidin interaction. After cells were treated with the antibody-DI conjugate, they were washed and further treated with a mixture of DM1 and DM2. The results showed that the conjugate induced the formation of LP on the ECM (FIG. 12).

Figures 13A, 13B, 13C:
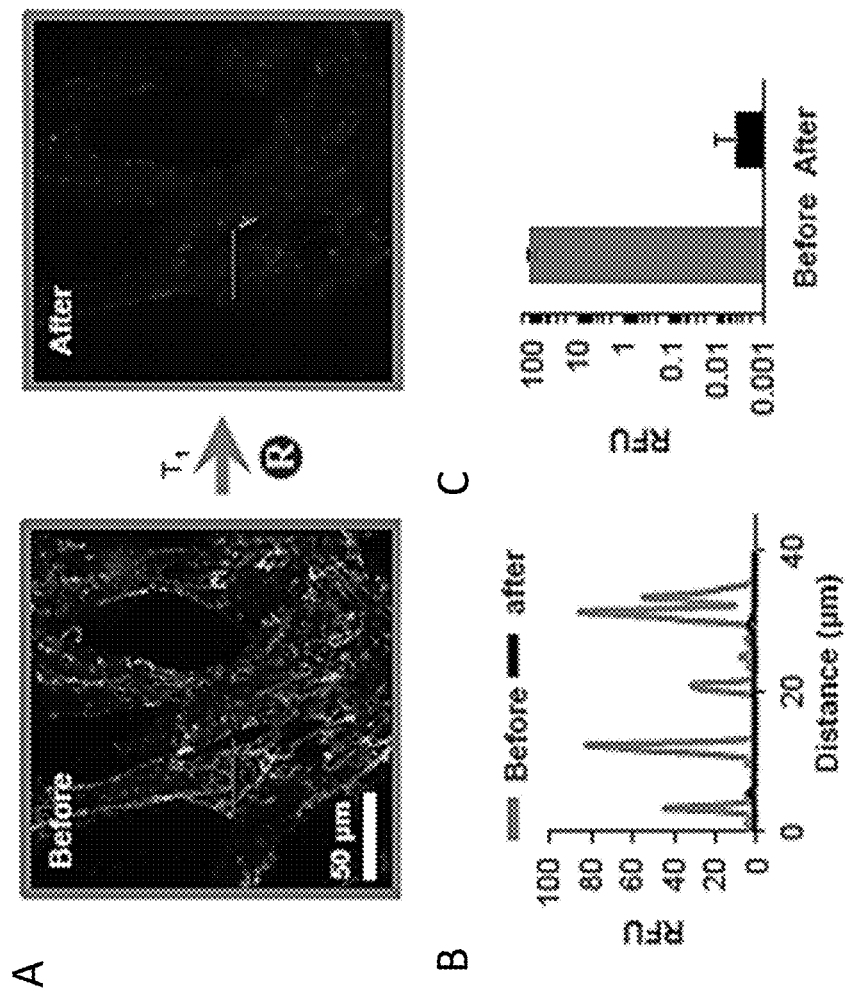
FIG. 13A through FIG. 13C, depicts LP reversal on cells using triggering sequence (T1).
Figure 14:
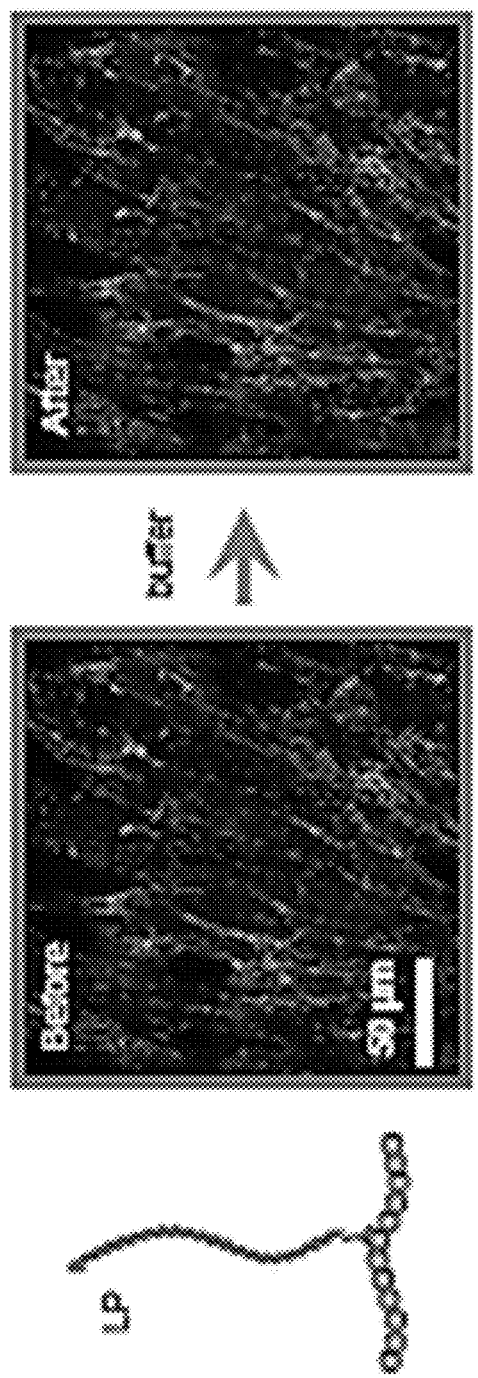
FIG. 14 depicts fluorescent LP before and after the addition of buffer alone, without the addition of T1.

The reversibility of LP on the ECM of living cells was also examined. When the triggering solutions were used to treat the ECM, the fluorescence signals disappeared (FIG. 13). In the control groups, washing with the control buffer did not cause the significant change of the ECM fluorescence intensity (FIG. 14). It is also important to note that the different locations of the ECM exhibited different fluorescence intensities, which suggests the heterogeneous distribution of collagen I on the ECM. Despite this heterogeneity, all locations of the ECM virtually exhibited the same fluorescence intensity as the background after the triggering treatment. It further confirms that the reversibility of LP on the ECM of the living cells could be effectively realized.

Example 2: Development of an Enhanced DNA-Based Reversible Signal Amplification Method Using DNA Polymers, Polymeric Fluorophores and Molecular Triggers The gold standard method for whole-cell protein analysis is to stain a protein with an antibody that can only be conjugated with a few fluorophores; otherwise, the antibody will lose its binding ability. In the method presented herein, each antibody carries a DNA polymer, in which each unit bears a polymeric fluorophore. Thus, each protein will be stained by m fluorophores multiplied by n units via DNA polymerization and hybridization. This new method decouples protein recognition from fluorophore display. Fluorophores are removed from a cell sample via disassembly of DNA polymers using molecular triggers regardless of strong antibody-antigen interactions. Notably, trigger-mediated polymer disassembly is carried out in physiological conditions without any harsh conditions. Since the polymerization for protein detection is reversible, a sample can be reiteratively examined for a variety of different proteins without the problem of spectral overlap, which is often an inevitable challenge to conventional protein staining methods.

The materials and methods are now described.

Materials and Methods 4,7,10-Trioxa-1,13-tridecanediamine (TDA), triethylamine (TEA), trifluoroacetic acid (TFA), di-tert-butyl dicarbonate (DiBoc), methacryloyl chloride, 2-Bromoisobutanoic acid N-hydroxysuccinimide ester (BIBB-NHS), triethylene glycol methyl ether methacrylate (TEGMA), 1,1,4,7,10,10-Hexamethyltriethylenetetramine (HMTETA), copper(I) chloride, copper(II) sulfate, fluorescein 5(6)-isothiocyanate (FITC), were purchased from Sigma-Aldrich and used as received. DNAs were purchased from Integrated DNA Technologies (IDT) and used as received.

Figure 15:
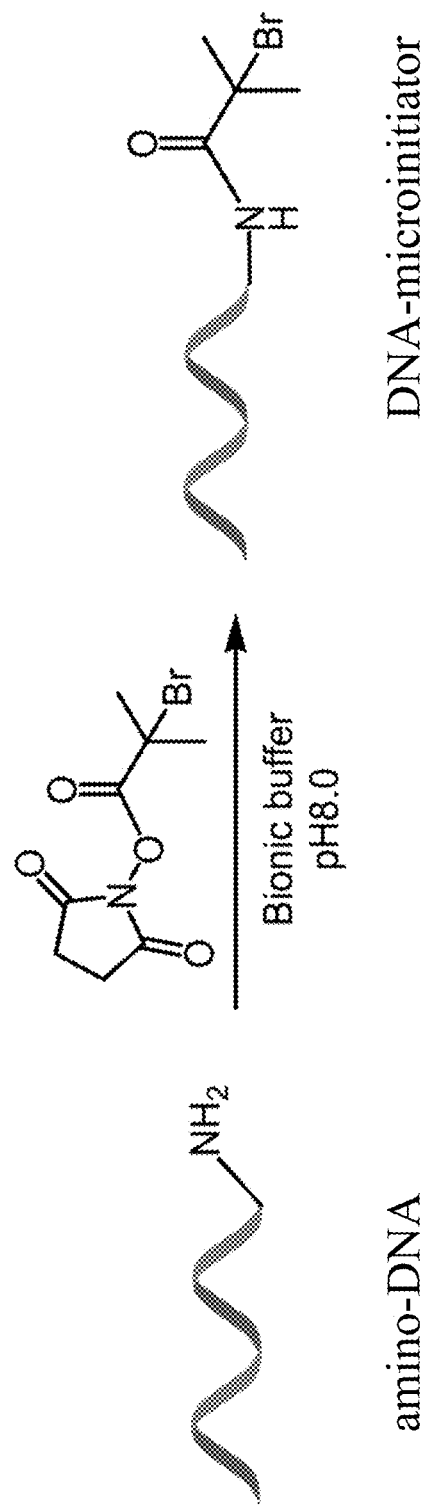
FIG. 15 depicts a diagram of the synthesis of the DNA-microinitiator.

Synthesis of DNA-Microinitiator (FIG. 15)

A solution of amino-DNA (100 nmol) in 100 μL bionic buffer was added 4 of BIBB-NHS solution in DMSO (1 μmol). The mixture was vortexed at room temperature for 4 h. Thereafter, another 4 μL of BIBB-NHS solution was added to the reaction and the mixture was further vortexed overnight at room temperature. After reaction, the DNA-microinitiator was collected using a spin filter and was washed with PBS for several times to remove the unreacted small organic initiator.

Figure 16:
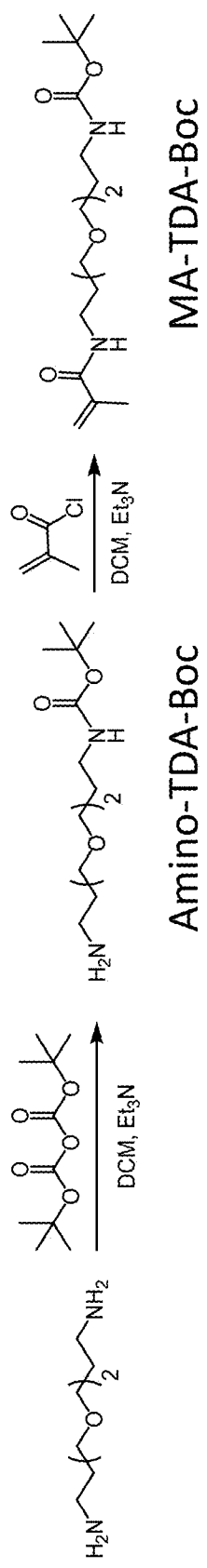
FIG. 16 depicts a diagram of the synthesis of the monomer for formation of DNA-fluorescent polymer conjugates.

Synthesis of Monomer (FIG. 16):

A solution of TDA (4.4 g, 20 mmol) and TEA (1.01 g, 10 mmol) in 45 mL dry DCM at 0° C. was added dropwise a solution of DiBoc (1.09 g, 0.5 mmol) in 5 mL dry DCM. The reaction was stirred under Argon at 0° C. for 30 min and further at room temperature overnight. Thereafter, the reaction was diluted by adding 50 mL water. The organic layer was separated and the water layer was extracted with DCM (2×15 mL). The combined organic layer was washed with saturated $NaHCO_3$ and brine, dried over MgSO4, filtered and concentrated in vacuum to obtain the crude product Amino-TDA-Boc, which was used for next step without further purification.

A solution of Amino-TDA-Boc (0.32 g, 1 mmol) and TEA (0.202 g, 2 mmol) in 20 mL dry DCM at 0° C. was added dropwise a solution of methacryloyl chloride (0.104 g, 1 mmol) in 2 mL dry DCM. The reaction was stirred under Argon at 0° C. for 30 min and further at room temperature for 2 h. Thereafter, the reaction was quenched by addition of 1 mL saturated ammonium chloride. The solution was further diluted by adding 20 mL water. The organic layer was separated and washed with 0.1 M HCl, saturated $NaHCO_3$ and brine, dried over $MgSO_4$, filtered and concentrated in vacuum, purified via silica gel column (EtOAc) to obtain the monomer MA-TDA-Boc.

Figure 17:
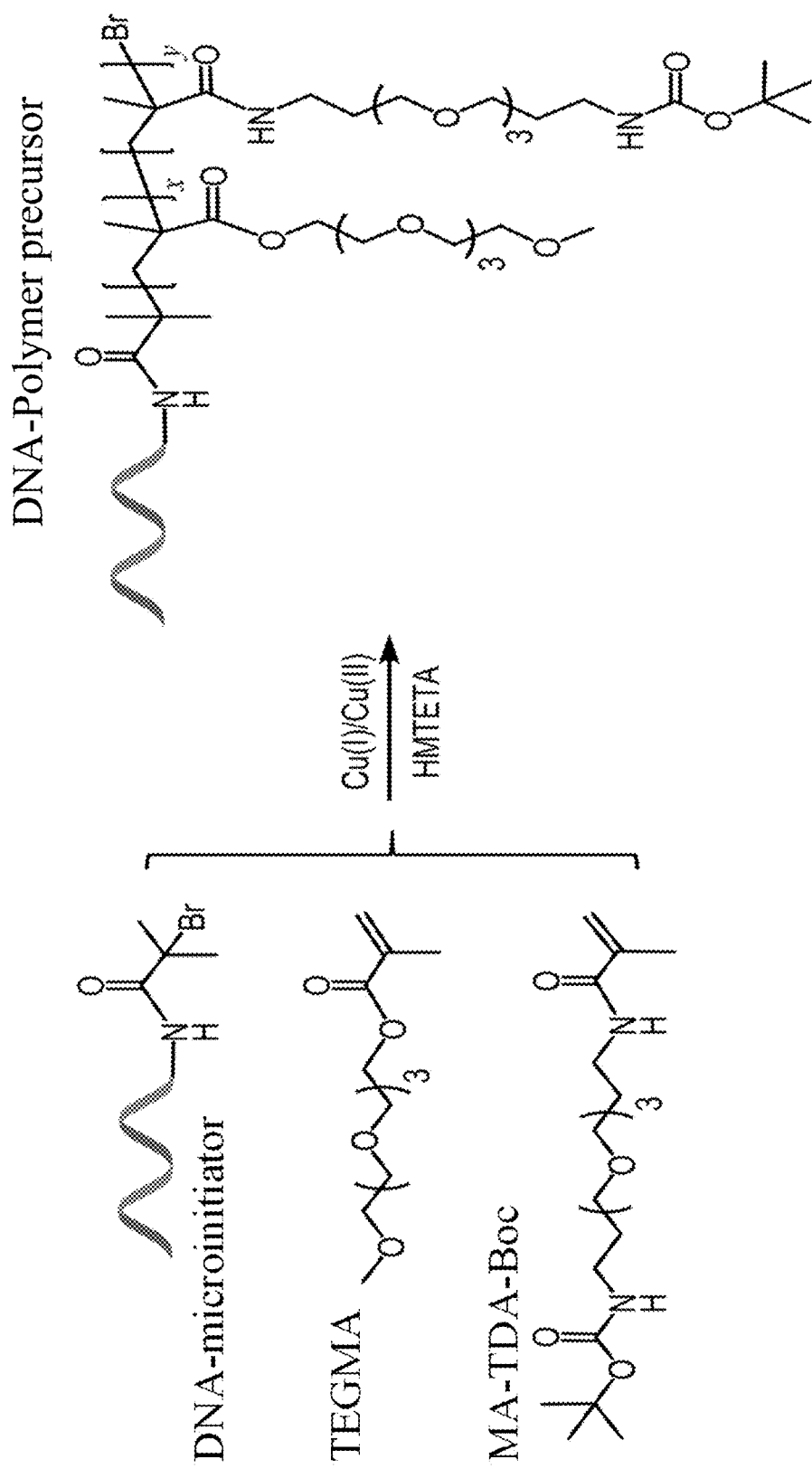
FIG. 17 depicts a diagram of a method of using ATRP to form a DNA-polymer precursor.

In Situ ATRP to Form DNA-Polymer Precursor (FIG. 17)

ATRP reactions were performed as follows: Solution A was prepared by mixing copper (I) chloride (10 mg), copper (II) sulfate (1.2 mg) and HMTETA (40) in 0.5 mL MilliQ water. Solution B was prepared by adding TEGMA and MA-TDA-Boc to 30 nmol of DNA-microinitiator (DNA-microinitiator:TEGMA:MA-TDA-Boc=1:100:100, 1:100:50 or 1:1000:10) in a mixture solution of water and DMSO (50/10 The two solutions were separately degassed with argon for 30 min, after which 2 μL solution A was quickly transferred into the solution B. The polymerization was preceded for 2 h at room temperature under argon and was quenched by bubbling with air. The DNA-Polymer precursors were purified using dialysis.

Figure 18:
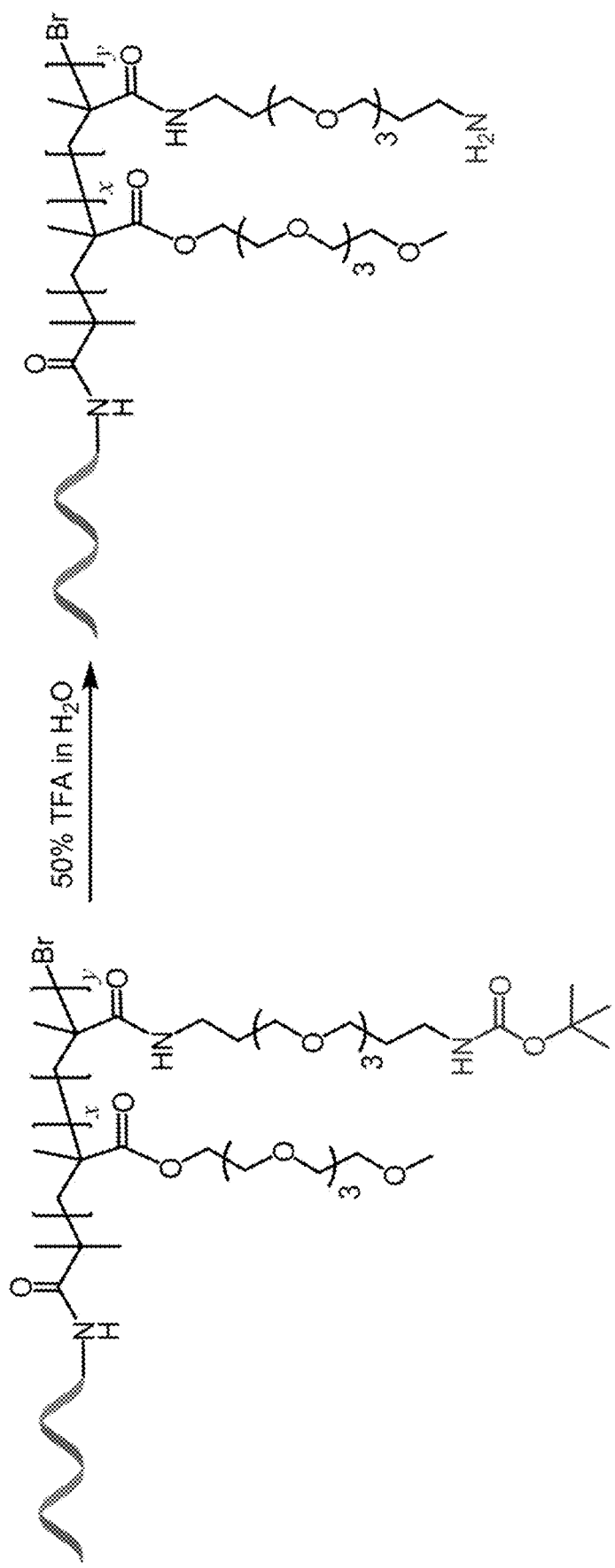
FIG. 18 depicts a diagram of the activation of the DNA-polymer precursor.

Activation of the DNA-Polymer Precursor (FIG. 18)

The DNA-Polymer precursor was activated by removing the Boc-group that attached on amino moiety. DNA-Polymer precursor was dispersed in a 50% TFA/H2O solution and vortexed at room temperature for 2 h. Thereafter, the solution was neutralize with PBS. The resulted DNA-Polymer was collected by spin filter and was washed with PBS several times to remove the acid.

Figure 19:
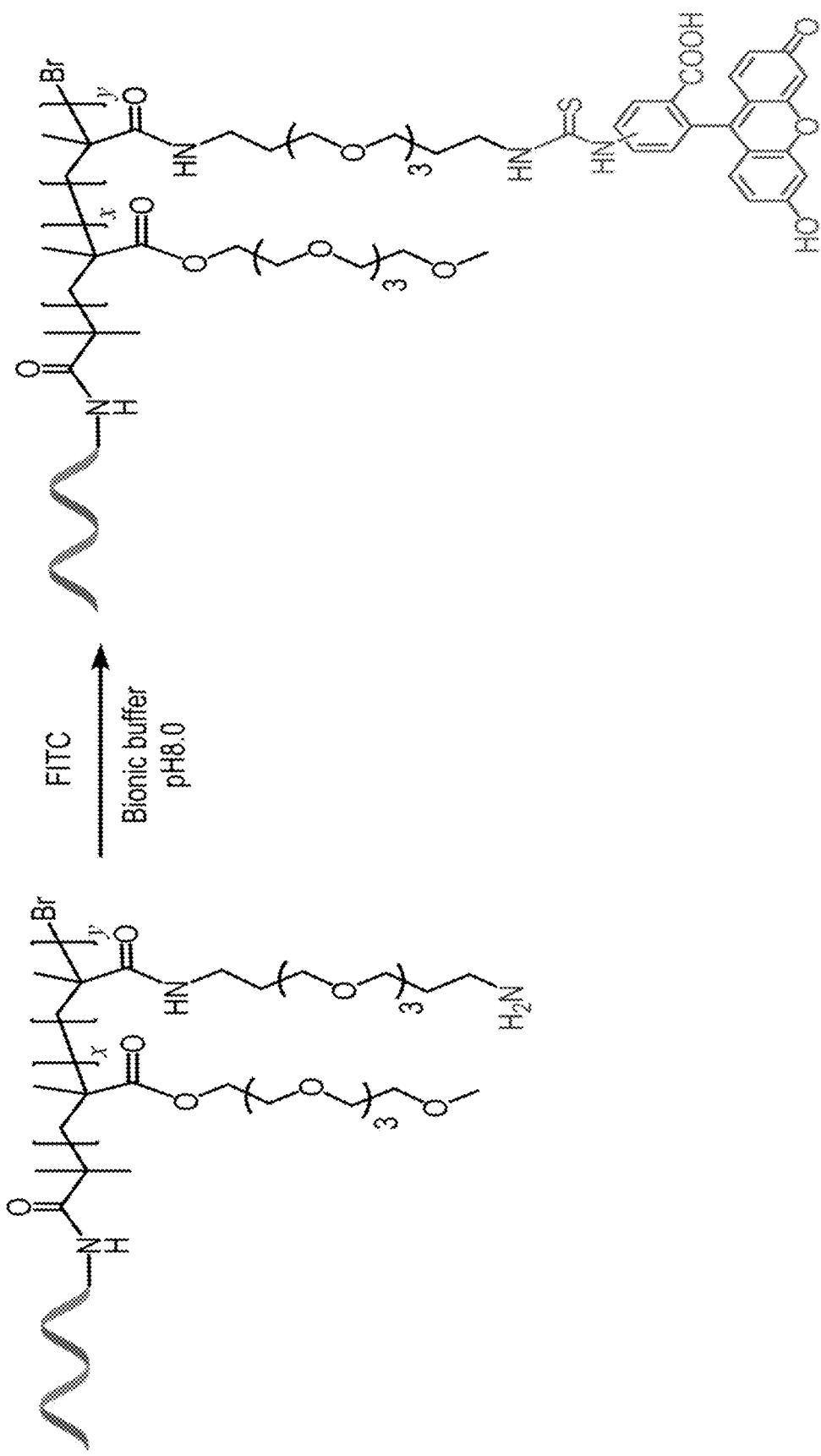
FIG. 19 depicts a diagram of a method of labeling the activated DNA-polymer precursor with a fluorophore.

Labeling the Activated DNA-Polymer Precursor with Fluorophore (FIG. 19)

The activated DNA-Polymer precursor has an amino group, which is ready to conjugate with various fluorophores such as FITC, TRITC, and succinimidyl ester activated fluorophores. Typically, a solution of FITC (1 μmol) and activated DNA-Polymer precursor (1 nmol) in 1 mL bionic buffer was vortexed at room temperature for overnight. After reaction, the solution was dialysis in PBS to remove the unreacted FITC. The fluorescent DNA-Polymer was collected by spin filtration.

Characterization

UV-vis absorption spectra were recorded on a Varian Cary 50 spectrophotometer. Fluorescence spectra were recorded on a Varian Cary Eclipse fluorescence spectrophotometer. FT-IR spectra were collected on an Avatar Nicolet FT-IR330 spectrometer. $^1$H NMR and $^{13}$C NMR were acquired on Bruker 300/400 MHz NMR spectrometer. ESI-MS was collected on Finnigan LCQ™ DUO LC/MS spectrometer. MALDI-TOF spectrum was recorded on an ABI-MDS SCIEX 4800 MALDI-TOF/TOF mass spectrometer. The DLS size and zeta potential was collected on a Malvern Zetasizer nano S.

All the synthesized small monomers are characterized by $^1$H-NMR and $^{13}$C-NMR spectrometer, ESI-MS spectrometer and FI-IR spectrometer to confirm their molecular structures. The fluorescent DNA-Polymer conjugates are characterized by DLS and polyacrylamide gel electrophoresis to confirm the successful conjugation fluorescent polymer. The fluorescence properties are characterized fluorescence spectroscopy and fluorescence microscopy.

The Experiments are Now Described

Pairing of Polymeric Fluorophores and DNA Polymers

Figures 20A, 20B:
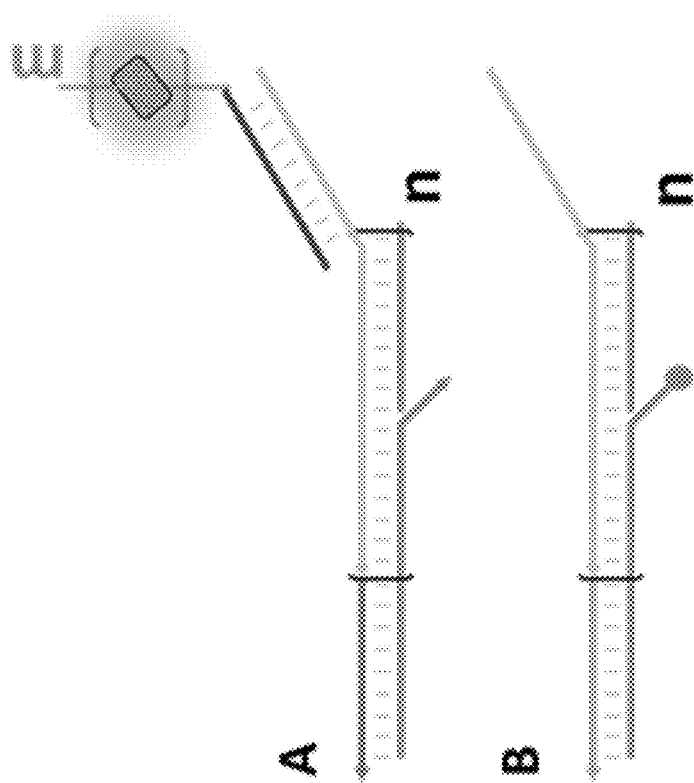
FIG. 20A and FIG. 20B, depicts schematic diagrams of fluorescently labeled BP.

The hybridization of DNA oligonucleotide monomers to form polymeric DNA structures has been described in detail in the prior example. Experiments herein have been designed to use DNA polymers as a backbone to hybridize with DNA-conjugated polymeric fluorophores that carry multiple (m) fluorophores (FIG. 20). By integration of polymeric fluorophores and DNA polymers, sufficient signal amplification (m fluorophores multiplied by n units) for sensitive in situ protein analysis can be achieved.

Evaluate Hybridization of Polymeric Fluorophores and DNA Polymers Using Gel Electrophoresis and Surface Plasmon Resonance (SPR)

Experiments have been designed to use SPR spectroscopy (with a Reichert SPR instrument (SR7500DC)) to demonstrate that polymeric fluorophores can be used to detect the hybridization of DNA polymers. The solution of biotinylated DI is immobilized on a streptavidin-coated biochip. The polymerization solution containing the mixture of DM1 and DM2 is flowed over the chip at a flow rate of 5 μL/min. Subsequently, the chip will be washed with PBS at 30 μL/min and then a solution of DNA-conjugated polymeric fluorophores is flowed on the biochip surface.

Depolymerization of DNA polymers with and without polymeric fluorophores is examined by both gel electrophoresis and SPR. The overall procedure is the same as described above. The solutions of DNA polymers before or after hybridization with polymeric fluorophores are treated with molecular triggers (triggering oligonucleotides) before being loaded into the wells of agarose gel. The mole ratio of triggering oligonucleotides to $DM_1$ is 1:1. For the SPR analysis, after the hybridization of DNA-conjugated polymeric fluorophores and DNA polymers, the buffer containing triggering oligonucleotides is flowed over the surface at 30 μL/min.

These experiments demonstrate a DNA-based reversible signal amplification method using DNA polymers, polymeric fluorophores and molecular triggers.

Figure 21:
FIG. 21 depicts representations of the active and inactive initiating ssDNA conjugated to a monoclonal antibody for detection of a protein of interest.

Evaluation of Multiplex Protein Analysis Via Reversible In Situ Signal Amplification Experiments have been designed that demonstrate the application of the reversible signal amplification method for reiterative protein analysis. Six protein targets are used as a model system, including CD44, Cadherin-11, tubulin, Bcl-2, lamin A and nucleoporin. They represent the cell's three major compartments including cell membrane (CD44 and Cadherin-11), cytoplasm (tubulin and Bcl-2), and nucleus (lamin A and nucleoporin). To demonstrate the potential of this method for multiplex protein analysis, these 6 proteins are divided into two groups. Group 1 includes CD44, tubulin, and lamin A; group 2 includes cadherin-11, Bcl-2 and nucleoporin. Immunoassays have been designed in which these proteins are recognized by antibody-DI conjugates. Upon addition of DNA monomers to the system, DI induces the formation of DNA polymers that further hybridize with DNA-conjugated polymeric fluorophores for increased signal amplification. Three specific sets of DNA initiator, DNA monomers and polymeric fluorophore are used for staining each group of proteins, allowing for target-specific signal amplification. Moreover, molecular triggers (triggering oligonucleotides) which specifically recognize their corresponding DNA monomers due to high-fidelity intermolecular hybridization, are used to ensure specific depolymerization and destaining. It is also important to note that during depolymerization and destaining, the antibody-DI conjugate is automatically blocked to lose its original ability to initiate DNA polymerization (FIG. 21). Thus, the next round of protein recognition and signal amplification is not interfered with.

Example 3: Amine Linkage in Formation of the Targeting Complex

One mechanism of linking DI to a targeting molecule such as an antibody is through linkage of the amine group of the DI oligonucleotide with S-4FB which can participate in an S-4FB:S-HyNic reaction.

The Methods are Now Described

Conjugation of DI with Antibodies Through Amine Linkage

DI with an amine terminal group was desalted and transferred to a DPBS solution (pH 8.0), then mixed with S-4FB in DMSO at a 20:1 S-4FB to DI molar ratio for 2 h at 25°

C. The reaction was exchanged to DPBS (pH 6.0) using a Vivaspin 500 5 KDa MWCO centrifugal filter at 15,000×g for 10 min. This step was repeated 6 times and the solution was stored at 4° C. until conjugation with modified antibody. B-tubulin antibody was desalted and hydrated to 1 mg/mL in DPBS (pH 8.0) for a final volume of 100 µL. This solution mixed with 2 µL of 2.86 µg/µL S-HyNic in DMSO for 2 h at 25° C. A Vivaspin 500 50 KDa MWCO centrifugal filter was used to purify the modified antibody by spinning 10 min. at 15,000×g. This step was repeated 3 times, exchanging the modified antibody to DPBS (pH 6.0). To this solution, 4FB-DI was added at a molar ratio of 15:1 4FB-DI to HyNic-antibody, along with analine catalyst. This reaction was incubated at 25° C. for 2 h, followed by conjugate purification using an Amicon Ultra 0.5 mL 100 KDa MWCO centrifugal filter. This was run for 5 min. at 14,000×g for 3 repeats, exchanging the solution to DPBS (pH 7.4). Conjugates were stored at 4° C. until use.

Figures 22A, 22B, 22C:
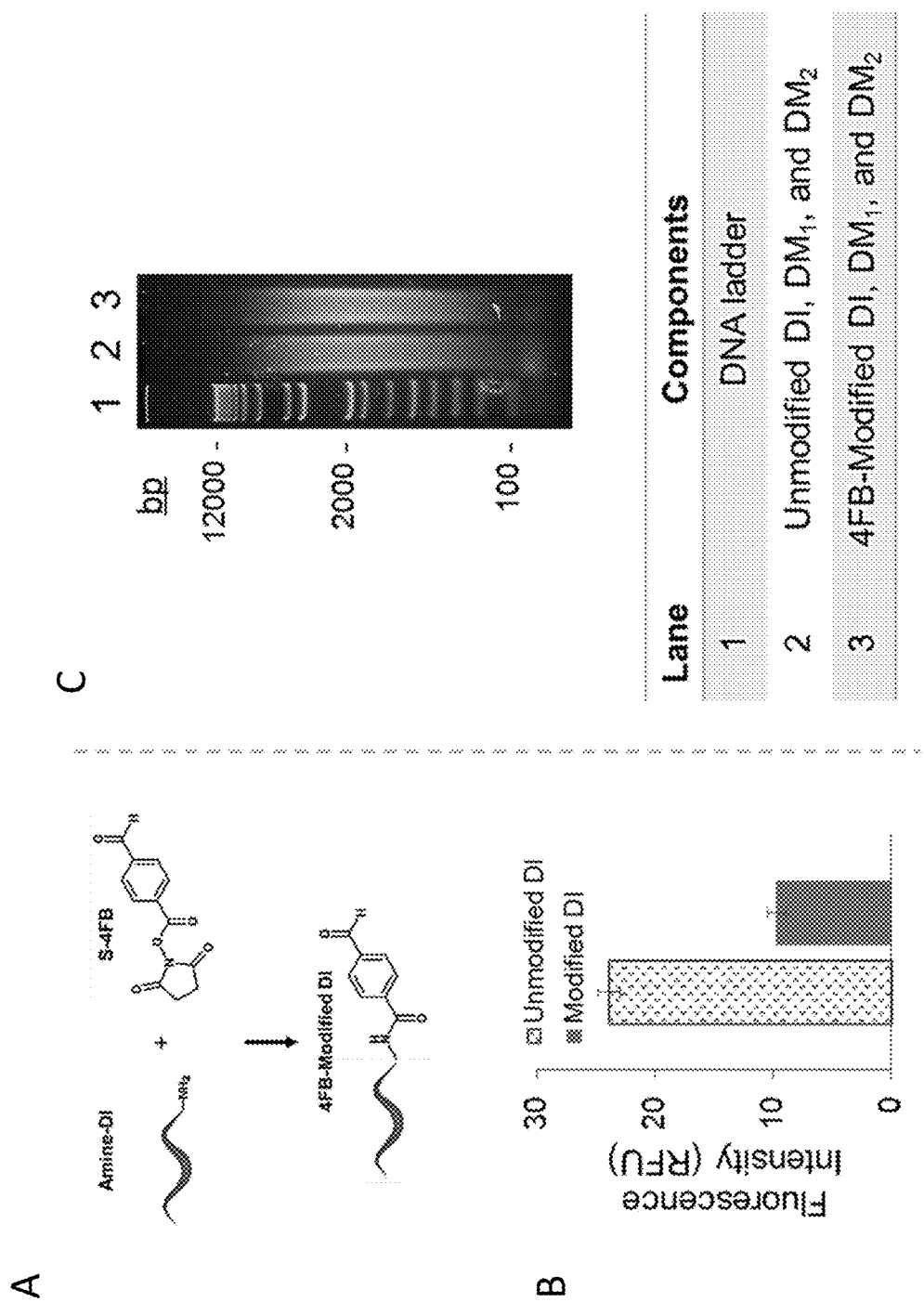
FIG. 22A through FIG. 22C, depicts modification of DI with S-4FB linking molecule.
Figures 23A, 23B:
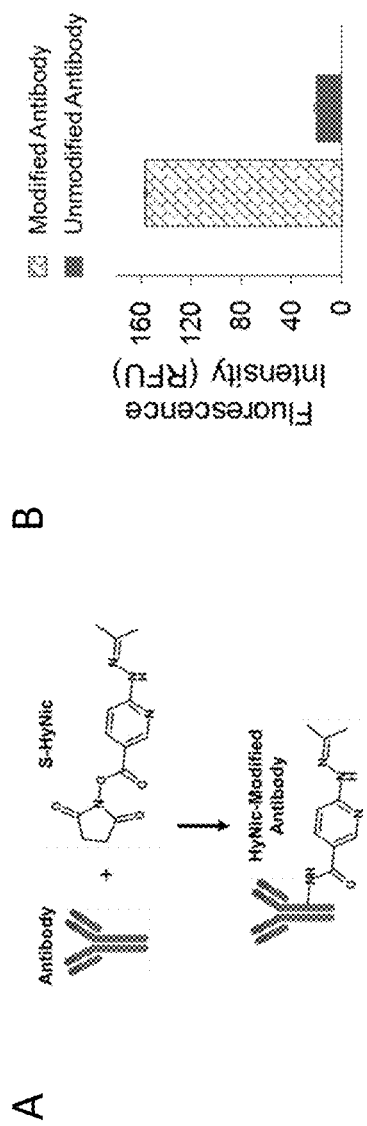
FIG. 23A and FIG. 23B, depicts modification of an antibody with S-HyNic linking molecule.
Figures 24A, 24B:
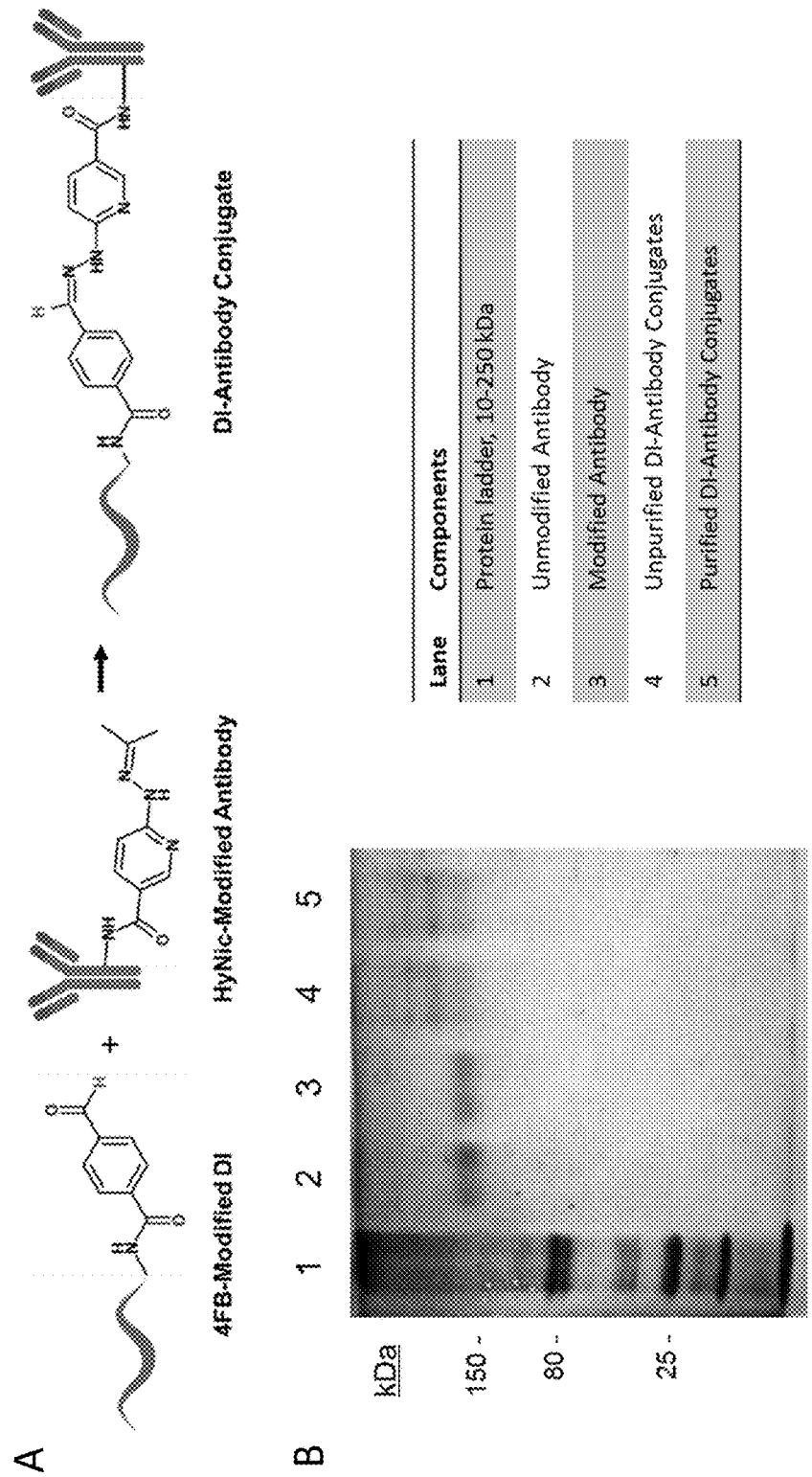
FIG. 24A and FIG. 24B, depicts conjugation of DI with an antibody thorough 4FB-HyNic interaction.

The results of the experiments are now described.
Modification of DI with S-4FB Linking Molecule For participation in an S-4FB:S-HyNic reaction, DI was modified with a linkage to 4FB. FIG. 22 shows results from a fluorescamine assay confirming the modification of DI, as seen by a reduction in fluorescent intensity. Fluoresamine binds to free amine groups and emits a fluorescent signal. Modified DI has lower fluorescence intensity than unmodified DI due to its amine groups being linked with 4FB.
Modification of an Antibody with S-HyNic Linking Molecule For participation in an S-4FB:S-HyNic reaction, a targeting antibody was modified with a linkage to HyNic. FIG. 23 shows results from a fluorescamine assay confirming the modification of the antibody, as seen by a reduction in fluorescent intensity.
Targeting Complex Generation Though S-4FB:S-HyNic Linkage FIG. 24 demonstrates that DI-4FB is able to form a complex to Antibody-HyNic through an S-4FB:S-HyNic reaction.

Example 4: DNA Polymers for the Enhanced Labeling of Multiple Cellular Biomarkers Several conjugate systems have been developed for improved cell labeling that utilized primary antibodies or DNA as recognition elements and components such as quantum dots or polymers for signal amplification (Schweller et al., Angew Chem Int Ed Engl. 2012, 51:9292-9296; Jungmann et al., Nat Methods. 2014, 11:313-318; Zrazhevskiy and Gao, Nat Commun. 2013; 4:1619). Conjugate systems can also increase the number of labeled targets per sample to as many as 10 (Jungmann et al., Nat Methods. 2014, 11:313-318) by using destaining techniques.

DNA polymers have been incorporated into an antibody conjugate labeling system for increased fluorescence signal. Antibodies are conjugated to DNA initiators, giving conjugates dual functions: target recognition and DNA polymers initiation. Once cells are labeled, two DNA monomers are hybridized at the initiator site to form DNA polymers. Notably, these polymers can be hybridized with multiple fluorophores per reaction site, amplifying the signal. Moreover, two distinct sets of DNA polymers were developed for simultaneous labeling of cell targets. The signal intensity of these polymers was demonstrated to be more than 5 times greater than that of monomeric conjugate labels and over an order of magnitude greater than traditional immunofluorescence labels.

The materials and methods are now described
Materials and Methods
Materials and Chemicals Dulbecco's phosphate buffered saline (DPBS), glycerol, SYBR Safe DNA stain, agarose, tris/borate/EDTA (TBE) 10× solution, TrackIt 1 Kb Plus DNA ladder, fluorescamine, HCl, glycine, methanol, propanol, tetramethylethylenediamine (TEMED), ammonium persulfate (APS), fetal bovine serum (FBS), penicillin/streptomycin, Eagle's minimum essential medium, trypsin/EDTA 1× solution, BD cytofix/cytoperm solution, bovine serum albumin (BSA), PIPES, polyvinylpyrrolidone, herring sperm DNA, ethanol, Streptavidin Qdot conjugates (525 nm, 655 nm), and circular cover slips were purchased from Thermo-Fisher Scientific (Waltham, Mass.). Dimethylsulfoxide, MES sodium salt, 2-hydrazinopyridine dichloride, NaOH, SDS, Trizma base, glacial acetic acid, sodium azide, Triton X-100, Tween-20, HEPES, EDTA, and NaCl, were obtained from Sigma Aldrich (St. Louis, Mo.). Protein ladder (10-250 kDa) was purchased from New England BioLabs (Ipswich, Mass.), while S-4FB, S-HyNic, and analine 10× catalyst solution were purchased from Solulink (San Diego, Calif.). Bromophenol blue, β-tubulin antibody (H-235), and COX4 antibody (F-8) were obtained from Santa Cruz Biotechnology (Dallas, Tex.). Acrylamide/bis solution (37.5:1) and stacking and resolving buffers were purchased from Bio-Rad (Hercules, Calif.). Coomassie Blue R-250 stain was purchased from Teknova (Hollister, Calif.).
DNA Polymer Sequence Design and Treatment DNA sequences were designed and analyzed with NUPACK software (www.nupack.org) and ordered from Integrated DNA Technologies (Coralville, Iowa). Before use, sequences were diluted to desired concentrations in DPBS and annealed using a Bio-Rad T100 Thermal Cycler (Hercules, Calif.) by heating to 95° C. for 5 min, and allowing 1 hr to cool to room temperature.
Gel Electrophoresis Analysis of DNA Polymerization DNA polymer samples were prepared from annealed sequences in DPBS. Monomers and initiators were mixed at a 10:1 molar ratio set 1 and a 3:1 molar ratio for set 2 for a final volume of 24 µL with 0.1 µM DI and 1 µM each monomer. For individual set electrophoresis studies, no fluorophores were conjugated to the DNA; SYBR Safe gel stain was instead used to visualize all double-stranded DNA. Samples were mixed with 2 µL glycerol and loaded into wells of a 1% (w/v) agarose gel (50 mL 1×TBE with 5 µL SYBR Safe). Gels were run for 1 hr at 100 V in a 1×TBE running buffer and imaged using a CRI Maestro in vivo imaging system (Woburn, Mass.) with a blue excitation wavelength (490 nm). All images were produced and pseudocolored using Maestro 3.0.0 software.

Polymer Set 1 is displayed as green, while polymer Set 2 is displayed as red. For combined set electrophoresis, one monomer of set 1 contains a FAM modification, while a monomer from set 2 has a Cy5 modification. For images with these sets combined, SYBR Safe was not included in the agarose gel, and imaging was achieved using both blue (490 nm) and yellow (635 nm) excitation wavelengths. Gel images were merged using ImageJ software.
Flow Cytometry Analysis of DNA Polymer Formation To examine the formation of DNA polymers, fluorescently labeled polymers were initiated on the surface of microparticles. Streptavidin-coated microparticles (5 µm diameter, Spherotech, Lake Forest, Ill.) were rinsed and suspended in flow cytometry buffer (FC Buffer: DPBS, 0.1% Tween-20, 0.02% sodium azide) at 25 µg/sample. Particles were incubated in 0.1 µM biotinylated DI in 20 µL FC Buffer for 1 hr, 25° C., 1000 rpm. After removing the DI solution and washing the particles, solutions of 1 µM DM1 alone or DM1 in combination with DM2 (DM1+DM2) (for monomer or polymer samples, respectively) were incubated with particles overnight at 25° C., 1000 rpm. One monomer in each set was labeled with a FAM fluorophore for detection of polymerization. After thorough washing, particle samples were diluted to 50 µg/mL and analyzed using a Guava easyCyte flow cytometer (Millipore, Billerica, Mass.) with a blue light (Ex, 488 nm) and a green excitation filter (Em, 525±30 nm). Results were analyzed and plotted using FlowJo 10.1 software.

Formation of Initiator Antibody Conjugates

Initiators for conjugation were purchased with a 5' amine modification, along with a 12 C spacer. For modification, 30OD260 units of DI were hydrated in modification buffer (DBPS, pH 8.0) to a final concentration of 0.5 OD260/µL. This solution was desalted using a Zeba 0.5 mL 7 kDa MWCO centrifugal filter before modification with S-4FB. Immediately prior to modification, 1 mg S-4FB was suspended in 40 µL DMSO. Additionally, DMSO was added to the amine-DI solution for a final ⅓ (v/v) DMSO to DI solution. To the DI-amine solution, S-4FB solution was added at a 20:1 S-4FB to DI molar ratio and incubated for 2 hr at 25° C. Following modification, the DI-4FB solution was applied to a Vivaspin 500 5 kDa MWCO centrifugal filter and exchanged to a solution of conjugation buffer (DPBS, pH 6.0). This solution was stored at 4° C. until conjugation with the modified antibody. To determine the molar substitution ratio (MSR) of 4FB to amine-DI, a 0.5 mM 2-Hydrazinopyridine dihydrochloride solution was prepared in 0.1 M MES buffer, pH 6.0. To 18 µL of this solution, 2 µL of either 4FB-DI or water was added and incubated for 1 hr at 37° C. Using a NanoDrop 2000 c spectrophotometer (Thermo Fisher Scientific, Waltham, Mass.) blanked with the control 2-HP-water solution, A260 and A360 values were measured. The MSR was calculated according to Solulink's Antibody-Oligonucleotide Conjugation Calculator (http://www.solulink.com).

For antibody modification, 100 µg antibody was hydrated in 100 µL modification buffer and desalted and buffer exchanged using a Zeba 40 kDa MWCO spin column. For modification 35 µL DMSO was added to 100 µg S-HyNic. To the 1 mg/mL antibody solution, 2 µL of the S-HyNic solution was added for 2 hr at 25° C. Following modification, the antibody-HyNic solution was purified and buffer exchanged to conjugation buffer using a Vivaspin 500 50 kDa MWCO centrifugal filter.

Immediately after antibody modification with HyNic, antibodies were conjugated with 4FB-DI. The volume of 4FB-DI required to add to the HyNic-antibody solution was determined by Solulink's Antibody-Oligonucleotide Conjugation Calculator, and Solulink's analine catalyst was added for a final 1× solution. Conjugates were formed over 2 hr at 25° C. Following conjugation, the DI-antibody conjugates were purified and buffer exchanged to DPBS, pH 7.4 using an Amicon Ultra 0.5 mL 100 kDa MWCO filter. Conjugates were stored at 4° C. until use.

Fluorescamine Assay for Modification Analysis

To determine the percentage of amine groups on each DI modified by linker molecule, 4FB, a fluorescamine assay was performed. The fluorescamine reagent exhibits fluorescence intensity proportional to the free amine groups in solution. As amines are modified on DI, less groups are available for fluorescamine binding and lower fluorescence intensity is measured. Fluorescamine was prepared at 3 mg/mL in DMSO and 3 µL was added to 9 µL of blank, unmodified, and modified samples. Modified and unmodified samples were prepared at equal concentrations in DPBS. After incubating 15 min at 25° C., sample fluorescence was measured using a NanoDrop 3300 fluorospectrometer with the appropriate blank solution. Fluorescence for each sample was measured in triplicate and reference values were subtracted. The percentage of amines modified for each sample was calculated as:

$$\% \text{ modified amines} = \left(1 - \frac{\text{modified fluorescence intensity}}{\text{unmodified fluorescence intensity}}\right) \times 100$$

SDS PAGE Examination of Antibody-DI Conjugates

Antibody and DI-antibody conjugates were analyzed using reducing SDS PAGE. Gels (1.5 mm) were cast with a 4% stacking region and a 7.5% resolving region. The resolving buffer (10 mL) was prepared with 2.5 mL 1.5 M Tris-HCl, pH 8.8, 2.5 mL 30% Acrylamide/Bis solution, 100 µL 10% SDS, and 4.78 mL DI water. Immediately prior to casting, 75 µL 10% ammonium persulfate and 7.5 µL TEMED were added to the buffer and mixed. Resolving solution was pipetted to a level 1 cm below the bottom of the wells. For the stacking buffer (10 mL), the following were mixed: 2.5 mL 0.5 M Tris-HCl, pH 6.8, 1.33 mL 30% Acrylamide/Bis solution, 100 µL 10% SDS, and 6 mL DI water. Immediately before casting, 75 µL 10% ammonium persulfate and 15 µL TEMED were mixed with the stacking buffer. This solution was pipetted atop the polymerized resolving region.

Samples were prepared with 15 µL of 500 ng antibody or conjugates and 15 µL 2× sample buffer. Sample buffer (2×) consisted of 62.5 mM Tris-HCl, pH 6.8, 2% SDS, 25% glycerol, and 0.01% bromophenol blue. Each well was loaded with 30 µL sample and run for 70 min at 125 V in running buffer (25 mM Tris, 192 mM glycine, and 0.1% SDS, pH 8.3). Immediately after gels were run, they were quickly rinsed three times in DI water and placed in fixing solution for 30 min. This solution contained 50% (v/v) methanol, 40% (v/v) DI water, and 10% (v/v) acetic acid. After this, gels were stained overnight at 4° C. using Coomassie Blue R-250 solution. After staining was complete, a primary destain solution consisting of 50% (v/v) DI water, 40% (v/v) methanol, and 10% (v/v) acetic acid was applied for 1 hr, while shaking. After this, a secondary destain solution consisting of 85% (v/v) DI water, 5% (v/v) methanol, and 10% (v/v) acetic acid was applied and decanted as needed until the gel background was clear. Gels were rinsed with DI water prior to imaging with a CRI Maestro in vivo imaging system (Woburn, Mass.).

Cell Culture

A KB (ATCC CCL-17, Manassas, Va.) human epithelial cell line was cultured in Eagle's Minimum Essential Medium supplemented with 10% fetal bovine serum and 100 IU/mL penicillin/streptomycin and incubated at 37° C., 5% $CO_2$, in 95% humidity. Prior to staining, KB cells were seeded on sterilized, 0.1% (v/v) gelatin-coated glass coverslips in the wells of a 24 well plate at a density $2\times10^4$ cells/$cm^2$, 350 µL/well. After reaching approximately 70% confluence, cells were fixed and permeablized using 350 µL BD Cytofix/Cytoperm solution for 20 min at 4° C. Fixed cells rinsed three times in DPBS, shaking at 70 rpm for 5 min, and were stored at 4° C. in storage buffer (1% (v/v) BSA, 0.01% (v/v) sodium azide, and 0.3% (v/v) Triton X-100 in DPBS) until use.

Cell Labeling with Fluorescent DNA Polymers

All blocking and cell incubation steps were performed with coverslips facing upward on a parafilm-coated humidity chamber with a 40 µL of solution atop each sample. Before labeling, cells were first blocked with Blocking Buffer A, consisting of 100 µM DI block sequence in DPBS overnight, at 25° C. Next, Blocking Buffer B (250 mM HEPES, 250 mM PIPES, 0.16 mg/mL polyvinylpyrrolidone, 0.16 mg/mL BSA, 1.6 mM EDTA, and 50 mM NaCl) (Stanlis and McIntosh J. Histochem. Cytochem. 2003, 51:797-808) with 1 mg/mL herring sperm DNA was applied overnight, at 25° C. Blocking solutions were washed three times in DPBS with agitation to remove loosely bound molecules. For labeling with conjugates, 4 µg/mL conjugates were incubated with samples in a DPBS buffer containing 0.2% BSA and 100 µM DI blocksequence at 25° C. for 30 min. In the case of control samples, conjugates were replaced with 4 µg/mL labeled or unlabeled antibodies, or 0.1 µM DI. After labeling with the conjugates or control molecules, samples were washed three times in DPBS. For polymer formation, 1 µM of DM1 and DM2 in Blocking Buffer B were added to samples for 1 hr at 25° C. For one monomeric unit labeling, polymer solution omitted one of the monomers but was applied under the same conditions. Unbound monomers were washed with DPBS three times. A linker sequence that hybridizes to a region on one of the monomers allows the labeling with linked fluorophores. In this case, a biotinylated linker sequences was incubated in Binding Buffer B at 1 µM for 1 hr, followed by the washing of excess. Finally, streptavidin-coated quantum dots were incubated with the samples at 20 nM in a buffer of DPBS with 1% BSA. For multiplexed imaging, the linker and quantum dots for each set of polymers were separately conjugated before hybridization with polymers in DPBS. All samples were washed three times with DPBS prior to imaging.

Imaging and Microscopy

Fluorescently labeled cells were imaged under phase and fluorescence microscopy using an Olympus IX73 inverted microscope equipped with an Olympus U-HGLGPS fluorescence illumination source and an Olympus XM10 camera (Shinjuku, Tokyo, Japan). CellSens Standard software was used for image acquisition, fluorescence pseudocoloring, and image merging. For confocal imaging, cell samples were mounted using Vectashield antifade mounting meda with DAPI and imaged using an Olympus FV10i-LIV wide field confocal microscope with an ORCA 100 Hamamatsu cooled digital camera, UplanFL 40×/0.75 objective, and mercury vapor illumination. Images were acquired, pseudocolored, and merged using FluoView software. Intensity analysis was performed using ImageJ software.

Statistical Analysis

All error bars represent standard deviation of the mean. Statistical significance between two population means was identified using a two sample Student's t-test with P-values of ≤0.05. Prior to the t-test, population variances were compared using a two sample F-test to identify equal or unequal variances. For statistical analysis of multiple groups, one way ANOVA with Tukey's test was performed with P-values of ≤0.05, using Minitab 17 statistical software (Minitab, State College, Pa.). N.S denotes no significance, while * indicates significance.

The results of the experiments are now described.

Evaluation of Two Distinct Sets of DNA Polymers

Cell labeling of multiple components can be important when determining their locations relative to each other or their potential influence on expression. In order to image simultaneous cell components, distinct targeting molecules and fluorophores should be utilized. However, complications can arise from fluorescence signal overlap, high background fluorescence, or non-specific labeling. Thus, labeling systems should prove highly specific in targeting and resolving different fluorescence signals. Two unique recognition and labeling systems, composed of antibody-DNA initiator conjugates and fluorophore-labeled DNA polymers were designed for simultaneous detection of biomolecules. While different antibodies confer specificity for distinct cellular targets, the fluorescence system must be designed for specificity.

Figures 25A, 25B, 25C:
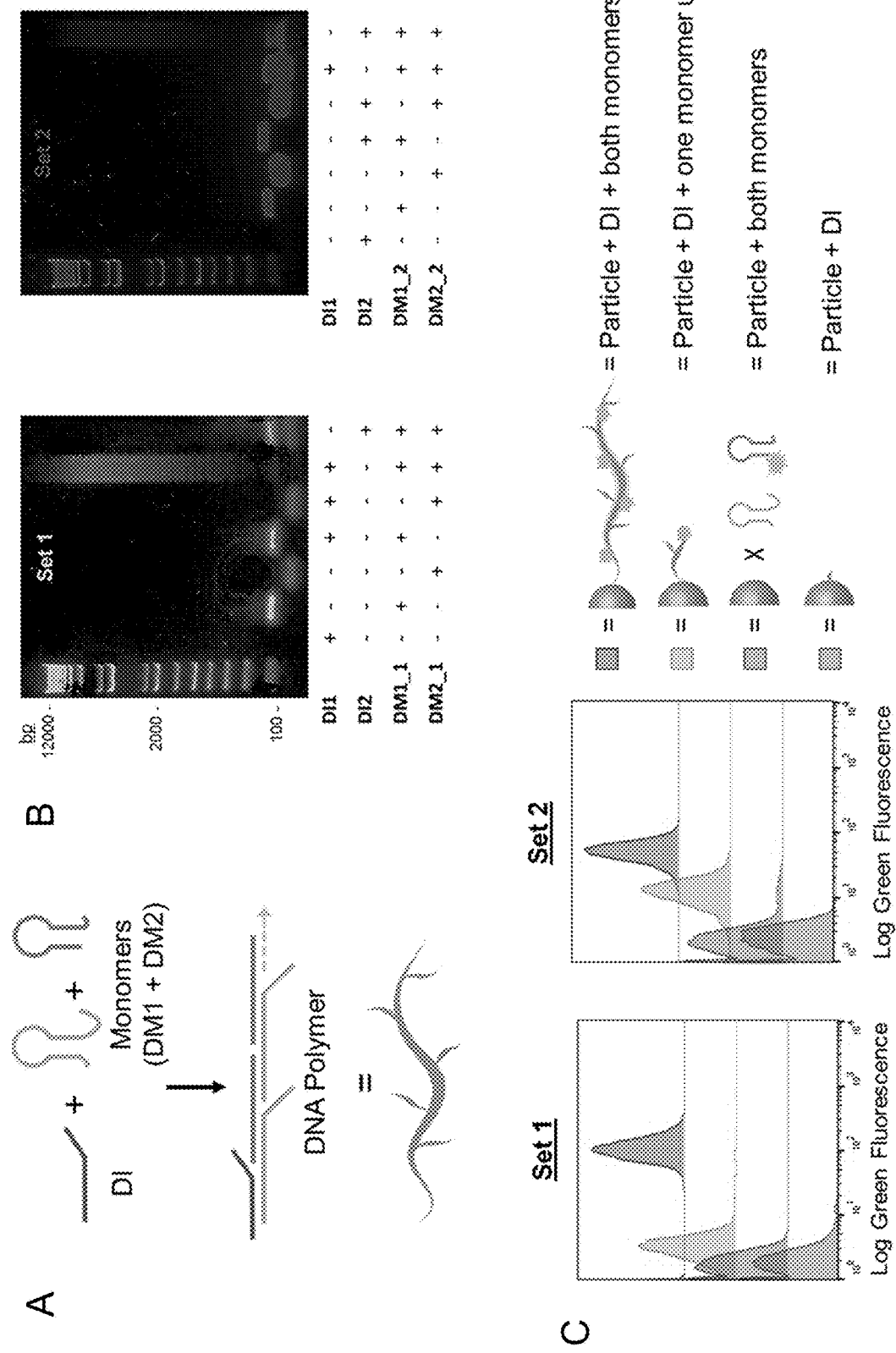
FIG. 25A through FIG. 25C, depicts the synthesis of two distinct DNA polymers.

To this end, two sets of components for the synthesis of DNA polymers were designed and examined. Each set was composed of one linear, single-stranded initiator, DI, and two hairpin monomers, DM1 and DM2. To differentiate between monomers for each set, the nomenclature DM1_1 and DM2_1 for Set 1 monomers 1 and 2, respectively, has been adopted. For Set 2, monomers 1 and 2 have been designated DM1_2 and DM2_2, respectively. Importantly, one monomer in each set has a unique "toehold" region for the hybridization of fluorophores for cell labeling. Thus, the composition of the DNA polymer determines the identity of the fluorophore to be displayed. The formation of DNA polymers from the initiator and both monomers is shown schematically in FIG. 25A. Each set of polymers consists of unique initiator and monomers so that two sets of polymers may form in the presence of all starting components. The formation of both sets of DNA polymers was demonstrated in solution and examined using gel electrophoresis (FIG. 25B). In these images, double-stranded DNA are visualized using SYBR Safe stain and pseudo-colored green (Set 1) or red (Set 2). For each set, DNA polymers are formed only in the situation where both monomers are incubated with the appropriate DI. Notably, polymers do not form when monomers from one set are incubated with the DI from the other set. This is important in conferring specificity of labeling, since fluorophore display is dependent on the makeup of each DNA polymer.

Since cell labeling occurs at the interface between the cellular target and the solution, we performed further examination of DNA polymerization using microparticles as a model surface. Streptavidin polystyrene microparticles were incubated in a solution of biotinylated DI, followed by fluorescent monomer solutions to create DNA polymers at the surface. As controls, we also investigated DI-functionalized particles, bare particles incubated with monomers, and monovalent fluorophore-particles. The results of the flow cytometric analysis of these samples is shown in FIG. 25C for each set of polymers. For each set, DNA polymer-functionalized particles have average fluorescence intensities that are more than an order of magnitude higher than DI-particles or monomer-treated bare particles (FIG. 25C). Additionally, polyvalent fluorophore samples had higher average fluorescence intensities than their monovalent counterparts (FIG. 25C). This data demonstrates that two sets of polyvalent aptamers can be formed from a surface-bound initiating point and enhance signal intensity.

Figures 26A, 26B:
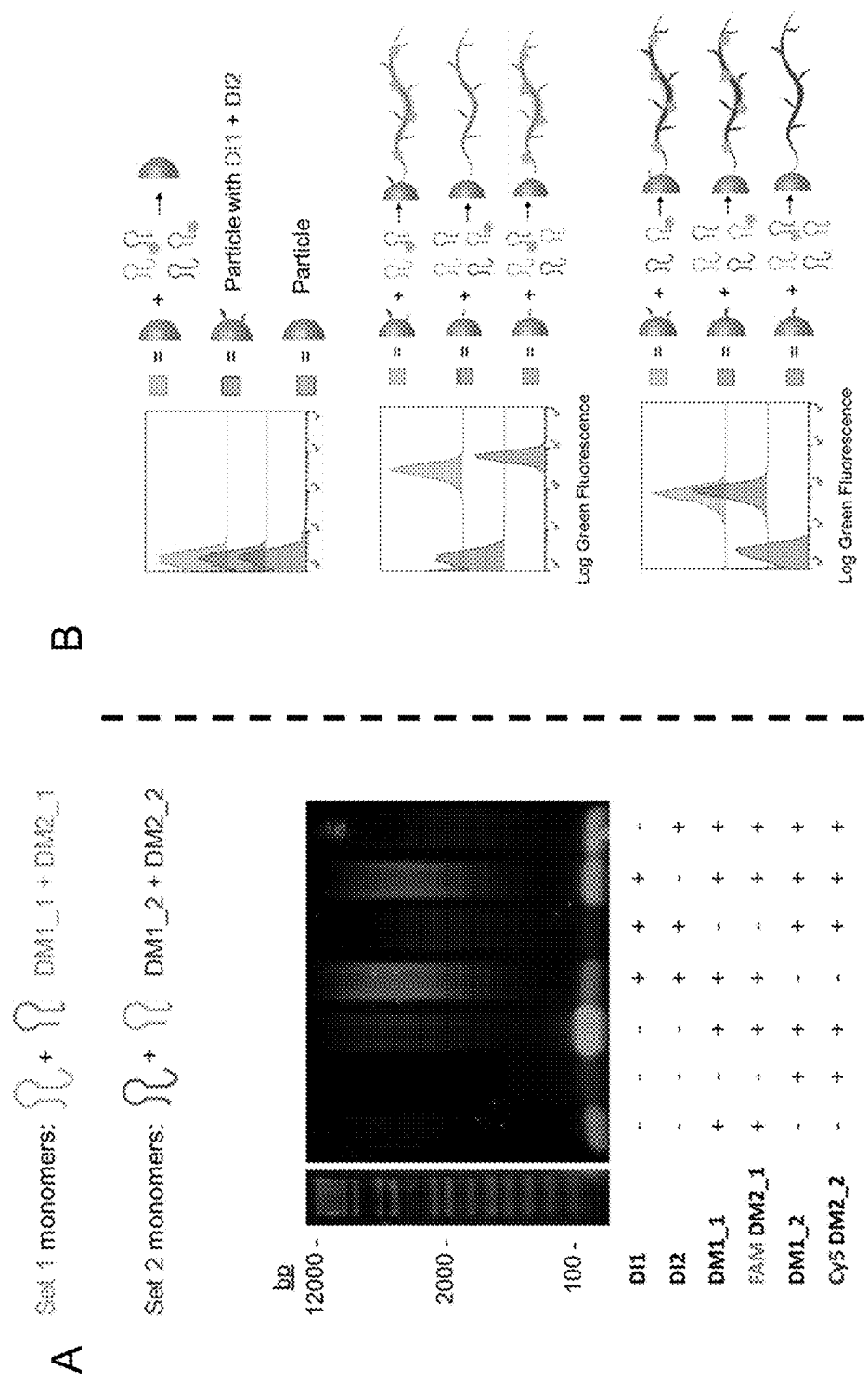
FIG. 26A and FIG. 26B, depicts an analysis of DNA polymer set specificity. Set 1 and Set 2 of polymers were examined to ensure specific polymerization of distinct monomers by the appropriate initiator.

Because both sets of initiators and monomers can be used for simultaneous labeling, it is important to ensure that there is no cross-reactivity between the sets. Moreover, components of one set should not block the polymerization of the second set. Thus, gel electrophoresis was performed to analyze polymer formation in solutions consisting of combinations of polymer components from each set (FIG. 26A). One monomer from each set was labeled with a distinct fluorophore (Set 1, FAM, green; Set 2, Cy5, red), allowing the different polymers to be identified. No significant polymerization is achieved without initiator, as shown in lanes 1-3 (FIG. 22A). In FIG. 22C, lanes 4 and 5, it is clear that each set of monomers can form polymers in the presence of both initiators, suggesting that one initiator does not block the function of the other. Importantly, lanes 6 and 7 show that each DI initiates only its own monomer set, even when monomers from both sets are in solution (FIG. 22A). This specificity of the initiator is important for multiplexed imaging applications, where monomer solutions are incubated with samples simultaneously.

The possibility for cross-polymerization was also investigated on a microparticle surface in FIG. 26B. In this study, one monomer from each set was labeled with the same fluorophore. In the top panel, the flow cytometry data shows that bare particles incubated with all monomers displayed no higher fluorescence intensities than bare particles or particles functionalized with each DI (FIG. 26B, top). This data indicates that there is little non-specific interaction between the monomers and the streptavidin-particles. The center panel in FIG. 26B investigates Set 1 interactions. DI1-particles were incubated with monomers from both sets, where only Set 1 monomers were fluorescently labeled (green signal) or only Set 2 monomers were labeled (purple signal). Though polymers may form in both cases, they are only detected when the fluorophore-labeled monomers are bound to the particle. An increase in fluorescence intensity is only observed when Set 1 monomers were labeled (FIG. 26B, center, green signal), indicating that DI1 only initiates the polymerization of Set 1 monomers. Additionally, when both DI1 and DI2 are functionalized on the same particle, Set 1 monomers produce a shift in fluorescence intensity (FIG. 26B, center, yellow signal), indicating that the initiators do not inhibit each other.

In the lower panel of FIG. 26B, a study similar to the center panel was conducted to investigate Set 2 polymerization. DI2-particles were incubated with solutions of both monomer sets with only Set 1 monomers fluorescently labeled (green signal), or only Set 2 monomers labeled (purple signal). In this case, a shift in fluorescence intensity is only observed when Set 2 monomers were labeled (FIG. 26B, lower, purple signal). This indicates not only that Set 2 polymers can be initiated in the presence of other monomers, but also that Set 1 fluorescent monomers do not participate in the polymerization by DI2 (FIG. 26B, lower, green signal). Moreover, the presence of both DI on the particle allows the formation of Set 2 polymers, as indicated by the fluorescence shift in FIG. 26B, lower panel, yellow signal. Taken together, the data from the flow cytometry studies show that formation of DNA polymers on a surface is highly specific, with little cross-polymerization between DI and monomer sets.

Synthesis and Examination of Initiator-Antibody Conjugates

Though two distinct sets of DNA polymers have been designed and examined, it is necessary to adapt the polymers to labeling via attachment of a ligand. Here, we utilize primary antibodies for the functionalization with DNA initiators to create conjugates with dual functions: to bind target proteins and to initiate DNA polymerization at the target location for clear visualization. Antibodies were used for the recognition role due to their commercial availability, specificity, and high degree of previous characterization (Weiner et al., Nat. Rev. Immunol. 2010, 10:317-27; Pappas and Wang, Anal. Chim. Acta. 2007, 601:26-35). The conjugation between antibodies and DNA is performed by first attaching a linking molecule to amine groups on the DNA and lysines on the antibody. The two linkers are then conjugated to each other, binding the DNA initiator and antibody covalently.

Figures 27A, 27B, 27C, 27D:
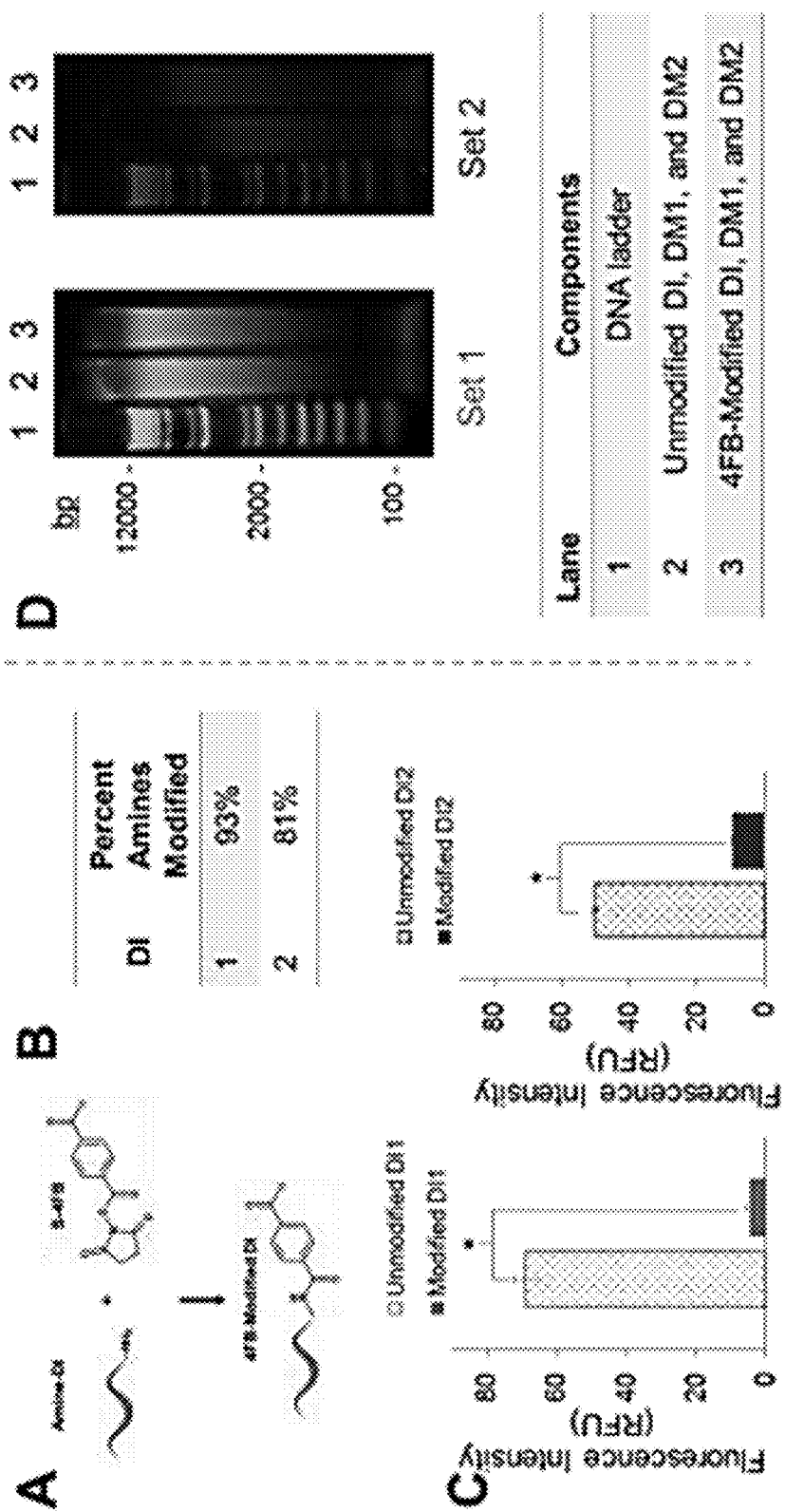
FIG. 27A through FIG. 27D, depicts modification of DI with linking group.

The first step in this procedure is to modify amine-DI with one linking molecule, S-4FB (FIG. 27A). Following this functionalization, the degree of DI modification was assessed using a fluorescamine assay. In this technique, free amine groups bind fluorescamine molecules, producing fluorescence. Therefore, fluorescence intensity indicates unmodified DNA, where amines are still available. The modification analysis is displayed in FIG. 27B and FIG. 27C for both DI1 (green) and DI2 (red). In each case, modified DI had a significantly lower average fluorescence intensity in comparison with unmodified DI, indicating successful modification of DI with the linker, S-4FB. This data indicates that modification was over 80% successful for both DI1 and DI2 (FIG. 27B and FIG. 27C).

One advantage of using DNA as a polymeric material is that functionalization is simple and controllable (Chow and Chilkoti, Langmuir. 2007, 23:11712-11217; Anne et al., J. Am. Chem. Soc. 2007, 129:2734-2735). However, it is important to examine the modified DNA to ensure that added chemical groups do not influence function. To test the initiating function of each modified DI, we compared the polymerization of monomers initiated with both modified and unmodified DI. The results are shown in the electrophoresis images in FIG. 27D, where fluorescence marks double-stranded DNA stained with SYBR Safe. In each comparison, modified and unmodified DI of equal amounts were incubated with equal concentrations of DNA monomers. The data indicates that the modification of each DI had no negative impact on its initiating functionality.

Figures 28A, 28B, 28C:
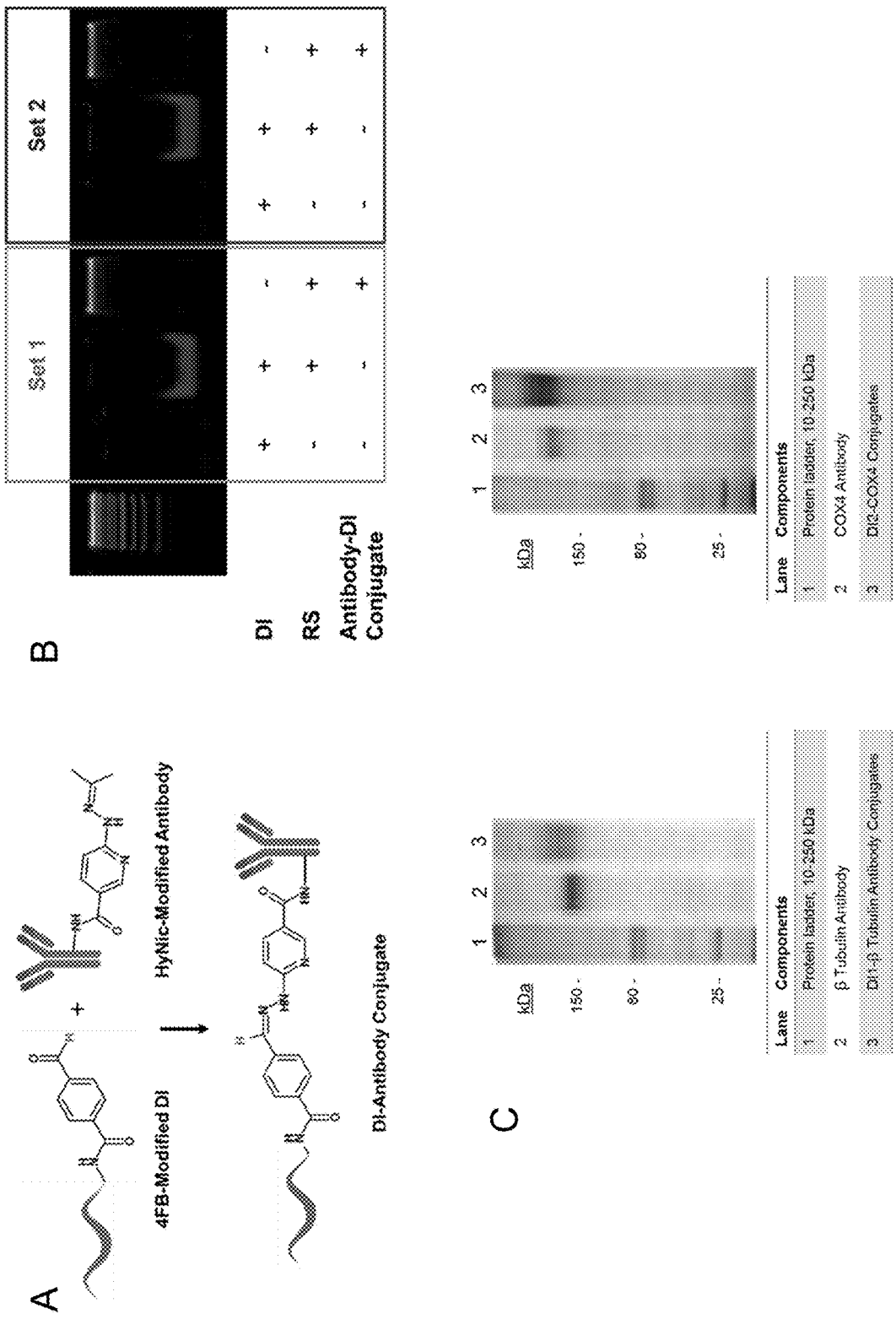
FIG. 28A through FIG. 28C, depicts formation of Antibody-DI conjugates.

In order to attach the antibody to the modified DI, it is necessary to conjugate a complementary linker molecule to the antibody. Here, the linker, S-HyNic, was attached to lysine groups on the antibody. In the next step, the modified antibody was combined with the modified DI, creating DI-Antibody conjugates, as shown in FIG. 28A.

For efficient labeling, it is necessary for conjugates to be purified from the excess free modified DI that were used during the conjugation reaction. To do this, we utilized a size cutoff spin filtration column to separate conjugates from free DNA, and then analyzed the resulting purified conjugates. In FIG. 28B, we used gel electrophoresis to resolve DI-Antibody conjugates and any free modified DI remaining in the purified solution. To visualize the DNA, a linear sequence that is complementary to each DI was incubated with the conjugate or DI solution. The gel was stained with SYBR Safe, which only stains double-stranded DNA and does not label the unbound complementary sequence due to its linear structure. The image shows that lanes with DI contain a low molecular weight band that does not appear strongly in lanes with DI-Antibody conjugates (FIG. 28B). This result indicates that little free DI remains in the purified conjugate solution.

Additionally, we examined the conjugation of antibodies with DI via SDS PAGE. In this study, the shift in molecular weight that accompanies conjugation was examined by comparing antibodies and DI-antibody conjugates. FIG. 28C shows anti β tubulin antibody conjugated to DI1 and anti COX4 antibody conjugated to DI2. The β tubulin antibody labels tubulin, a component of microtubules. The COX4 antibody labels cytochrome C oxidase, which facilitates a proton gradient in the mitochondrial membrane (Van Kuilenburg et al., Biochim. Biophys. Acta. 1992, 1119:218-224). The gel image in FIG. 28C shows that higher molecular weight species are formed after antibodies are modified with DI. This shift does not form a clear band, indicating that variations in molecular weight occur after modification. Therefore, it is possible that multiple DI can be conjugated to each antibody.

Conjugate-Initiated Fluorescent Polymers for Intracellular Protein Labeling

The labeling of intracellular proteins can lead to information about cell activity and mobility based on the location, orientation, and expression of the proteins (de Pedro et al., J. Bacteriol. 2004, 186:2594-2602; Stubbs et al., Diabetes. 2000, 49:2048-2055). Additionally, these protein markers are often varied in diseased states (Ahmed et al., Protein Kinase CK2 Cellular Function in Normal and Disease States. Springer, 2015, p. 378), such that their identification and quantification can lead to improved targeted therapies and basic biological knowledge. However, many target biomolecules have low levels of expression (Haselgrubler et al., Anal. Bioanal. Chem. 2014, 406:3279-3296), or exhibit only slight changes in regulation during diseased states. It is therefore important to utilize sensitive detection mechanisms to visualize these markers.

Here, antibody-initiator conjugates were designed that can label intracellular markers and amplify localized fluorescence signal. This amplification is due to the polymerization of DNA monomers at the target-bound initiator site. The monomers bear toeholds for hybridization with fluorophores, such that each repeat unit of monomers presents a fluorophore.

Figures 29A, 29B:
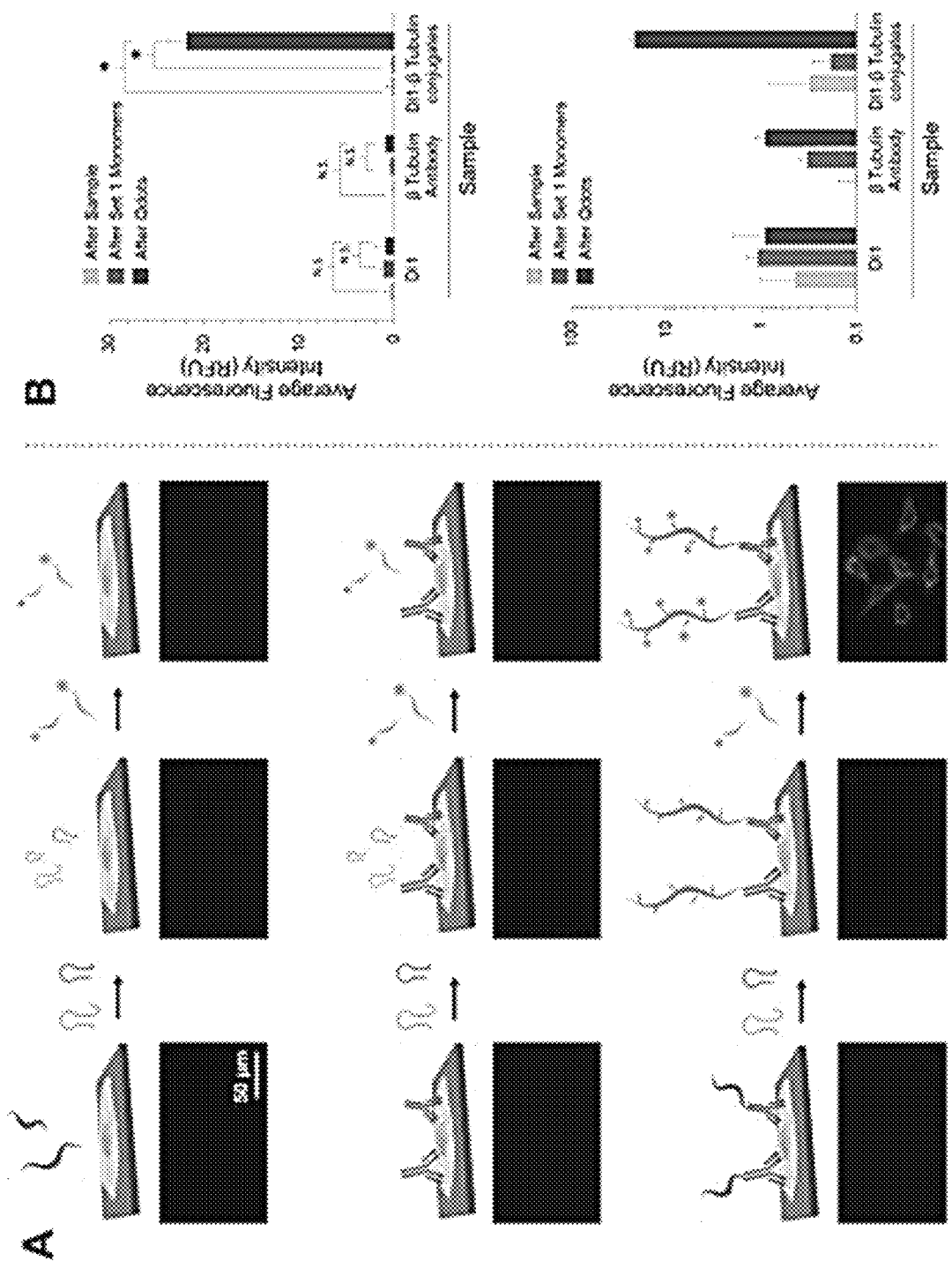
FIG. 29A and FIG. 29B, depicts the specificity of anti β Tubulin-DI1 conjugate labels.

To test the function of the conjugates and ensure specificity, a study was designed using a proof-of-concept target: β tubulin. Fixed cells were labeled with either unconjugated DI, unconjugated anti-β tubulin, or anti-β tubulin-DI1 conjugates, as shown in the first column of images in FIG. 29A. The DI has no targeting molecule, as cannot specifically bind to the cell. In contrast, both unconjugated and DI-conjugated antibodies are capable of binding their targets. However, no fluorescence was observed after the initial labeling step in any sample due to the lack of fluorophores (FIG. 29A). In the second column of images, all samples were washed for loosely bound molecules and incubated with a solution containing both monomers (FIG. 29A). Unconjugated DI is able to initiate the polymerization of these monomers, but is not specifically bound to the cell. Samples with bound, but unconjugated antibodies lack the initiating function of DI and cannot form DNA polymers. However, conjugates are both able to bind targets and initiate the hybridization of DNA monomers, forming polymers locally. In a similar manner to the first incubation step, fluorescence is not observed for any sample due to the lack of fluorophores. Finally, cells were washed to remove excess monomers and incubated with fluorophore solution. The model fluorophores were quantum dots, which were selected due to their high fluorescence intensity, resistance to photobleaching, and compatibility with surface functionalization. The quantum dots were coated with streptavidin and bound to biotinylated sequences that are complementary to the toehold regions on the monomers, facilitating their display on the DNA polymer scaffolds. The display of the fluorophores is shown both schematically and with fluorescence microscopy images in the third column of FIG. 29A. Samples labeled with unconjugated DI could not form localized polymers, and were unable to display the fluorophores. Similarly, minimal fluorescence was observed for unconjugated antibody samples, which bore no DNA polymers due to their lack of DI.

The conjugates successfully labeled the cells, with distinct fluorescence localization. The average fluorescence intensity of the cytoplasm for each sample is displayed in FIG. 29B, with a logarithmic graph of the same data in the lower panel. These results indicate that the conjugates successfully label intracellular targets with little background fluorescence. Additionally, this label is specific for the target protein and is observed in other regions of the cell, such as the nucleus. The increase in fluorescence intensity of the conjugates following fluorophore incubation was statistically significant in comparison to earlier labeling steps and compared to unconjugated DI and unconjugated antibody samples. In particular, the signal was over an order of magnitude higher than control samples or background fluorescence (FIG. 29B).

Figures 30A, 30B:
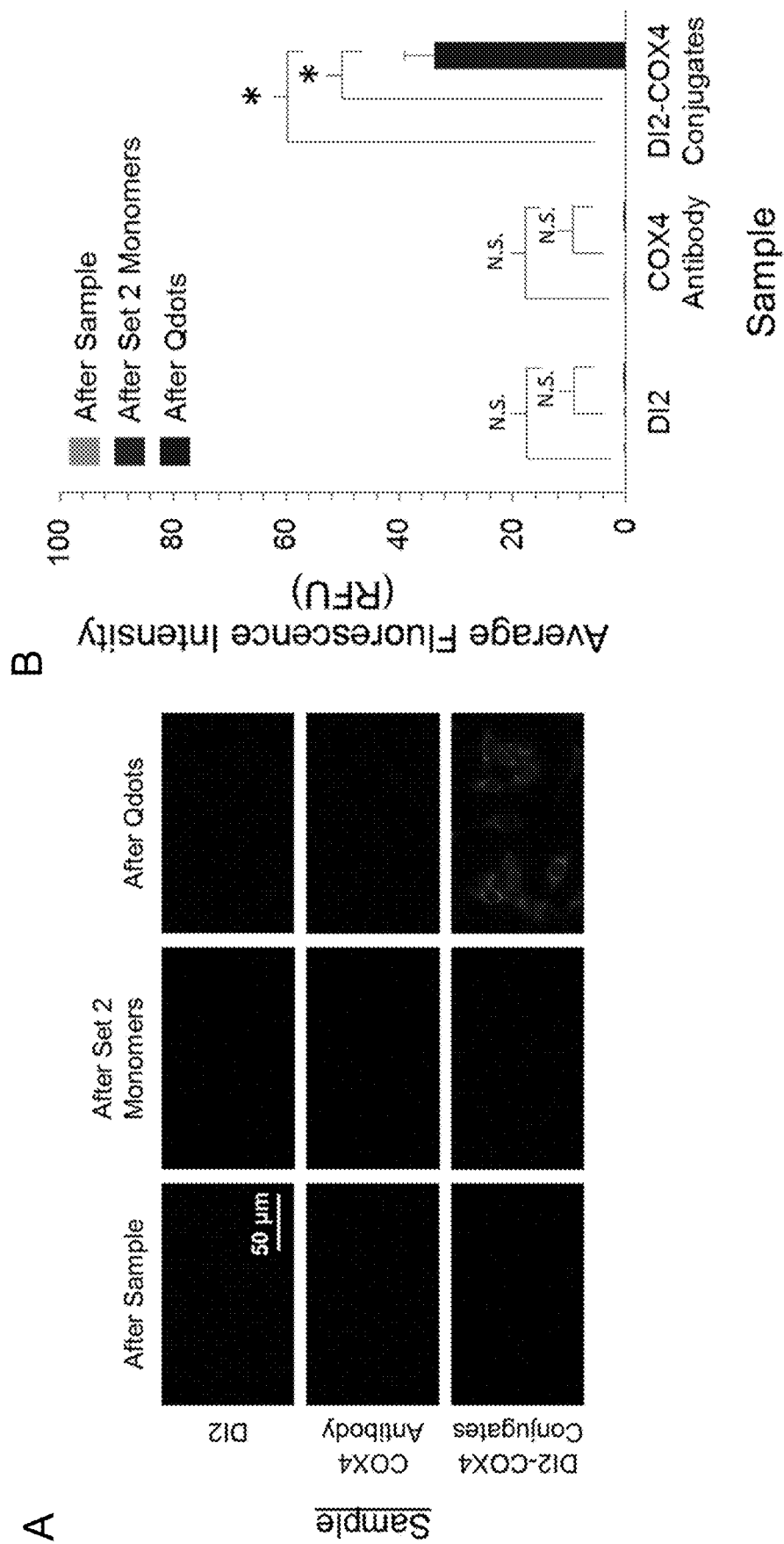
FIG. 30A and FIG. 30B, depicts the specificity of anti COX4-DI2 conjugate labels.

In a similar manner, COX4 antibody-DI2 conjugates and their components were analyzed for specificity. FIG. 30A shows either unconjugated DI2, unconjugated COX4 antibody, or D12-COX4 antibody conjugated incubated with fixed cells. The samples were fluorescently imaged after initial labeling (first column), monomer incubation (second column), and fluorophore incubation (third column) and fluorescence intensity was quantified in FIG. 30B. The results show that increases in fluorescence intensity following fluorophore incubation with conjugates was statistically significant compared to other samples. These conjugates demonstrated effective labeling, with a signal over an order of magnitude greater than controls or background. Additionally, staining pattern was distinct from that of previous β tubulin conjugate labels, indicating conjugate specificity.

Figures 31A, 31B:
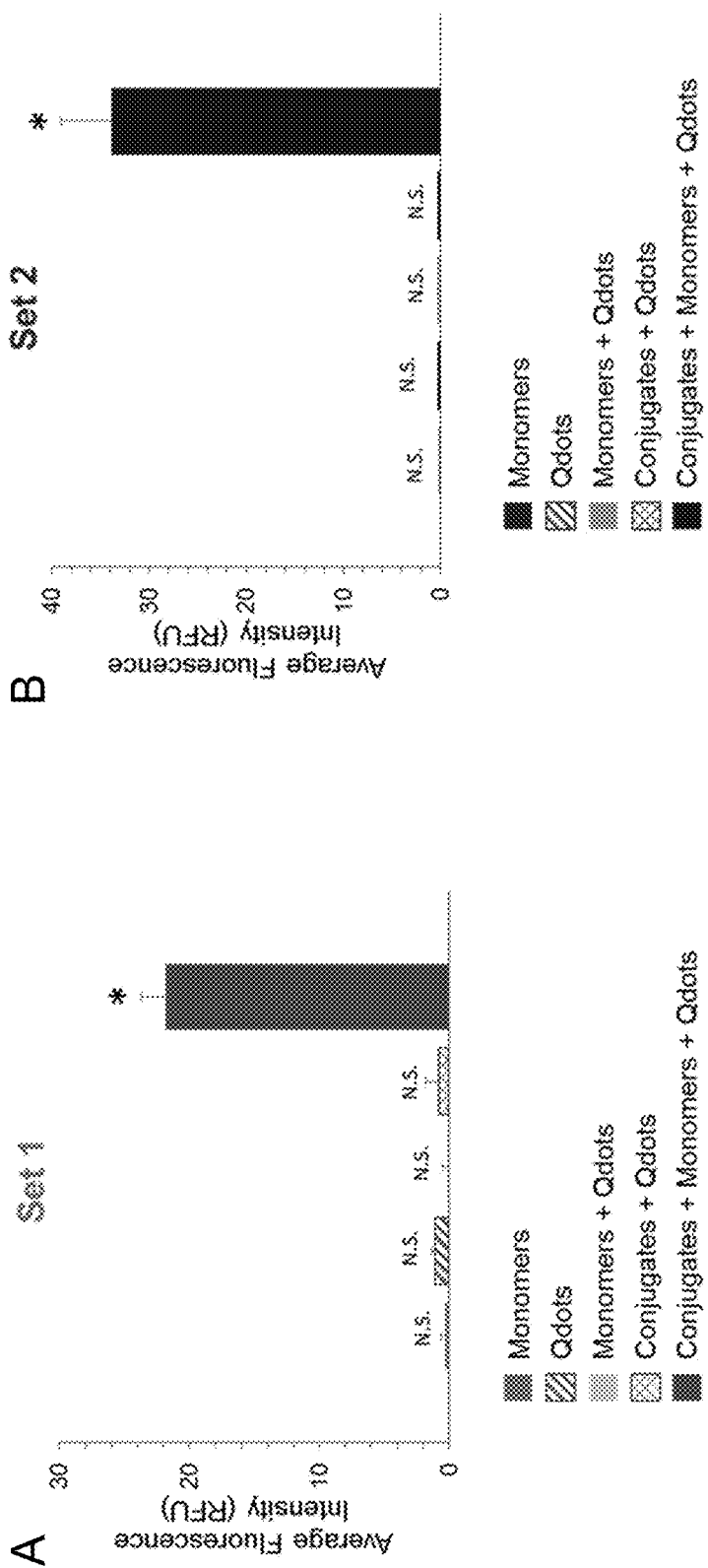
FIG. 31A and FIG. 31B, depicts an assessment of cell labeling background and specificity.

To ensure that fluorophores would only be displayed in the presence of conjugated DNA polymers, several control situations were investigated, as displayed in FIG. 31A and FIG. 31B. Cells were incubated with solutions of monomers, fluorophores, monomers and then fluorophores, or conjugates and then fluorophores. The fluorescence intensities of these samples were then compared to that of samples that had been labeled with conjugates, monomers, and then fluorophores. In the case of monomers, no fluorescence intensity was expected as no fluorophores were in the solution. Samples with only fluorophores displayed low levels of intensity, indicating minimal nonspecific binding (FIG. 31). Similarly, monomer and fluorophore samples showed low levels of nonspecific binding, as the monomers could not polymerize without an initiating molecule and the fluorophores had no region for hybridization. Finally, conjugates treated with fluorophores but without the polymerization of monomers also displayed minimal fluorescence (FIG. 31). These results show that fluorophores bind the polymerized monomers specifically and do not bind directly to the conjugates. The display of fluorophores on monomers is essential for the amplification of signal. Moreover, these trends were observed similarly with both Set 1 (FIG. 31A) and Set 2 (FIG. 31B) of conjugates. The ability to use two distinct, functioning sets of fluorophores enables multiplexed imaging, which is important for examining the relationship between protein targets.

Figure 32:
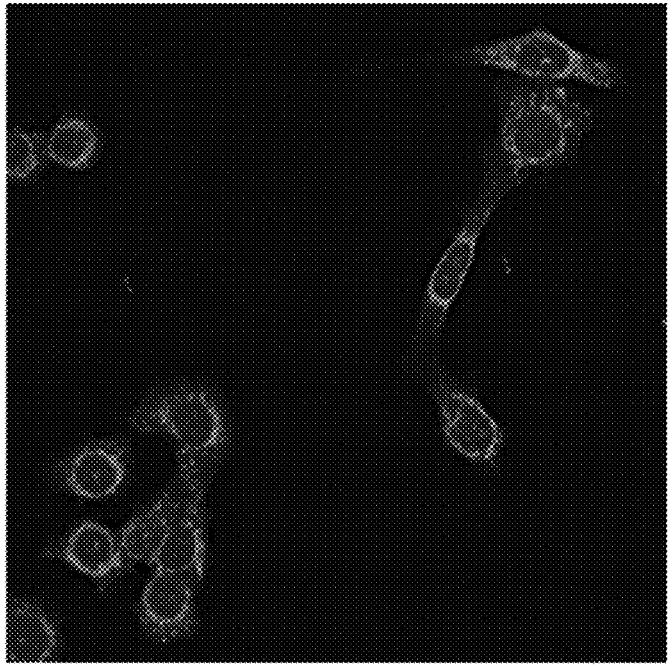
FIG. 32 depicts confocal imaging of conjugate labeled fixed cells. The left panel shows cells stained with anti β tubulin-DI1 conjugates, Set 1 monomers, and Qdot 525. The right panel shows cells stained with anti COX4-DI2 conjugates, Set 2 monomers, and Qdot 655. Nuclei are stained with DAPI for both images.
Figure 32:
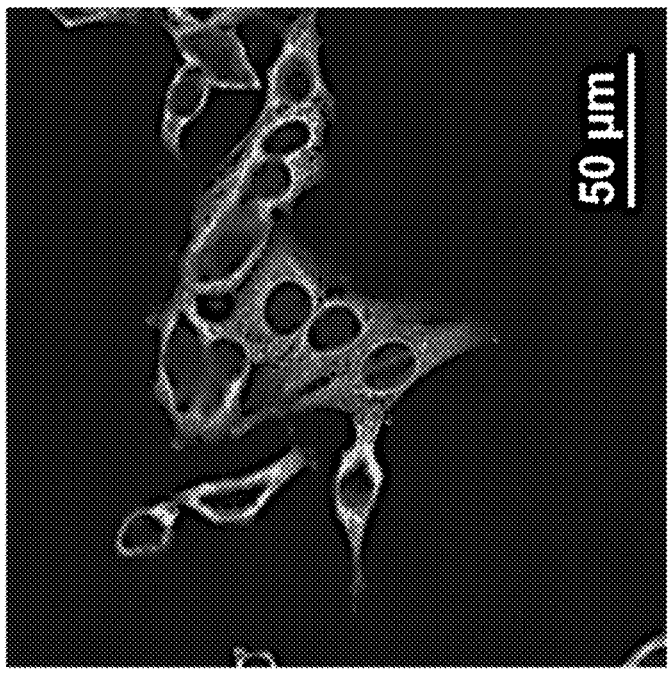

After assessing the ability of conjugates to trigger DNA polymerization and hybridize with fluorophores without nonspecific labeling, we were assured that conjugates can be used for sensitive labeling purposes. Confocal images of fixed cells labeled with either Set 1 conjugates (anti tubulin, Set 1 DNA polymers, and Qdot 525) or Set 2 conjugates (anti COX4, Set 2 DNA polymers, and Qdot 655) show distinct labeling patterns of the intracellular targets (FIG. 32). Low background fluorescence is observed, with a signal to noise ratio of 7.6±0.8 for Set 1 conjugates and 8.2±0.4 for Set 2 conjugates.

Signal Amplification and Multiplexed Imaging Via Polyvalent Fluorophore Labels

Polyvalent systems not only use surface area efficiently, but also allow for a higher density of ligands per unit surface area. In the case of labels, this increase in ligand density results in heightened sensitivity due to signal amplification. In the presented labeling system, polyvalent labeling of intracellular targets has been demonstrated to be highly specific. However, it is necessary to compare this technique to similar, commonly used methods.

The detection and staining of cellular targets is most often achieved via labeling with antibody fluorophore conjugates. While direct labeling of cells with a fluorophore-conjugated primary antibody is simple and fast (Robinson et al., Immunohistochemical Staining Methods, 5th ed./G. L. Kumar and L. Rudbeck, Eds. 2009), signal intensity is relatively low and fluorophore conjugation may affect antibody binding affinity and specificity (Resch-Genger et al., Nat. Methods. 2008, 5:763-775). Therefore, many researchers use indirect immunofluorescence staining techniques. These methods rely on unlabeled primary antibodies for specificity and fluorophore conjugated secondary antibodies for detection. The secondary antibodies are specific to the animal type of the primary antibody, enabling the use each secondary antibody for detection of many primary antibodies. This property of secondary antibodies can reduce materials and cost, but can also be problematic in situations where when secondary antibodies can label multiple different primary antibodies on one sample (Wählby et al., Cytometry. 2002, 47:32-41). However, a benefit of using secondary antibodies is the possibility of amplified signal, which can occur when several secondary antibodies bind each primary antibody (Robinson et al., Immunohistochemical Staining Methods, 5th ed./G. L. Kumar and L. Rudbeck, Eds. 2009).

The presented system builds upon the advantages of both direct and indirect labeling. Because primary antibodies are the recognition element of the conjugates, cells are labeled with high specificity. Additionally, the hybridization of multiple fluorophores to DNA polymers allows signal amplification without sacrificing label specificity.

Figures 33A, 33B:
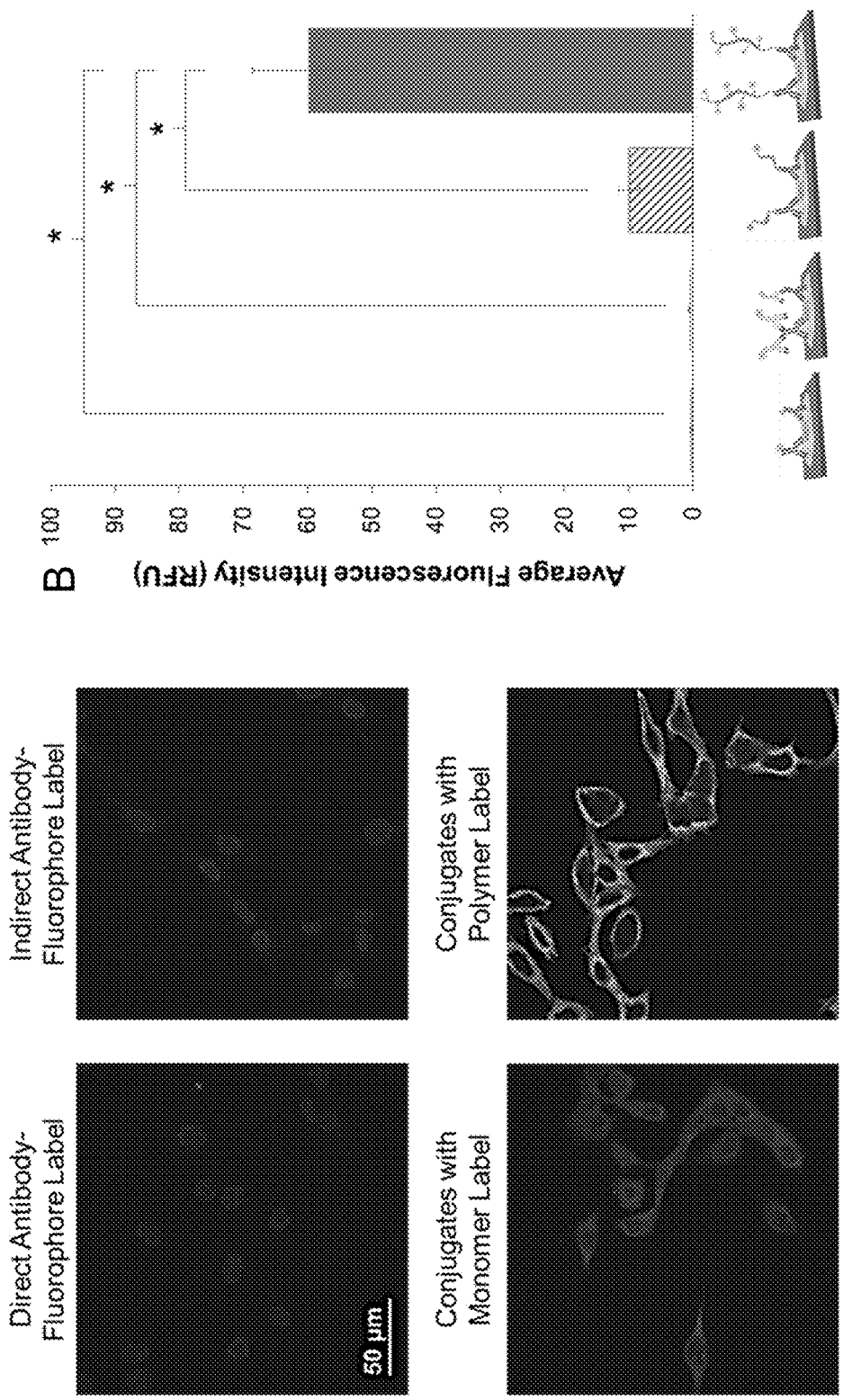
FIG. 33A and FIG. 33B, depicts signal amplification with polyvalent conjugates.

To evaluate the signal amplification of the polyvalent conjugate labeling method, we compared fluorescence signal with that of direct and indirect immunofluorescence staining. Additionally, conjugates with only one fluorophore unit (monomer label) were used as a control to assess polymerization at the cell surface. In FIG. 33A, fixed cells were labeled with equal concentrations of either FITC-β tubulin primary antibody (direct antibody fluorophore label), unlabeled β tubulin primary antibody (indirect antibody fluorophore label), or β tubulin antibody-DT1 conjugates (for both monomer label and polymer label samples). Indirect antibody samples were then labeled with an AlexaFluor 488 secondary antibody. One monomer was incubated with monomer labeled conjugates, while a solution of both Set 1 monomers were incubated with polymer labeled conjugates. All conjugate samples were hybridized with Qdot 525. After cells were imaged under equal conditions for the β tubulin labels, fluorescence intensity was analyzed in FIG. 33B. The data indicate that polyvalent-labeled conjugates provide statistically significant increases in signal intensity compared to all other samples. Specifically, polymer conjugate labels exhibited nearly five times greater fluorescence intensity than monomer conjugate labels, and over an order of magnitude higher signal compared to both standard immunofluorescence techniques. However, monovalent-labeled conjugates also had higher signal than direct and indirect antibody labels. This result may be due to the higher brightness (Gao et al., Curr. Opin. Biotechnol. 2005, 16:63-72) and stability (Resch-Genger et al., Nat. Methods. 2008, 5:763-775) of quantum dots compared to organic fluorophore dyes. Indirect labeling produced a slightly higher signal than direct labeling, indicating the possibility of multiple secondary antibodies binding each primary antibody and amplifying the signal.

Figure 34:
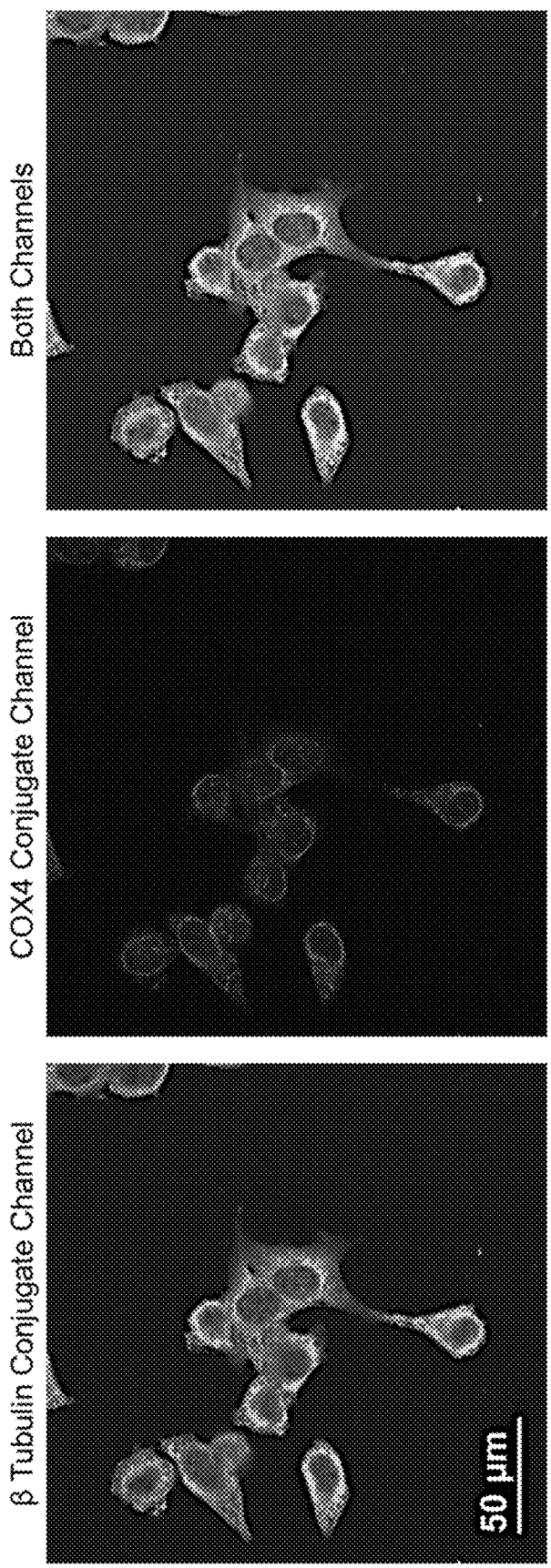
FIG. 34 depicts dual signal amplification of intracellular protein targets. Fixed cells were simultaneously labeled with anti-β tubulin conjugates and anti COX4 conjugates, incubated with both monomer sets, and finally labeled with quantum dots (β tubulin labeled green and COX4 labeled red). Set 1 monomers were initiated by anti-β tubulin conjugates, while anti COX4 conjugates initiated Set 2 monomers. The left panel shows β tubulin in the green channel, the center panel shows COX4 in the red channel, and the right panel shows multi-channel fluorescence. DAPI staining is pseudo colored blue in all images.

Though signal amplification is a goal of this system, another advantage is the use of two distinct sets of DNA polymers. The unique ability of each set of monomers to form polymers at only the appropriate initiating point allows the two sets to be used for multiplexed imaging without concerns for interference. To evaluate the multiplexed labeling ability of two conjugates and DNA sets, we imaged fixed cells with conjugates for both β tubulin and COX4. The conjugates each initiated their own distinct set of monomers, forming two types of DNA polymers. Moreover, these polymers had unique hybridization regions for fluorophore hybridization. Specifically, a linker sequence to Set 1 polymers was attached to Qdot 525, while a linker sequence to Set 2 polymers was attached to Qdot 655. Both fluorophores were incubated with the DNA polymer-labeled cells, and samples were imaged using confocal microscopy. The images in FIG. 34 show the location of β tubulin (green) and COX4 (red) on the same sample. The results indicate that both conjugates were capable of binding their correct cellular target and initiating their associated set of DNA monomers at the cellular location. The success of the simultaneous labeling procedure demonstrates that hybridization processes can occur without interference from each other. These promising results open the avenue for several simultaneous labels to be applied to samples without concerns for specificity.

Example 5: Destaining of Polyvalent Fluorophore Cell Labels

While multiple fluorophore-labeled DNA polymer sets have been developed in this work to stain cellular targets specifically, there are limitations to the number of labels that can be resolved. In general, the spectral overlap of fluorophores can lead to the bleed through fluorescence signal and produce ambiguous staining results (Resch-Genger et al., Nat. Methods. 2008, 5:763-775). Moreover, the resolution of fluorescent dyes requires at least 40-60 nm shift in emission (Martin-Palma et al., Sensors. 2009, 9:5149-5172), limiting the possible combinations of fluorophores for simultaneous labeling.

One method for improving the number of targets for multiplexed fluorescence imaging is to remove a set of labels and replace them with a new set. This method depends on as few as one fluorophore, though its efficiency is multiplied as the number of distinct fluorophores increases per labeling cycle (Zrazhevskiy and Gao, Nat Commun. 2013; 4:1619). A main challenge in this technique is to remove the preceding label thoroughly before relabeling (Pirici et al., J Histochem Cytochem. 2009, 57: 567-575), as this can create high background and imprecise detection. While antibody elution methods exist to remove primary and secondary antibodies though changes in physical parameters (Wahlby et al., Cytometry. 2002, 47:32-41; Pirici et al., J Histochem Cytochem. 2009, 57: 567-575), the destaining of fluorophores is often incomplete. Therefore, alternative destaining strategies have been developed to remove fluorescent labels via unique triggering molecules and phenomena. For instance, the linkages between antibodies and fluorophores have been designed to dissociate or break upon application of light (Agasti et al., J. Am. Chem. Soc. 2012, 134:18499-18502) or specific buffers (Jungmann et al., Nat Methods. 2014, 11:313-318; Zrazhevskiy and Gao, Nat Commun. 2013, 4:1619) releasing fluorophores and destaining cells. Alternatively, DNA-antibody conjugates may contain triggering regions to remove fluorophore labels upon hybridization with complementary DNA (Schweller et al., Angew Chemie Int Ed Engl. 2012, 51:9292-9296).

Figures 35A, 35B, 35C:
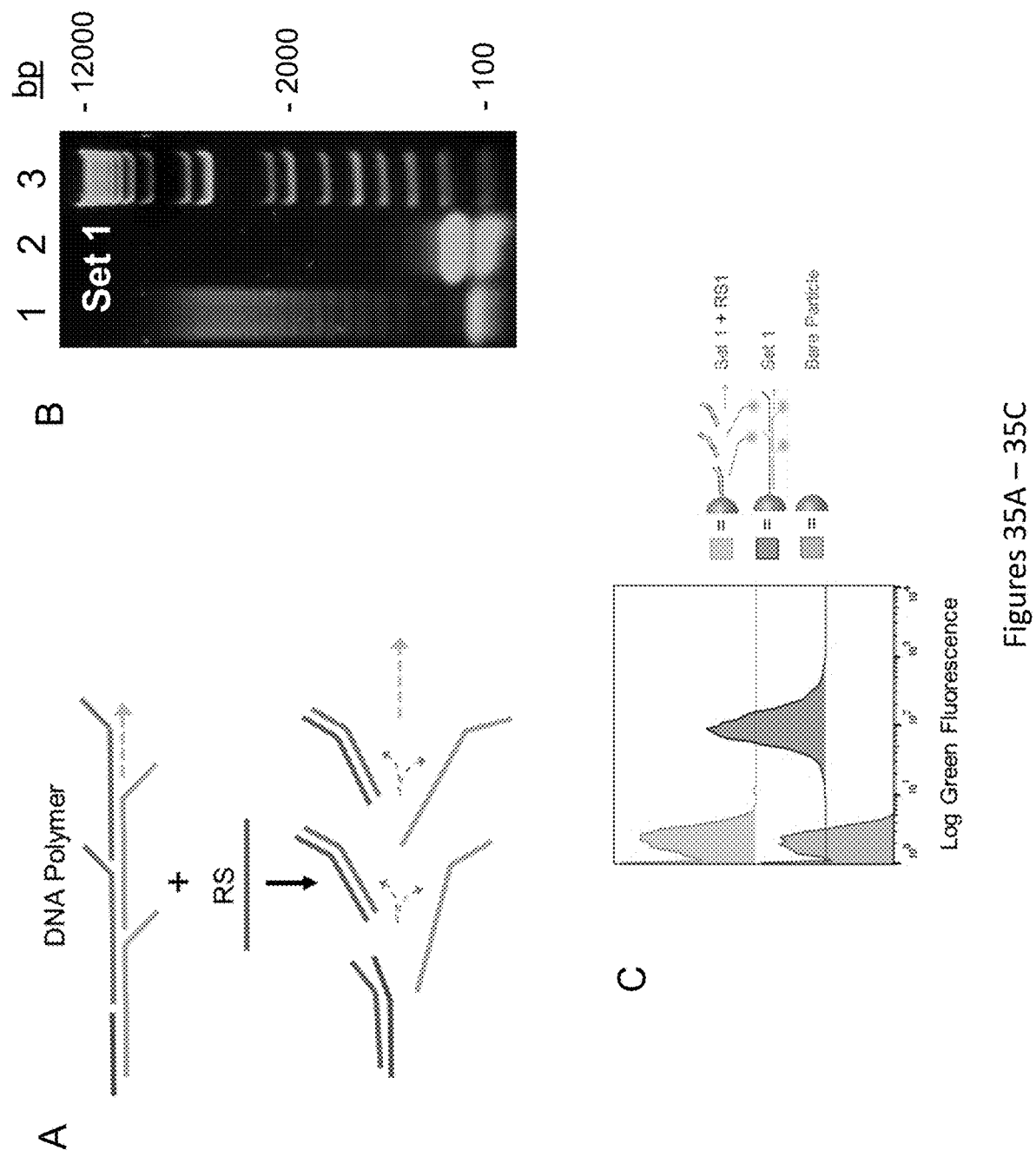
FIG. 35A through FIG. 35C, depicts destaining of fluorescent polymer conjugates with a reversing sequence.

To improve the current cell labeling system, experiments have been designed to trigger the release of labeling molecules using complementary DNA sequences that depolymerize DNA labeling polymers and destain cells. The hybridization region on the DNA polymer can either be a single location at the base of the polymer, or multiple points throughout the polymer (FIG. 35A). The reversing sequence (RS) should be capable of binding to the DNA polymer with a greater number of base pairs than are used to hybridize monomers, thus competitively displacing the polymer.

Initial studies have been carried out with one set of DNA polymers and show promise in triggering depolymerization. The electrophoretic gel image in FIG. 35B shows that DNA Set 1 polymers can be completely deconstructed using a RS. This reversing sequence was also designed to avoid the triggered dissociation of Set 2 polymers for controlled destaining applications. The reversing of DNA polymer labels has also been demonstrated from a surface by using microparticles as a model. In FIG. 5-1 C, DNA polymers with quantum dot labels are triggered to detach using RS. This detachment decreases the average fluorescence intensity by over an order of magnitude. RS can be applied to cells that are labeled with polyvalent fluorophores. Additionally, another RS designed to specifically depolymerize Set 2 can be used alone or in combination with the RS for Set 1 to trigger dissociation of multiple polymers. Finally, both sets of polymer-conjugates can be used to label cells in multiple staining and destaining rounds.

Example 6: Sequences

Sequences of oligonucleotides used in the exemplary embodiments of the invention are set forth in Table 1.

| SEQ ID NO | Description | Sequence |
|---|---|---|
| SEQ ID NO: 1 | Initiator ssDNA oligonucleotide, included in the targeting complex | CCTCATCCCACTCCTACCTAAACCAAAAA |
| SEQ ID NO: 2 | Hair-pin forming DNA oligonucleotide, polymerizes to form a dsDNA product | GGTTTAGGTAGGAGTGGGATGAGGCCAA ATCCTCATCCCACTCCTACC |
| SEQ ID NO: 3 | Hair-pin forming DNA oligonucleotide, polymerizes to form a dsDNA product with a side group | GGTTTAGGTAGGAGTGGGATGAGGCCAA ATCCTCATCCCACTCCTACCACTCACTCC C |
| SEQ ID NO: 4 | Hair-pin forming DNA oligonucleotide, polymerizes to form a dsDNA product | CCTCATCCCACTCCTACCTAAACCGGTAG GAGTGGGATGAGGATTTGG |
| SEQ ID NO: 5 | Hair-pin forming DNA oligonucleotide, polymerizes to form a dsDNA product with a side group | CCACTCACTCACCTCACCTTCAACCTTCA CCTCATCCCACTCCTACCTAAACCGGTAG GAGTGGGATGAGGATTTGG |
| SEQ ID NO: 6 | Hair-pin forming DNA oligonucleotide, polymerizes to form a dsDNA product with a side group | GTTGAAGGTGAGGTGAGTGAGTGGCCAC TTCCACTCACTCACCTCACC |
| SEQ ID NO: 7 | Hair-pin forming DNA oligonucleotide, polymerizes to form a dsDNA product with a side group | GTTGAAGGTGAGGTGAGTGAGTGGCCAC TTCCACTCACTCACCTCACCCTAAATCCA C |
| SEQ ID NO: 8 | Hair-pin forming DNA oligonucleotide, polymerizes to form a dsDNA product with a side group | CCACTCACTCACCTCACCTTCAACGGTGA GGTGAGTGAGTGGAAGTGG |
| SEQ ID NO: 9 | ssDNA oligonucleotide, hybridizes to a side group of a dsDNA polymerization product | GGTAGGAGTGGGATGAGGATTTGG |
| SEQ ID NO: 10 | ssDNA oligonucleotide, hybridizes to a side group of a dsDNA polymerization product for depolymerization | GTGGATTTAGGGTGAGGTGAGTGAGTGG AAGTGG |
| SEQ ID NO: 11 | ssDNA oligonucleotide, hybridizes to a side group of a dsDNA polymerization product for depolymerization | GGGAGTGAGTGGTAGGAGTGGGATGAGG ATTTGG |

| SEQ ID NO | Description | Sequence |
|---|---|---|
| SEQ ID NO: 12 | DI1 (Initiator ssDNA oligonucleotide for Set 1) | CAACTTCCACTCCACTCACTCACCCGCGC |
| SEQ ID NO: 13 | DI2 (Initiator ssDNA oligonucleotide for Set 2) | CAAAGTAGTCTAGGATTCGGCGTGCAGGT |
| SEQ ID NO: 14 | DM1_1 (Hair-pin forming DNA oligonucleotide for Set 1) | TTTCCCTTATATTCTCTCTCTCCCCACTCCACTCACTCACCTTCACCGGTGAGTGAGTGGAGTGGAAGTTG |
| SEQ ID NO: 15 | DM2_1 (Hair-pin forming DNA oligonucleotide for Set 1) | GGTGAAGGTGAGTGAGTGGAGTGGCAACTTCCACTCCACTCACTCACCCGCTCCCTTC |
| SEQ ID NO: 16 | DM2_1_FAM (Shortened hair-pin forming DNA oligonucleotide for Set 1) | GGTGAAGGTGAGTGAGTGGAGTGGCAACTTCCACTCCACTCACTCACC |
| SEQ ID NO: 17 | DM1_2 (Hair-pin forming DNA oligonucleotide for Set 2) | TTAACCCACGCCGAATCCTAGACTCAAAGTAGTCTAGGATTCGGCGTGCTCTTTTTTTTTTTTTTTTCCTTC |
| SEQ ID NO: 18 | DM2_2 (Hair-pin forming DNA oligonucleotide for Set 2) | AGTCTAGGATTCGGCGTGGGTTAACACGCCGAATCCTAGACTACTTTG |
| SEQ ID NO: 19 | DI1 Block (Polymerization inhibitory oligo for DI1) | CGCGC |
| SEQ ID NO: 20 | DI2 block (Polymerization inhibitory oligo for DI2) | CAGGT |
| SEQ ID NO: 21 | Set 1 branch linker | GAGAGAGAATATAAGGGAAAAAAAA |
| SEQ ID NO: 22 | Set 2 branch linker | AAAAGAAGGAAAAAAAAAAAAAAA |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A method for detection of one or more molecules of interest, the method comprising: (a) a polymerization step (b) a detection step and (c) a de-polymerization step, wherein the polymerization step comprises hybridizing an initiator ssDNA oligonucleotide with at least two hairpin DNA oligonucleotides to form a double-stranded DNA (dsDNA) polymerization product, and wherein the dsDNA polymerization product comprises one or more ssDNA side groups.

2. The method of claim 1, wherein the initiator ssDNA oligonucleotide is selected from the group consisting of SEQ ID NO: 1, SEQ ID NO: 12 and SEQ ID NO: 13.

3. The method of claim 1, wherein the initiator ssDNA oligonucleotide is SEQ ID NO: 1 and wherein the one or more hairpin DNA oligonucleotides comprise one or more sequences selected from the group consisting of SEQ ID NO: 2, SEQ ID NO: 3, SEQ ID NO:4 and SEQ ID NO:5.

4. The method of claim 1, wherein the initiator ssDNA oligonucleotide is SEQ ID NO: 12 and wherein the one or more hairpin DNA oligonucleotides comprise one or more sequences selected from the group consisting of SEQ ID NO: 14, SEQ ID NO: 15 and SEQ ID NO: 16.

5. The method of claim 1, wherein the initiator ssDNA oligonucleotide is SEQ ID NO: 13 and wherein the one or more hairpin DNA oligonucleotides comprise one or more sequences selected from the group consisting of SEQ ID NO: 17 and SEQ ID NO: 18.

6. The method of claim 1, wherein the dsDNA polymerization product is extended to become a branched product.

7. The method of claim 6, wherein the branched product is formed from hybridization of a ssDNA oligonucleotide to a side group of the dsDNA polymerization product.

8. The method of claim 7, wherein the ssDNA oligonucleotide is conjugated to a molecule.

9. The method of claim 8, wherein the molecule is selected from the group consisting of a quantum dot, a monomeric fluorophore, a polymeric fluorophore and biotin.

10. The method of claim 6 wherein the dsDNA polymerization product results from contacting an initiator ssDNA oligonucleotide having a sequence as set forth in SEQ ID NO: 1 with at least two hairpin DNA oligonucleotides selected from the group consisting of SEQ ID NO: 2, SEQ ID NO: 3, SEQ ID NO:4 and SEQ ID NO:5, and is further extended into a branched product by contacting the dsDNA polymerization product with one or more DNA oligonucleotides selected from the group consisting of SEQ ID NO: 6, SEQ ID NO:7 and SEQ ID NO:8.

11. A method for detection of one or more molecules of interest, the method comprising: (a) a polymerization step (b) a detection step, (c) a de-polymerization step, and (d) contacting a molecule to be detected with a complex comprising a ssDNA oligonucleotide component, and a linker molecule, wherein the polymerization step comprises hybridizing an initiator ssDNA oligonucleotide with at least two hairpin DNA oligonucleotides to form a double-stranded DNA (dsDNA) polymerization product.

12. The method of claim 11, wherein the ssDNA oligonucleotide component comprises a sequence selected from the group consisting of SEQ ID NO: 1, SEQ ID NO: 12 and SEQ ID NO: 13.

13. The method of claim 11, wherein the linker molecule is selected from the group consisting of a peptide, a protein, an immunogenic particle, an antibody, an oligonucleotide, and a microparticle.

14. The method of claim 11, wherein the molecule to be detected is a biological molecule.

15. The method of claim 14, wherein polymerization is initiated at the site of a biological molecule through the linkage of the initiator ssDNA oligonucleotide to the biological molecule through the association of the complex comprising a ssDNA oligonucleotide component, and a linker molecule.

16. The method of claim 15, wherein the biological molecule is selected from the group consisting of a peptide, a protein, and a nucleic acid.

17. The method of claim 11, wherein part (b) comprises detection of a dsDNA polymerization product.

18. The method of claim 17, wherein detection comprises detection of a DNA-conjugated molecule.

19. The method of claim 18, wherein the DNA-conjugated molecule is conjugated to a DNA oligonucleotide selected from the group consisting of a ssDNA oligonucleotide and a hairpin DNA oligonucleotide.

20. The method of claim 19, wherein at least a portion of the DNA oligonucleotide is complementary to a side group of a dsDNA polymerization product.

21. The method of claim 19, wherein the DNA-conjugated molecule is conjugated to a ssDNA oligonucleotide having a sequence as set forth in SEQ ID NO: 21, having a region complementary to a side group of a dsDNA polymerization product formed from hybridization of SEQ ID NO: 14 with SEQ ID NO: 15.

22. The method of claim 19, wherein the DNA-conjugated molecule is conjugated to a ssDNA oligonucleotide having a sequence as set forth in SEQ ID NO: 22, having a region complementary to a side group of a dsDNA polymerization product formed from hybridization of SEQ ID NO: 17 with SEQ ID NO: 18.

23. The method of claim 18, wherein the molecule is selected from the group consisting of a quantum dot, a DNA-conjugated monomeric fluorophore and a DNA-conjugated polymeric fluorophore.

24. The method of claim 23, wherein a DNA-conjugated fluorophore is selected from the group consisting of a succinimidyl ester activated fluorophore, Coumarin, FITC and TRITC.

25. The method of claim 11, wherein part (b) comprises detection of multiple dsDNA polymerization products in a single sample.

26. The method of claim 25, wherein multiple dsDNA polymerization products, are formed concurrently in a single sample.

27. The method of claim 26, wherein one dsDNA polymerization product has an initiator ssDNA oligonucleotide as set forth in SEQ ID NO: 12 and wherein the hairpin DNA oligonucleotides are selected from the group consisting of SEQ ID NO: 14, SEQ ID NO: 15 and SEQ ID NO: 16, and another dsDNA polymerization product has an initiator ssDNA oligonucleotide as set forth in SEQ ID NO: 13 and wherein the hairpin DNA oligonucleotides are selected from the group consisting of SEQ ID NO: 17 and SEQ ID NO: 18.

28. The method of claim 11, wherein part (c) comprises depolymerization of a linear dsDNA or branched product.

29. The method of claim 28, wherein a DNA oligonucleotide hybridizes competitively with a DNA hairpin oligonucleotide to disengage it from the linear dsDNA or branched product.

30. The method of claim 29, wherein the competitive hybridization is initiated through hybridization to a side group of the linear dsDNA product, and extends through a region of complementary sequence to the hairpin DNA oligonucleotide.

31. The method of claim 30, wherein the hairpin DNA oligonucleotides that hybridized to form a linear dsDNA product are inactivated for further polymerization.

32. The method of claim 29, wherein the DNA oligonucleotide comprises a sequence of SEQ ID NO: 10 or SEQ ID NO:11.

33. The method of claim 11, wherein parts (a), (b) and (c) are performed sequentially in a manner as to generate a detectable dsDNA polymer at the site of a biological molecule and subsequently detect and then remove the detectable dsDNA polymer.

34. The method of claim 11, wherein parts (a), (b) and (c) are performed sequentially in a manner as to generate multiple detectable dsDNA polymers at the site of multiple biological molecules and subsequently detect and then remove the detectable dsDNA polymers.

35. The method of claim 11, wherein parts (a), (b), (c) are performed sequentially multiple times within the same sample serving as a method for detection of multiple biological molecules.

36. The method of claim 11, wherein parts (a), (b) and (c) are performed in vivo, in vitro or in situ.

37. The method of claim 11, wherein parts (a), (b), (c) and (d) are performed on a biological sample.

* * * * *

SEQUENCE LISTING

<160> NUMBER OF SEQ ID NOS: 22

<210> SEQ ID NO 1
<211> LENGTH: 29
<212> TYPE: DNA
<213> ORGANISM: Artificial Sequence
<220> FEATURE:
<223> OTHER INFORMATION: Initiator ssDNA oligonucleotide

<400> SEQUENCE: 1
cctcatccca ctcctaccta aaccaaaaa                                  29

<210> SEQ ID NO 2
<211> LENGTH: 48
<212> TYPE: DNA
<213> ORGANISM: Artificial Sequence
<220> FEATURE:
<223> OTHER INFORMATION: Hair-pin forming DNA oligonucleotide

<400> SEQUENCE: 2
ggtttaggta ggagtgggat gaggccaaat cctcatccca ctcctacc            48

```
<210> SEQ ID NO 3
<211> LENGTH: 58
<212> TYPE: DNA
<213> ORGANISM: Artificial Sequence
<220> FEATURE:
<223> OTHER INFORMATION: Hair-pin forming DNA oligonucleotide

<400> SEQUENCE: 3
ggtttaggta ggagtgggat gaggccaaat cctcatccca ctcctaccac tcactccc      58

<210> SEQ ID NO 4
<211> LENGTH: 48
<212> TYPE: DNA
<213> ORGANISM: Artificial Sequence
<220> FEATURE:
<223> OTHER INFORMATION: Hair-pin forming DNA oligonucleotide

<400> SEQUENCE: 4
cctcatccca ctcctaccta aaccggtagg agtgggatga ggatttgg                 48

<210> SEQ ID NO 5
<211> LENGTH: 77
<212> TYPE: DNA
<213> ORGANISM: Artificial Sequence
<220> FEATURE:
<223> OTHER INFORMATION: Hair-pin forming DNA oligonucleotide, with side
      group

<400> SEQUENCE: 5
ccactcactc acctcacctt caaccttcac ctcatcccac tcctacctaa accggtagga    60
gtgggatgag gatttgg                                                   77

<210> SEQ ID NO 6
<211> LENGTH: 48
<212> TYPE: DNA
<213> ORGANISM: Artificial Sequence
<220> FEATURE:
<223> OTHER INFORMATION: Hair-pin forming DNA oligonucleotide, with side
      group

<400> SEQUENCE: 6
gttgaaggtg aggtgagtga gtggccactt ccactcactc acctcacc                 48

<210> SEQ ID NO 7
<211> LENGTH: 58
<212> TYPE: DNA
<213> ORGANISM: Artificial Sequence
<220> FEATURE:
<223> OTHER INFORMATION: Hair-pin forming DNA oligonucleotide, with side
      group

<400> SEQUENCE: 7
gttgaaggtg aggtgagtga gtggccactt ccactcactc acctcaccct aaatccac      58

<210> SEQ ID NO 8
<211> LENGTH: 48
<212> TYPE: DNA
<213> ORGANISM: Artificial Sequence
<220> FEATURE:
<223> OTHER INFORMATION: Hair-pin forming DNA oligonucleotide, with side
      group

<400> SEQUENCE: 8
ccactcactc acctcacctt caacggtgag gtgagtgagt ggaagtgg                 48
```

<210> SEQ ID NO 9
<211> LENGTH: 24
<212> TYPE: DNA
<213> ORGANISM: Artificial Sequence
<220> FEATURE:
<223> OTHER INFORMATION: ssDNA oligonucleotide, hybridizes to a side
      group

<400> SEQUENCE: 9
ggtaggagtg ggatgaggat ttgg                                        24

<210> SEQ ID NO 10
<211> LENGTH: 34
<212> TYPE: DNA
<213> ORGANISM: Artificial Sequence
<220> FEATURE:
<223> OTHER INFORMATION: ssDNA oligonucleotide, hybridizes to a side
      group for depolymerization

<400> SEQUENCE: 10
gtggatttag ggtgaggtga gtgagtggaa gtgg                             34

<210> SEQ ID NO 11
<211> LENGTH: 34
<212> TYPE: DNA
<213> ORGANISM: Artificial Sequence
<220> FEATURE:
<223> OTHER INFORMATION: ssDNA oligonucleotide, hybridizes to a side
      group for depolymerization

<400> SEQUENCE: 11
gggagtgagt ggtaggagtg ggatgaggat ttgg                             34

<210> SEQ ID NO 12
<211> LENGTH: 29
<212> TYPE: DNA
<213> ORGANISM: Artificial Sequence
<220> FEATURE:
<223> OTHER INFORMATION: DI1 (Initiator ssDNA oligonucleotide for Set 1)

<400> SEQUENCE: 12
caacttccac tccactcact cacccgcgc                                   29

<210> SEQ ID NO 13
<211> LENGTH: 29
<212> TYPE: DNA
<213> ORGANISM: Artificial Sequence
<220> FEATURE:
<223> OTHER INFORMATION: DI2 (Initiator ssDNA oligonucleotide for Set 2)

<400> SEQUENCE: 13
caaagtagtc taggattcgg cgtgcaggt                                   29

<210> SEQ ID NO 14
<211> LENGTH: 73
<212> TYPE: DNA
<213> ORGANISM: Artificial Sequence
<220> FEATURE:
<223> OTHER INFORMATION: DM1_1 (Hair-pin forming DNA oligonucleotide for
      Set 1)

<400> SEQUENCE: 14
tttcccttat attctctctc tctccccact ccactcactc accttccacg gtgagtgagt   60
ggagtggaag ttg                                                    73

```
<210> SEQ ID NO 15
<211> LENGTH: 58
<212> TYPE: DNA
<213> ORGANISM: Artificial Sequence
<220> FEATURE:
<223> OTHER INFORMATION: DM2_1 (Hair-pin forming DNA oligonucleotide for
      Set 1)

<400> SEQUENCE: 15
ggtgaaggtg agtgagtgga gtggcaactt ccactccact cactcacccg ctcccttc         58

<210> SEQ ID NO 16
<211> LENGTH: 48
<212> TYPE: DNA
<213> ORGANISM: Artificial Sequence
<220> FEATURE:
<223> OTHER INFORMATION: DM2_1_FAM (Shortened hair-pin forming DNA
      oligonucleotide for Set 1)

<400> SEQUENCE: 16
ggtgaaggtg agtgagtgga gtggcaactt ccactccact cactcacc                    48

<210> SEQ ID NO 17
<211> LENGTH: 73
<212> TYPE: DNA
<213> ORGANISM: Artificial Sequence
<220> FEATURE:
<223> OTHER INFORMATION: DM1_2 (Hair-pin forming DNA oligonucleotide for
      Set 2)

<400> SEQUENCE: 17
ttaacccacg ccgaatccta gactcaaagt agtctaggat tcggcgtgct cttttttttt       60 tttttttcc ttc                                                           73

<210> SEQ ID NO 18
<211> LENGTH: 48
<212> TYPE: DNA
<213> ORGANISM: Artificial Sequence
<220> FEATURE:
<223> OTHER INFORMATION: DM2_2 (Hair-pin forming DNA oligonucleotide for
      Set 2)

<400> SEQUENCE: 18
agtctaggat tcggcgtggg ttaacacgcc gaatcctaga ctactttg                    48

<210> SEQ ID NO 19
<211> LENGTH: 5
<212> TYPE: DNA
<213> ORGANISM: Artificial Sequence
<220> FEATURE:
<223> OTHER INFORMATION: DI1 Block (Polymerization inhibitory oligo for
      DI1)

<400> SEQUENCE: 19 cgcgc                                                                    5

<210> SEQ ID NO 20
<211> LENGTH: 5
<212> TYPE: DNA
<213> ORGANISM: Artificial Sequence
<220> FEATURE:
<223> OTHER INFORMATION: DI2 block (Polymerization inhibitory oligo for
      DI2)

<400> SEQUENCE: 20 caggt                                                                    5
```

```
<210> SEQ ID NO 21
<211> LENGTH: 25
<212> TYPE: DNA
<213> ORGANISM: Artificial Sequence
<220> FEATURE:
<223> OTHER INFORMATION: Set 1 branch linker

<400> SEQUENCE: 21
gagagagaat ataagggaaa aaaaa                                      25

<210> SEQ ID NO 22
<211> LENGTH: 25
<212> TYPE: DNA
<213> ORGANISM: Artificial Sequence
<220> FEATURE:
<223> OTHER INFORMATION: Set 2 branch linker

<400> SEQUENCE: 22
aaaaagaagg aaaaaaaaaa aaaaa                                      25
```